US010889656B2

(12) United States Patent
Mori et al.

(10) Patent No.: US 10,889,656 B2
(45) Date of Patent: Jan. 12, 2021

(54) HEPARAN SULFATE HAVING HIGH 3-O-SULFATION RATE IN GLUCOSAMINE RESIDUES

(71) Applicant: AJINOMOTO CO., INC., Tokyo (JP)

(72) Inventors: Kenichi Mori, Kanagawa (JP); Yuriko Tokura, Kanagawa (JP); Shunsuke Yamazaki, Kanagawa (JP); Tomoko Shimizu, Kanagawa (JP); Yasuhiro Mihara, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/018,487

(22) Filed: Jun. 26, 2018

(65) Prior Publication Data

US 2018/0298117 A1 Oct. 18, 2018

Related U.S. Application Data

(63) Continuation of application No. PCT/JP2016/087689, filed on Dec. 16, 2016.

(30) Foreign Application Priority Data

Dec. 28, 2015 (JP) ................................ 2015-257022

(51) Int. Cl.

*C08B 37/00* (2006.01)
*A61K 31/727* (2006.01)
*C12P 19/04* (2006.01)
*A61P 7/02* (2006.01)
*C12N 15/09* (2006.01)

(52) U.S. Cl.

CPC ........ *C08B 37/0075* (2013.01); *A61K 31/727* (2013.01); *A61P 7/02* (2018.01); *C12P 19/04* (2013.01); *C12N 15/09* (2013.01)

(58) Field of Classification Search

CPC . A61K 31/726; A61K 31/727; C08B 37/0075
See application file for complete search history.

(56) References Cited

U.S. PATENT DOCUMENTS

| | | | | |
|---|---|---|---|---|
| 4,396,762 | A * | 8/1983 | Langer | A61K 31/715 435/269 |
| 8,227,449 | B2 | 7/2012 | Oreste et al. | |
| 2008/0207895 | A1 | 8/2008 | Rosenberg et al. | |
| 2011/0281820 | A1* | 11/2011 | Oreste | A61K 31/727 514/56 |
| 2012/0116066 | A1 | 5/2012 | Patel et al. | |
| 2012/0322114 | A1 | 12/2012 | Liu et al. | |
| 2016/0201103 | A1 | 7/2016 | Yamazaki et al. | |

FOREIGN PATENT DOCUMENTS

| | | | |
|---|---|---|---|
| CN | 101531723 | A | 9/2009 |
| WO | WO2004/050673 | A2 | 6/2004 |
| WO | WO2005/058976 | A2 | 6/2005 |
| WO | WO2005/058976 | A3 | 6/2005 |
| WO | WO2012/088416 | A2 | 6/2012 |
| WO | WO2012/088416 | A3 | 6/2012 |
| WO | WO2015/050184 | A1 | 4/2015 |

OTHER PUBLICATIONS

Xu, Y. et al "Homogeneous low-molecular-weight heparins . . . " Nat. Chem. Biol., vol. 10, No. 4, pp. 247-250. (Year: 2014).*

Copeland, R. et al "Using 3-O-sulfated heparin octasaccharide . . . " Biochem., vol. 47, pp. 5774-5783. (Year: 2008).*

Liu, J. et al "Anticoagulant heparan sulfate . . . " Appl. Microbiol. Biotechnol., vol. 74, pp. 263-272. (Year: 2007).*

Bhaskar, U. et al "Combinatorial one-pot chemoenzymatic synthesis of heparin" Carbohyd. Polym., vol. 122, pp. 399-407. (Year: 2015).*

Zhang, C. et al "Metabolic engineering of *Escherichia coli* BZ21 for biosynthesis . . . " Metab. Eng., vol. 14, pp. 521-527. (Year: 2012).*

Pempe, E. H., et al., "Probing Structural Selectivity of Synthetic Heparin Binding to Stabilin Protein Receptors," J. Biol. Chem. 2012;287(25):20774-20783.

Xu, Y., et al., "Chemoenzymatic Synthesis of Homogeneous Ultralow Molecular Weight Heparins," Science 2011;334:498-501.

Supplementary European Search Report for European Patent App. No. 16881651.0 (dated Jul. 31, 2019).

Lindahl, U., et al., "Generation of "Neoheparin" from *E. coli* K5 Capsular Polysaccharide," J. Med. Chem. 2005:48 (2):349-352.

Zhang, Z., et al., "Solution Structures of Chemoenzymatically Synthesized Heparin and Its Precursors," J. Am. Chem. Soc. 2008;139(39):12998-13007.

Zhang, L., et al., "The Retinoic Acid and cAMP-dependent Up-regulation of 3-O-Sulfotransferase-1 Leads to a Dramatic Augmentation of Anticoagulantly Active Heparan Sulfate Biosynthesis in F9 Embryonal Carcinoma Cells," J. Biol. Chem. 1998;273(43):27998-28003.

Toida, T., et al., "Preparation and anticoagulant activity of fully O-sulphonated glycosaminoglycans," Int. J. Biol. Macromol. 1999;26:233-241.

Chen, J., et al., "Using an Enzymatic Combinatorial Approach to Identify Anticoagulant Heparan Sulfate Structures," Chem. & Biol. 2007;14:986-993.

Atha, D., et al., "Contribution of 3-O- and 6-O-Sulfated Glucosamine Residues in the Heparin-Induced Conformational Change in Antithrombin III," Biochem. 1987;26:6454-6461.

Lindahl, U., et al., "Evidence for a 3-O-sulfated D-glucosamine residue in the antithrombin-binding sequence of heparin," Proc. Natl. Acad. Sci. USA 1980;77(11):6551-6555.

Lindahl, U., et al., "Regulated Diversity of Heparan Sulfate," J. Biol. Chem. 1998;273:24979-24982.

(Continued)

*Primary Examiner* — Leigh C Maier

(74) *Attorney, Agent, or Firm* — Cermak Nakajima & McGowan LLP; Shelly Guest Cermak

(57) ABSTRACT

The present invention provides a novel sulfated polysaccharide having anticoagulant activity. Specifically, the present invention provides a polysaccharide that includes a repetitive structure of a disaccharide unit composed of a hexuronic acid (HexA) residue and a α-D-glucosamine (GlcN) residue and having 13% or higher of a 3-O-sulfation rate in GlcN residues.

23 Claims, No Drawings

Specification includes a Sequence Listing.

(56) References Cited

OTHER PUBLICATIONS

Chai, W., et al., "Relative Susceptibilities of the Glucosamine-Glucuronic Acid and N-Acetylglucosamin-Glucuronic Acid Linkages to Heparin Lyase III," Biochem. 2004;43:8590-8599.

International Search Report and Written Opinion for PCT Patent App. No. PCT/JP2016/087689 (dated Mar. 14, 2017) with English language translation of the ISR.

* cited by examiner

SEQUENCE LISTING

```
<160> NUMBER OF SEQ ID NOS: 41

<210> SEQ ID NO 1
<211> LENGTH: 7467
<212> TYPE: DNA
<213> ORGANISM: Escherichia coli
<220> FEATURE:
<221> NAME/KEY: CDS
<222> LOCATION: (445)..(1164)
<220> FEATURE:
<221> NAME/KEY: CDS
<222> LOCATION: (1593)..(3284)
<220> FEATURE:
<221> NAME/KEY: CDS
<222> LOCATION: (4576)..(6138)
<220> FEATURE:
<221> NAME/KEY: CDS
<222> LOCATION: (6180)..(7358)

<400> SEQUENCE: 1

ggaggcctga ttactgttgc actaacagtg tcattgccgg agattgtaat cacactctat      60

ataattatat aaactctatt gtatttagtg tatgaggagg atggacagta tactttgaac     120

taggtaatta tgaatttgat cgtgatctcg taatacgttg ctgttattct ttaattaatt     180

atctgccaat ttatttttag atagttacag gaaatgttta tgcaaagagt ggtttgatat     240

ggtaagagta ataatttaga tgaagataaa tatatcaaac gtacacccta gtagttattt     300

ttaattaaac atatcgtcca tgaggtgcgg agtcattcta atcaacttaa tgtgttctgt     360

ttattaagca tttcctataa ataaacgact atcaatacgt tgatagtttt cattaacatg     420

caatattaat taaaatatta cccc atg att gtt gca aat atg tca tca tac        471
                           Met Ile Val Ala Asn Met Ser Ser Tyr
                           1               5

cca cct cga aaa aaa gag ttg gtg cat tct ata caa agt tta cat gct      519
Pro Pro Arg Lys Lys Glu Leu Val His Ser Ile Gln Ser Leu His Ala
10                  15                  20                  25

caa gta gat aaa att aat ctt tgc ctg aat gag ttt gaa gaa att cct      567
Gln Val Asp Lys Ile Asn Leu Cys Leu Asn Glu Phe Glu Glu Ile Pro
                30                  35                  40

gag gaa tta gat ggt ttt tca aaa tta aat cca gtt att cca gat aaa      615
Glu Glu Leu Asp Gly Phe Ser Lys Leu Asn Pro Val Ile Pro Asp Lys
            45                  50                  55

gat tat aag gat gtg ggc aaa ttt ata ttt cct tgc gct aaa aat gat      663
Asp Tyr Lys Asp Val Gly Lys Phe Ile Phe Pro Cys Ala Lys Asn Asp
        60                  65                  70

atg atc gta ctt aca gat gat gat att att tac cct ccc gat tat gta      711
Met Ile Val Leu Thr Asp Asp Asp Ile Ile Tyr Pro Pro Asp Tyr Val
    75                  80                  85

gaa aaa atg ctc aat ttt tat aat tcc ttt gca ata ttc aat tgc att      759
Glu Lys Met Leu Asn Phe Tyr Asn Ser Phe Ala Ile Phe Asn Cys Ile
90                  95                  100                 105

gtt ggg att cat ggc tgt ata tac ata gat gca ttt gat gga gat cag      807
Val Gly Ile His Gly Cys Ile Tyr Ile Asp Ala Phe Asp Gly Asp Gln
                110                 115                 120

tct aaa aga aaa gta ttt tca ttt act caa ggg cta ttg cga ccg aga      855
```

```
Ser Lys Arg Lys Val Phe Ser Phe Thr Gln Gly Leu Leu Arg Pro Arg
            125                 130                 135

gtt gta aat caa tta ggt aca ggg act gtt ttt ctt aag gca gat caa      903
Val Val Asn Gln Leu Gly Thr Gly Thr Val Phe Leu Lys Ala Asp Gln
        140                 145                 150

tta cca tct tta aaa tat atg gat ggt tct caa cga ttc gtc gat gtt      951
Leu Pro Ser Leu Lys Tyr Met Asp Gly Ser Gln Arg Phe Val Asp Val
    155                 160                 165

aga ttt tct cgc tat atg tta gag aat gaa att ggt atg ata tgt gtt      999
Arg Phe Ser Arg Tyr Met Leu Glu Asn Glu Ile Gly Met Ile Cys Val
170                 175                 180                 185

ccc aga gaa aaa aac tgg cta aga gag gtc tca tca ggt tca atg gaa     1047
Pro Arg Glu Lys Asn Trp Leu Arg Glu Val Ser Ser Gly Ser Met Glu
                190                 195                 200

gga ctt tgg aac aca ttt aca aaa aaa tgg cct tta gac atc ata aaa     1095
Gly Leu Trp Asn Thr Phe Thr Lys Lys Trp Pro Leu Asp Ile Ile Lys
            205                 210                 215

gaa aca caa gca atc gca gga tat tca aaa ctt aac ctc gaa tta gtg     1143
Glu Thr Gln Ala Ile Ala Gly Tyr Ser Lys Leu Asn Leu Glu Leu Val
        220                 225                 230

tat aat gtg gaa ggg taa aaa cttacttttt tattcacatt cctgtatttt        1194
Tyr Asn Val Glu Gly     Lys
    235

gtgttggttt ctgaagttta tagtataaat acttgtttta aatagttgta cgttgatatt   1254

ttgttatata cttatttaaa ccatttgttt tatgattttg aaaaatatca gcgttagttt   1314

ggtagagttt ataattaaga tttttgtcta aaagaaggtg gtaacgcaat atgtcaatta   1374

ttaggaggtg ctctgagtta tattgatatt gtttattgat gaatggctat accaaataaa   1434

tcagatgtgc tattgagata tagatagttt catttagtat tatcacataa cgccacctaa   1494

attacattac agatttgaaa tatatgtctg caatatcacc attacgataa acgacagtgt   1554

ttaaaataaa gtaatcttgt agataataaa gaggaaat atg atg aat aaa tta gtg   1610
                                          Met Met Asn Lys Leu Val
                                          240                 245

cta gtc gga cat cct ggc tca aag tat cag ata gtt gaa cat ttt ttg     1658
Leu Val Gly His Pro Gly Ser Lys Tyr Gln Ile Val Glu His Phe Leu
                250                 255                 260

aaa gaa att ggc atg aac tca cca aat tat tct aca agt aat aaa att     1706
Lys Glu Ile Gly Met Asn Ser Pro Asn Tyr Ser Thr Ser Asn Lys Ile
            265                 270                 275

tcc cca gaa tat atc acc gct tca tta tgt caa ttt tat caa aca cca     1754
Ser Pro Glu Tyr Ile Thr Ala Ser Leu Cys Gln Phe Tyr Gln Thr Pro
        280                 285                 290

gaa gtt aat gat gta gta gat gag aga gaa ttc tca gct gtt caa gtc     1802
Glu Val Asn Asp Val Val Asp Glu Arg Glu Phe Ser Ala Val Gln Val
    295                 300                 305

tca acc atg tgg gat agc atg gtt ctt gaa cta atg atg aac aat cta     1850
Ser Thr Met Trp Asp Ser Met Val Leu Glu Leu Met Met Asn Asn Leu
310                 315                 320                 325

aat aac aaa ctt tgg ggg tgg gca gat cca tct ata ata ttt ttt ctt     1898
Asn Asn Lys Leu Trp Gly Trp Ala Asp Pro Ser Ile Ile Phe Phe Leu
                330                 335                 340

gat ttt tgg aaa aat ata gat aaa agc ata aaa ttc atc atg ata tat     1946
Asp Phe Trp Lys Asn Ile Asp Lys Ser Ile Lys Phe Ile Met Ile Tyr
            345                 350                 355

gat cac cct aaa tat aat tta atg cgt tca gta aat aat gcc cct ctc     1994
Asp His Pro Lys Tyr Asn Leu Met Arg Ser Val Asn Asn Ala Pro Leu
        360                 365                 370
```

```
tct tta aat ata aat aat agt gta gat aac tgg att gca tat aat aaa      2042
Ser Leu Asn Ile Asn Asn Ser Val Asp Asn Trp Ile Ala Tyr Asn Lys
    375                 380                 385

aga ttg ctt gat ttt ttt ttg gag aat aaa gaa cga tgt gtg ttg att      2090
Arg Leu Leu Asp Phe Phe Leu Glu Asn Lys Glu Arg Cys Val Leu Ile
390                 395                 400                 405

aat ttt gag gcg ttt caa agc aat aag aaa aat att ata aag cca ttg      2138
Asn Phe Glu Ala Phe Gln Ser Asn Lys Lys Asn Ile Ile Lys Pro Leu
                410                 415                 420

agt aat att ata aaa ata gat aat cta atg tct gcg cat tac aaa aat      2186
Ser Asn Ile Ile Lys Ile Asp Asn Leu Met Ser Ala His Tyr Lys Asn
            425                 430                 435

tca ata ttg ttt gat gtg gtt gag aat aat gat tat aca aaa tca aat      2234
Ser Ile Leu Phe Asp Val Val Glu Asn Asn Asp Tyr Thr Lys Ser Asn
        440                 445                 450

gaa att gcc ctg ctt gaa aaa tat aca act tta ttt tct tta agt gca      2282
Glu Ile Ala Leu Leu Glu Lys Tyr Thr Thr Leu Phe Ser Leu Ser Ala
    455                 460                 465

aat gag act gaa att aca ttt aat gat aca aag gtt agt gag tac tta      2330
Asn Glu Thr Glu Ile Thr Phe Asn Asp Thr Lys Val Ser Glu Tyr Leu
470                 475                 480                 485

gta tct gaa tta ata aaa gaa aga acc gag gtt ctg aag ctt tat aat      2378
Val Ser Glu Leu Ile Lys Glu Arg Thr Glu Val Leu Lys Leu Tyr Asn
                490                 495                 500

gag tta caa gcc tat gca aac cta cct tat ata gaa aca tcg aaa gat      2426
Glu Leu Gln Ala Tyr Ala Asn Leu Pro Tyr Ile Glu Thr Ser Lys Asp
            505                 510                 515

aac gtt tcg gct gag gct gca tta tgg gag gta gtc gaa gag aga aat      2474
Asn Val Ser Ala Glu Ala Ala Leu Trp Glu Val Val Glu Glu Arg Asn
        520                 525                 530

tct atc ttc aat att gta tct cat ttg gtg caa gag tca aaa aag aag      2522
Ser Ile Phe Asn Ile Val Ser His Leu Val Gln Glu Ser Lys Lys Lys
    535                 540                 545

gat gca gat att gaa ttg act aaa tct ata ttt aag aaa aga caa ttt      2570
Asp Ala Asp Ile Glu Leu Thr Lys Ser Ile Phe Lys Lys Arg Gln Phe
550                 555                 560                 565

tta tta ttg aac agg att aat gag cta aaa aaa gaa aag gaa gag gta      2618
Leu Leu Leu Asn Arg Ile Asn Glu Leu Lys Lys Glu Lys Glu Glu Val
                570                 575                 580

att aaa ctt tca aaa ata aat cac aac gat gtt gtg aga caa gaa aaa      2666
Ile Lys Leu Ser Lys Ile Asn His Asn Asp Val Val Arg Gln Glu Lys
            585                 590                 595

tat cca gat gat att gaa aaa aaa ata aat gac ata cag aaa tat gaa      2714
Tyr Pro Asp Asp Ile Glu Lys Lys Ile Asn Asp Ile Gln Lys Tyr Glu
        600                 605                 610

gaa gag ata agc gaa aaa gaa tca aaa ctc act cag gca ata tca gaa      2762
Glu Glu Ile Ser Glu Lys Glu Ser Lys Leu Thr Gln Ala Ile Ser Glu
    615                 620                 625

aaa gaa cag att tta aaa caa ttg cat aaa tat gaa gaa gag ata agc      2810
Lys Glu Gln Ile Leu Lys Gln Leu His Lys Tyr Glu Glu Glu Ile Ser
630                 635                 640                 645

gaa aaa gaa tca aaa ctc act cag gca ata tca gaa aaa gaa cag att      2858
Glu Lys Glu Ser Lys Leu Thr Gln Ala Ile Ser Glu Lys Glu Gln Ile
                650                 655                 660

tta aaa caa ttg cat ata gtg caa gag cag ttg gaa cac tat ttt ata      2906
Leu Lys Gln Leu His Ile Val Gln Glu Gln Leu Glu His Tyr Phe Ile
            665                 670                 675

gaa aat cag gaa att aaa aag aaa ctt cca cct gtg cta tat gga gca      2954
Glu Asn Gln Glu Ile Lys Lys Lys Leu Pro Pro Val Leu Tyr Gly Ala
        680                 685                 690
```

-continued

```
gct gag cag ata aaa caa gag tta ggt tat cga ctt ggt tat att ata     3002
Ala Glu Gln Ile Lys Gln Glu Leu Gly Tyr Arg Leu Gly Tyr Ile Ile
    695                 700                 705

gtc tcg tat tct aaa tcc ctc aag ggg att att acc atg cca ttt gca     3050
Val Ser Tyr Ser Lys Ser Leu Lys Gly Ile Ile Thr Met Pro Phe Ala
710                 715                 720                 725

ctt atc cgt gag tgt gtt ttt gaa aaa aaa cgt aag aag agt tat ggc     3098
Leu Ile Arg Glu Cys Val Phe Glu Lys Lys Arg Lys Lys Ser Tyr Gly
                730                 735                 740

gtt gat gtg cca ctc tat tta tat gct gat gct gat aag gct gaa aga     3146
Val Asp Val Pro Leu Tyr Leu Tyr Ala Asp Ala Asp Lys Ala Glu Arg
            745                 750                 755

gtt aag aaa cat tta tct tat caa tta ggg cag gct att atc tcc agt     3194
Val Lys Lys His Leu Ser Tyr Gln Leu Gly Gln Ala Ile Ile Ser Ser
        760                 765                 770

gct aat tcg ata ttt gga ttc att acc ctt cca ttt aag tta att gtt     3242
Ala Asn Ser Ile Phe Gly Phe Ile Thr Leu Pro Phe Lys Leu Ile Val
    775                 780                 785

gtt gtt tat aaa tat agg aga gct aaa atc aag ggc tgt taa             3284
Val Val Tyr Lys Tyr Arg Arg Ala Lys Ile Lys Gly Cys
790                 795                 800

aaatgtgaac cctaatgaga tatattgcaa attttatttt tctctttgtg gtgttttgct   3344

ttcgttaaaa tagttagtta ttttatttat ataatatcac gcattataat accaatttat   3404

acttttgcaa gtgaccgtat agattcgcca catattgcaa attttgttct ctcgtaaaat   3464

attttcttct ggtgtcagta attcgagcac ttcatgctgt cttttactgc agtatagtac   3524

taggttttca gctagtttct gattaaatat gtttagctct ttaaagagtc tatttattta   3584

aattcaatga actgttcttt cggcgttcgc ttaaaacgtt cagaggtgcg ttctaggcgt   3644

aaaggggtag gtccataggg cttgctagcg gattcctgcg gtgctttgtc gaagtttcct   3704

gggaactctt tcccgttatc tgcgatgccc tggttgatat cgatagggaa tagccggtct   3764

gcacggcaaa agaagagttt gatgatatca cagttaagtg acggcacggc ctgtgccaga   3824

gcgtagttgc tgtgttcgtc gatcatggta atgacataac agcgcagctc gcccattctg   3884

agctcaatag catctatacc aacgagctca ctgctcttta ccgggcgata gcgttttgat   3944

ctgcgggttg gaggattgta ttttttatga acagtgtttt tccttgggga ggcagtcaca   4004

tcggtatcag tcgcatttta tcgtgtgcgg ccgtgaacat cctgccgatg gttgaaatgc   4064

tcggacagac caggcggtgc tgttcactcc acggcttcaa gcaaacaaaa atctgttctt   4124

ctaggttggg aagctctatt ctcagtcgac gtatttctta cagaattacg agatgccatt   4184

gctttgtgcg atgtactagc ggagctttgc tacgcgaaat aggtgcctct gggccataat   4244

acagcgttcg tgtggataca gcaaaaactt ccgcaactgt attgatctca tgtttctccc   4304

agaagtatat tttttcatcc ttaattttgt aatctcaggt ataacaaagt gtttcatcac   4364

atagatgttg gcatggtaat gcctcaaata tccgccgcag atacgttgca tcaacttagc   4424

atttccctcg cttgtccgga gataattgca atatctctgt gagcttacac tgtgacattc   4484

gttgagtttt agtgatgttt ttaaagattt atatttataa tatttagtaa atgcagtttt   4544

attctcattt tatttatcat taagtgaatg t atg aac gca gaa tat ata aat      4596
                                   Met Asn Ala Glu Tyr Ile Asn
                                           805

tta gtt gaa cgt aaa aag aaa tta ggg aca aat att ggt gct ctt gat     4644
Leu Val Glu Arg Lys Lys Lys Leu Gly Thr Asn Ile Gly Ala Leu Asp
810                 815                 820                 825
```

```
ttt tta tta tca att cat aag gag aaa gtt gat ctt caa cat aaa aac     4692
Phe Leu Leu Ser Ile His Lys Glu Lys Val Asp Leu Gln His Lys Asn
                830                 835                 840

tcg cct tta aaa ggt aac gat aac ctt att cac aaa aga ata aac gaa     4740
Ser Pro Leu Lys Gly Asn Asp Asn Leu Ile His Lys Arg Ile Asn Glu
            845                 850                 855

tac gac aat gta ctt gaa cta tct aag aat gta tca gct cag aat tct     4788
Tyr Asp Asn Val Leu Glu Leu Ser Lys Asn Val Ser Ala Gln Asn Ser
        860                 865                 870

ggc aat gag ttt tct tat tta ttg gga tat gca gat tct ctt aga aaa     4836
Gly Asn Glu Phe Ser Tyr Leu Leu Gly Tyr Ala Asp Ser Leu Arg Lys
    875                 880                 885

gtt ggt atg ttg gat act tat att aaa att gtt tgt tat cta aca att     4884
Val Gly Met Leu Asp Thr Tyr Ile Lys Ile Val Cys Tyr Leu Thr Ile
890                 895                 900                 905

caa tct cgt tat ttt aaa aat ggc gaa cga gtt aag ctt ttt gaa cat     4932
Gln Ser Arg Tyr Phe Lys Asn Gly Glu Arg Val Lys Leu Phe Glu His
                910                 915                 920

ata agt aac gct cta cgg tat tca agg agt gat ttt ctc att aat ctt     4980
Ile Ser Asn Ala Leu Arg Tyr Ser Arg Ser Asp Phe Leu Ile Asn Leu
            925                 930                 935

att ttt gaa cga tat atc gaa tat ata aac cat cta aaa ttg tcg ccc     5028
Ile Phe Glu Arg Tyr Ile Glu Tyr Ile Asn His Leu Lys Leu Ser Pro
        940                 945                 950

aaa caa aaa gat ttt tat ttt tgt acg aag ttt tca aaa ttt cat gat     5076
Lys Gln Lys Asp Phe Tyr Phe Cys Thr Lys Phe Ser Lys Phe His Asp
    955                 960                 965

tat act aaa aat gga tat aaa tat tta gca ttt gat aat caa gcc gat     5124
Tyr Thr Lys Asn Gly Tyr Lys Tyr Leu Ala Phe Asp Asn Gln Ala Asp
970                 975                 980                 985

gca ggg tat ggc ctg act tta tta tta aat gca aac gat gat atg  caa    5172
Ala Gly Tyr Gly Leu Thr Leu Leu Leu Asn Ala Asn Asp Asp Met  Gln
                990                 995                 1000

gat agt tat aat  cta ctc cct gag caa  gaa ctt ttt att tgt  aat      5217
Asp Ser Tyr Asn  Leu Leu Pro Glu Gln  Glu Leu Phe Ile Cys  Asn
            1005                 1010                 1015

gct gta ata gat  aat atg aat att tat  agg agt caa ttt aac  aaa      5262
Ala Val Ile Asp  Asn Met Asn Ile Tyr  Arg Ser Gln Phe Asn  Lys
            1020                 1025                 1030

tgt cta cga aaa  tac gat tta tca gaa  ata act gat ata tac  cca      5307
Cys Leu Arg Lys  Tyr Asp Leu Ser Glu  Ile Thr Asp Ile Tyr  Pro
            1035                 1040                 1045

aat aaa att ata  ttg caa gga att aag  ttc gat aag aaa aaa  aat      5352
Asn Lys Ile Ile  Leu Gln Gly Ile Lys  Phe Asp Lys Lys Lys  Asn
            1050                 1055                 1060

gtt tat gga aaa  gat ctt gtt agt ata  ata atg tca gta ttc  aat      5397
Val Tyr Gly Lys  Asp Leu Val Ser Ile  Ile Met Ser Val Phe  Asn
            1065                 1070                 1075

tca gaa gat act  att gca tac tca tta  cat tca ttg ttg aat  caa      5442
Ser Glu Asp Thr  Ile Ala Tyr Ser Leu  His Ser Leu Leu Asn  Gln
            1080                 1085                 1090

aca tat gaa aat  att gaa att ctc gtg  tgc gat gat tgt tca  tcg      5487
Thr Tyr Glu Asn  Ile Glu Ile Leu Val  Cys Asp Asp Cys Ser  Ser
            1095                 1100                 1105

gac aaa agc ctt  gaa ata att aag agc  ata gct tat tct gat  tca      5532
Asp Lys Ser Leu  Glu Ile Ile Lys Ser  Ile Ala Tyr Ser Asp  Ser
            1110                 1115                 1120

aga gtg aaa gta  tat agc tca cga aaa  aac caa ggc cct tat  aat      5577
Arg Val Lys Val  Tyr Ser Ser Arg Lys  Asn Gln Gly Pro Tyr  Asn
            1125                 1130                 1135
```

```
ata aga aat gag  cta ata aaa aaa gca  cac ggt aat ttc atc  acc      5622
Ile Arg Asn Glu  Leu Ile Lys Lys Ala  His Gly Asn Phe Ile  Thr
            1140                 1145                 1150

ttt caa gat gca  gat gat ctt tct cat  ccg gag aga ata caa  aga      5667
Phe Gln Asp Ala  Asp Asp Leu Ser His  Pro Glu Arg Ile Gln  Arg
            1155                 1160                 1165

caa gtt gag gtt  ctt cgc aat aat aag  gct gta atc tgt atg  gct      5712
Gln Val Glu Val  Leu Arg Asn Asn Lys  Ala Val Ile Cys Met  Ala
            1170                 1175                 1180

aac tgg atc cgt  gtt gcg tca aat gga  aaa att caa ttc ttc  tat      5757
Asn Trp Ile Arg  Val Ala Ser Asn Gly  Lys Ile Gln Phe Phe  Tyr
            1185                 1190                 1195

gat gat aaa gcc  aca aga atg tct gtt  gta tcg tca atg ata  aaa      5802
Asp Asp Lys Ala  Thr Arg Met Ser Val  Val Ser Ser Met Ile  Lys
            1200                 1205                 1210

aaa gat att ttt  gcg aca gtt ggt ggc  tat aga caa tct tta  att      5847
Lys Asp Ile Phe  Ala Thr Val Gly Gly  Tyr Arg Gln Ser Leu  Ile
            1215                 1220                 1225

ggt gca gat acg  gag ttt tat gaa aca  gta ata atg cgt tat  ggg      5892
Gly Ala Asp Thr  Glu Phe Tyr Glu Thr  Val Ile Met Arg Tyr  Gly
            1230                 1235                 1240

cga gaa agt att  gta aga tta ctg cag  cca ttg ata ttg ggg  tta      5937
Arg Glu Ser Ile  Val Arg Leu Leu Gln  Pro Leu Ile Leu Gly  Leu
            1245                 1250                 1255

tgg gga gac tcc  gga ctt acc agg aat  aaa gga aca gaa gct  cta      5982
Trp Gly Asp Ser  Gly Leu Thr Arg Asn  Lys Gly Thr Glu Ala  Leu
            1260                 1265                 1270

cct gat gga tat  ata tca caa tct cga  aga gaa tat agt gat  atc      6027
Pro Asp Gly Tyr  Ile Ser Gln Ser Arg  Arg Glu Tyr Ser Asp  Ile
            1275                 1280                 1285

gcg gca aga caa  cga gtg tta ggg aaa  agt atc gta agt gat  aaa      6072
Ala Ala Arg Gln  Arg Val Leu Gly Lys  Ser Ile Val Ser Asp  Lys
            1290                 1295                 1300

gat gta cgt ggt  tta tta tct cgc tat  ggt ttg ttt aaa gat  gta      6117
Asp Val Arg Gly  Leu Leu Ser Arg Tyr  Gly Leu Phe Lys Asp  Val
            1305                 1310                 1315

tca gga ata att  gaa caa tag tttgttattc tatatatatt aaatttttgg       6168
Ser Gly Ile Ile  Glu Gln
            1320

ggctatataa a atg ttc gga  aca cta aaa ata act  gtt tca ggc gct      6215
             Met Phe Gly  Thr Leu Lys Ile Thr  Val Ser Gly Ala
                     1325                 1330

ggt  tac gtt ggg ctt tca  aat gga att cta atg  gct caa aat cat      6260
Gly  Tyr Val Gly Leu Ser  Asn Gly Ile Leu Met  Ala Gln Asn His
1335                 1340                 1345

gaa  gtg gtt gca ttt gat  acc cat caa aaa aaa  gtt gac tta ctt      6305
Glu  Val Val Ala Phe Asp  Thr His Gln Lys Lys  Val Asp Leu Leu
1350                 1355                 1360

aat  gat aaa ctc tct cct  ata gag gat aag gaa  att gaa aat tat      6350
Asn  Asp Lys Leu Ser Pro  Ile Glu Asp Lys Glu  Ile Glu Asn Tyr
1365                 1370                 1375

ctt  tca act aaa ata ctt  aat ttt cgc gca act  act aac aaa tat      6395
Leu  Ser Thr Lys Ile Leu  Asn Phe Arg Ala Thr  Thr Asn Lys Tyr
1380                 1385                 1390

gaa  gcc tat aaa aat gcc  aat tac gtt att att  gct aca cca acg      6440
Glu  Ala Tyr Lys Asn Ala  Asn Tyr Val Ile Ile  Ala Thr Pro Thr
1395                 1400                 1405

aat  tat gac cca ggt tca  aat tac ttt gat aca  tca agc gtt gaa      6485
Asn  Tyr Asp Pro Gly Ser  Asn Tyr Phe Asp Thr  Ser Ser Val Glu
```

```
1410                1415                1420

gct  gtc att cgt gac gta  acg gaa atc aac cca  aac gca att atg      6530
Ala  Val Ile Arg Asp Val  Thr Glu Ile Asn Pro  Asn Ala Ile Met
1425                1430                1435

gtg  gtt aaa tct acg gtc  cca gta ggt ttc aca  aaa aca att aaa      6575
Val  Val Lys Ser Thr Val  Pro Val Gly Phe Thr  Lys Thr Ile Lys
1440                1445                1450

gaa  cat tta ggt att aat  aat att atc ttc tct  cca gaa ttt tta      6620
Glu  His Leu Gly Ile Asn  Asn Ile Ile Phe Ser  Pro Glu Phe Leu
1455                1460                1465

cga  gaa gga aga gcc cta  tac gat aat ctc cat  cca tct cgc att      6665
Arg  Glu Gly Arg Ala Leu  Tyr Asp Asn Leu His  Pro Ser Arg Ile
1470                1475                1480

att  atc ggt gaa tgt tct  gaa cgg gca gaa cgt  ttg gca gtg tta      6710
Ile  Ile Gly Glu Cys Ser  Glu Arg Ala Glu Arg  Leu Ala Val Leu
1485                1490                1495

ttt  cag gaa gga gcg att  aaa caa aat ata ccc  gtt tta ttt aca      6755
Phe  Gln Glu Gly Ala Ile  Lys Gln Asn Ile Pro  Val Leu Phe Thr
1500                1505                1510

gat  tct acg gaa gcg gaa  gcg att aag tta ttt  tca aat act tat      6800
Asp  Ser Thr Glu Ala Glu  Ala Ile Lys Leu Phe  Ser Asn Thr Tyr
1515                1520                1525

ttg  gct atg cga gtt gca  ttt ttt aat gaa ttg  gat agt tac gca      6845
Leu  Ala Met Arg Val Ala  Phe Phe Asn Glu Leu  Asp Ser Tyr Ala
1530                1535                1540

gaa  agt ttt ggt ctg aat  acg cgt cag att att  gac ggt gtt tgt      6890
Glu  Ser Phe Gly Leu Asn  Thr Arg Gln Ile Ile  Asp Gly Val Cys
1545                1550                1555

ttg  gat ccg cgc att ggt  aat tac tac aat aat  cct tct ttt ggt      6935
Leu  Asp Pro Arg Ile Gly  Asn Tyr Tyr Asn Asn  Pro Ser Phe Gly
1560                1565                1570

tat  ggt ggc tac tgt ttg  cca aaa gat acc aag  caa tta tta gcc      6980
Tyr  Gly Gly Tyr Cys Leu  Pro Lys Asp Thr Lys  Gln Leu Leu Ala
1575                1580                1585

aac  tat cag tct gtt ccg  aat aaa ctt ata tct  gca att gtt gat      7025
Asn  Tyr Gln Ser Val Pro  Asn Lys Leu Ile Ser  Ala Ile Val Asp
1590                1595                1600

gct  aac cgt aca cgt aag  gac ttt atc act aat  gtt att ttg aaa      7070
Ala  Asn Arg Thr Arg Lys  Asp Phe Ile Thr Asn  Val Ile Leu Lys
1605                1610                1615

cat  aga cca caa gtt gtg  ggg gtt tat cgt ttg  att atg aaa agt      7115
His  Arg Pro Gln Val Val  Gly Val Tyr Arg Leu  Ile Met Lys Ser
1620                1625                1630

ggt  tca gat aat ttt aga  gat tct tct att ctt  ggt att ata aag      7160
Gly  Ser Asp Asn Phe Arg  Asp Ser Ser Ile Leu  Gly Ile Ile Lys
1635                1640                1645

cgt  atc aag aaa aaa ggc  gtg aaa gta att att  tat gag ccg ctt      7205
Arg  Ile Lys Lys Lys Gly  Val Lys Val Ile Ile  Tyr Glu Pro Leu
1650                1655                1660

att  tct gga gat aca ttc  ttt aac tca cct ttg  gaa cgg gag ctg      7250
Ile  Ser Gly Asp Thr Phe  Phe Asn Ser Pro Leu  Glu Arg Glu Leu
1665                1670                1675

gcg  atc ttt aaa ggg aaa  gct gat att att atc  act aac cga atg      7295
Ala  Ile Phe Lys Gly Lys  Ala Asp Ile Ile Ile  Thr Asn Arg Met
1680                1685                1690

tca  gag gag ttg aac gat  gtg gtc gac aaa gtc  tat agt cgc gat      7340
Ser  Glu Glu Leu Asn Asp  Val Val Asp Lys Val  Tyr Ser Arg Asp
1695                1700                1705

ttg  ttt aaa tgt gac taa tgtattgtta tatactatta actattaaga           7388
```

```
Leu  Phe Lys Cys Asp
1710

gaaggaaatg cattatttaa tccgttaaaa atatgcctcg ttggtatgtt ctttattaat   7448

cctcgatcgt aaaataaga                                                7467


<210> SEQ ID NO 2
<211> LENGTH: 238
<212> TYPE: PRT
<213> ORGANISM: Escherichia coli

<400> SEQUENCE: 2

Met Ile Val Ala Asn Met Ser Ser Tyr Pro Pro Arg Lys Lys Glu Leu
1               5                   10                  15

Val His Ser Ile Gln Ser Leu His Ala Gln Val Asp Lys Ile Asn Leu
            20                  25                  30

Cys Leu Asn Glu Phe Glu Glu Ile Pro Glu Glu Leu Asp Gly Phe Ser
        35                  40                  45

Lys Leu Asn Pro Val Ile Pro Asp Lys Asp Tyr Lys Asp Val Gly Lys
    50                  55                  60

Phe Ile Phe Pro Cys Ala Lys Asn Asp Met Ile Val Leu Thr Asp Asp
65                  70                  75                  80

Asp Ile Ile Tyr Pro Pro Asp Tyr Val Glu Lys Met Leu Asn Phe Tyr
                85                  90                  95

Asn Ser Phe Ala Ile Phe Asn Cys Ile Val Gly Ile His Gly Cys Ile
            100                 105                 110

Tyr Ile Asp Ala Phe Asp Gly Asp Gln Ser Lys Arg Lys Val Phe Ser
        115                 120                 125

Phe Thr Gln Gly Leu Leu Arg Pro Arg Val Val Asn Gln Leu Gly Thr
    130                 135                 140

Gly Thr Val Phe Leu Lys Ala Asp Gln Leu Pro Ser Leu Lys Tyr Met
145                 150                 155                 160

Asp Gly Ser Gln Arg Phe Val Asp Val Arg Phe Ser Arg Tyr Met Leu
                165                 170                 175

Glu Asn Glu Ile Gly Met Ile Cys Val Pro Arg Glu Lys Asn Trp Leu
            180                 185                 190

Arg Glu Val Ser Ser Gly Ser Met Glu Gly Leu Trp Asn Thr Phe Thr
        195                 200                 205

Lys Lys Trp Pro Leu Asp Ile Ile Lys Glu Thr Gln Ala Ile Ala Gly
    210                 215                 220

Tyr Ser Lys Leu Asn Leu Glu Leu Val Tyr Asn Val Glu Gly
225                 230                 235


<210> SEQ ID NO 3
<211> LENGTH: 563
<212> TYPE: PRT
<213> ORGANISM: Escherichia coli

<400> SEQUENCE: 3

Met Met Asn Lys Leu Val Leu Val Gly His Pro Gly Ser Lys Tyr Gln
1               5                   10                  15

Ile Val Glu His Phe Leu Lys Glu Ile Gly Met Asn Ser Pro Asn Tyr
            20                  25                  30

Ser Thr Ser Asn Lys Ile Ser Pro Glu Tyr Ile Thr Ala Ser Leu Cys
        35                  40                  45

Gln Phe Tyr Gln Thr Pro Glu Val Asn Asp Val Val Asp Glu Arg Glu
    50                  55                  60
```

-continued

```
Phe Ser Ala Val Gln Val Ser Thr Met Trp Asp Ser Met Val Leu Glu
65                  70                  75                  80

Leu Met Met Asn Asn Leu Asn Asn Lys Leu Trp Gly Trp Ala Asp Pro
                85                  90                  95

Ser Ile Ile Phe Phe Leu Asp Phe Trp Lys Asn Ile Asp Lys Ser Ile
            100                 105                 110

Lys Phe Ile Met Ile Tyr Asp His Pro Lys Tyr Asn Leu Met Arg Ser
        115                 120                 125

Val Asn Asn Ala Pro Leu Ser Leu Asn Ile Asn Asn Ser Val Asp Asn
    130                 135                 140

Trp Ile Ala Tyr Asn Lys Arg Leu Leu Asp Phe Phe Leu Glu Asn Lys
145                 150                 155                 160

Glu Arg Cys Val Leu Ile Asn Phe Glu Ala Phe Gln Ser Asn Lys Lys
                165                 170                 175

Asn Ile Ile Lys Pro Leu Ser Asn Ile Ile Lys Ile Asp Asn Leu Met
            180                 185                 190

Ser Ala His Tyr Lys Asn Ser Ile Leu Phe Asp Val Val Glu Asn Asn
        195                 200                 205

Asp Tyr Thr Lys Ser Asn Glu Ile Ala Leu Leu Glu Lys Tyr Thr Thr
    210                 215                 220

Leu Phe Ser Leu Ser Ala Asn Glu Thr Glu Ile Thr Phe Asn Asp Thr
225                 230                 235                 240

Lys Val Ser Glu Tyr Leu Val Ser Glu Leu Ile Lys Glu Arg Thr Glu
                245                 250                 255

Val Leu Lys Leu Tyr Asn Glu Leu Gln Ala Tyr Ala Asn Leu Pro Tyr
            260                 265                 270

Ile Glu Thr Ser Lys Asp Asn Val Ser Ala Glu Ala Ala Leu Trp Glu
        275                 280                 285

Val Val Glu Glu Arg Asn Ser Ile Phe Asn Ile Val Ser His Leu Val
    290                 295                 300

Gln Glu Ser Lys Lys Lys Asp Ala Asp Ile Glu Leu Thr Lys Ser Ile
305                 310                 315                 320

Phe Lys Lys Arg Gln Phe Leu Leu Leu Asn Arg Ile Asn Glu Leu Lys
                325                 330                 335

Lys Glu Lys Glu Glu Val Ile Lys Leu Ser Lys Ile Asn His Asn Asp
            340                 345                 350

Val Val Arg Gln Glu Lys Tyr Pro Asp Asp Ile Glu Lys Lys Ile Asn
        355                 360                 365

Asp Ile Gln Lys Tyr Glu Glu Ile Ser Glu Lys Glu Ser Lys Leu
    370                 375                 380

Thr Gln Ala Ile Ser Glu Lys Glu Gln Ile Leu Lys Gln Leu His Lys
385                 390                 395                 400

Tyr Glu Glu Glu Ile Ser Glu Lys Glu Ser Lys Leu Thr Gln Ala Ile
                405                 410                 415

Ser Glu Lys Glu Gln Ile Leu Lys Gln Leu His Ile Val Gln Glu Gln
            420                 425                 430

Leu Glu His Tyr Phe Ile Glu Asn Gln Glu Ile Lys Lys Lys Leu Pro
        435                 440                 445

Pro Val Leu Tyr Gly Ala Ala Glu Gln Ile Lys Gln Glu Leu Gly Tyr
    450                 455                 460

Arg Leu Gly Tyr Ile Ile Val Ser Tyr Ser Lys Ser Leu Lys Gly Ile
465                 470                 475                 480
```

```
Ile Thr Met Pro Phe Ala Leu Ile Arg Glu Cys Val Phe Glu Lys Lys
                485                 490                 495

Arg Lys Lys Ser Tyr Gly Val Asp Val Pro Leu Tyr Leu Tyr Ala Asp
            500                 505                 510

Ala Asp Lys Ala Glu Arg Val Lys Lys His Leu Ser Tyr Gln Leu Gly
        515                 520                 525

Gln Ala Ile Ile Ser Ser Ala Asn Ser Ile Phe Gly Phe Ile Thr Leu
    530                 535                 540

Pro Phe Lys Leu Ile Val Val Val Tyr Lys Tyr Arg Arg Ala Lys Ile
545                 550                 555                 560

Lys Gly Cys


<210> SEQ ID NO 4
<211> LENGTH: 520
<212> TYPE: PRT
<213> ORGANISM: Escherichia coli

<400> SEQUENCE: 4

Met Asn Ala Glu Tyr Ile Asn Leu Val Glu Arg Lys Lys Lys Leu Gly
1               5                   10                  15

Thr Asn Ile Gly Ala Leu Asp Phe Leu Leu Ser Ile His Lys Glu Lys
            20                  25                  30

Val Asp Leu Gln His Lys Asn Ser Pro Leu Lys Gly Asn Asp Asn Leu
        35                  40                  45

Ile His Lys Arg Ile Asn Glu Tyr Asp Asn Val Leu Glu Leu Ser Lys
    50                  55                  60

Asn Val Ser Ala Gln Asn Ser Gly Asn Glu Phe Ser Tyr Leu Leu Gly
65                  70                  75                  80

Tyr Ala Asp Ser Leu Arg Lys Val Gly Met Leu Asp Thr Tyr Ile Lys
                85                  90                  95

Ile Val Cys Tyr Leu Thr Ile Gln Ser Arg Tyr Phe Lys Asn Gly Glu
            100                 105                 110

Arg Val Lys Leu Phe Glu His Ile Ser Asn Ala Leu Arg Tyr Ser Arg
        115                 120                 125

Ser Asp Phe Leu Ile Asn Leu Ile Phe Glu Arg Tyr Ile Glu Tyr Ile
    130                 135                 140

Asn His Leu Lys Leu Ser Pro Lys Gln Lys Asp Phe Tyr Phe Cys Thr
145                 150                 155                 160

Lys Phe Ser Lys Phe His Asp Tyr Thr Lys Asn Gly Tyr Lys Tyr Leu
                165                 170                 175

Ala Phe Asp Asn Gln Ala Asp Ala Gly Tyr Gly Leu Thr Leu Leu Leu
            180                 185                 190

Asn Ala Asn Asp Asp Met Gln Asp Ser Tyr Asn Leu Leu Pro Glu Gln
        195                 200                 205

Glu Leu Phe Ile Cys Asn Ala Val Ile Asp Asn Met Asn Ile Tyr Arg
    210                 215                 220

Ser Gln Phe Asn Lys Cys Leu Arg Lys Tyr Asp Leu Ser Glu Ile Thr
225                 230                 235                 240

Asp Ile Tyr Pro Asn Lys Ile Ile Leu Gln Gly Ile Lys Phe Asp Lys
                245                 250                 255

Lys Lys Asn Val Tyr Gly Lys Asp Leu Val Ser Ile Ile Met Ser Val
            260                 265                 270

Phe Asn Ser Glu Asp Thr Ile Ala Tyr Ser Leu His Ser Leu Leu Asn
        275                 280                 285
```

```
Gln Thr Tyr Glu Asn Ile Glu Ile Leu Val Cys Asp Asp Cys Ser Ser
    290                 295                 300

Asp Lys Ser Leu Glu Ile Ile Lys Ser Ile Ala Tyr Ser Asp Ser Arg
305                 310                 315                 320

Val Lys Val Tyr Ser Ser Arg Lys Asn Gln Gly Pro Tyr Asn Ile Arg
                325                 330                 335

Asn Glu Leu Ile Lys Lys Ala His Gly Asn Phe Ile Thr Phe Gln Asp
            340                 345                 350

Ala Asp Asp Leu Ser His Pro Glu Arg Ile Gln Arg Gln Val Glu Val
        355                 360                 365

Leu Arg Asn Asn Lys Ala Val Ile Cys Met Ala Asn Trp Ile Arg Val
    370                 375                 380

Ala Ser Asn Gly Lys Ile Gln Phe Phe Tyr Asp Asp Lys Ala Thr Arg
385                 390                 395                 400

Met Ser Val Val Ser Ser Met Ile Lys Lys Asp Ile Phe Ala Thr Val
                405                 410                 415

Gly Gly Tyr Arg Gln Ser Leu Ile Gly Ala Asp Thr Glu Phe Tyr Glu
            420                 425                 430

Thr Val Ile Met Arg Tyr Gly Arg Glu Ser Ile Val Arg Leu Leu Gln
        435                 440                 445

Pro Leu Ile Leu Gly Leu Trp Gly Asp Ser Gly Leu Thr Arg Asn Lys
    450                 455                 460

Gly Thr Glu Ala Leu Pro Asp Gly Tyr Ile Ser Gln Ser Arg Arg Glu
465                 470                 475                 480

Tyr Ser Asp Ile Ala Ala Arg Gln Arg Val Leu Gly Lys Ser Ile Val
                485                 490                 495

Ser Asp Lys Asp Val Arg Gly Leu Leu Ser Arg Tyr Gly Leu Phe Lys
            500                 505                 510

Asp Val Ser Gly Ile Ile Glu Gln
        515                 520


<210> SEQ ID NO 5
<211> LENGTH: 392
<212> TYPE: PRT
<213> ORGANISM: Escherichia coli

<400> SEQUENCE: 5

Met Phe Gly Thr Leu Lys Ile Thr Val Ser Gly Ala Gly Tyr Val Gly
1               5                   10                  15

Leu Ser Asn Gly Ile Leu Met Ala Gln Asn His Glu Val Val Ala Phe
            20                  25                  30

Asp Thr His Gln Lys Lys Val Asp Leu Leu Asn Asp Lys Leu Ser Pro
        35                  40                  45

Ile Glu Asp Lys Glu Ile Glu Asn Tyr Leu Ser Thr Lys Ile Leu Asn
    50                  55                  60

Phe Arg Ala Thr Thr Asn Lys Tyr Glu Ala Tyr Lys Asn Ala Asn Tyr
65                  70                  75                  80

Val Ile Ile Ala Thr Pro Thr Asn Tyr Asp Pro Gly Ser Asn Tyr Phe
                85                  90                  95

Asp Thr Ser Ser Val Glu Ala Val Ile Arg Asp Val Thr Glu Ile Asn
            100                 105                 110

Pro Asn Ala Ile Met Val Val Lys Ser Thr Val Pro Val Gly Phe Thr
        115                 120                 125

Lys Thr Ile Lys Glu His Leu Gly Ile Asn Asn Ile Ile Phe Ser Pro
    130                 135                 140
```

```
Glu Phe Leu Arg Glu Gly Arg Ala Leu Tyr Asp Asn Leu His Pro Ser
145                 150                 155                 160

Arg Ile Ile Ile Gly Glu Cys Ser Glu Arg Ala Glu Arg Leu Ala Val
                165                 170                 175

Leu Phe Gln Glu Gly Ala Ile Lys Gln Asn Ile Pro Val Leu Phe Thr
            180                 185                 190

Asp Ser Thr Glu Ala Glu Ala Ile Lys Leu Phe Ser Asn Thr Tyr Leu
        195                 200                 205

Ala Met Arg Val Ala Phe Phe Asn Glu Leu Asp Ser Tyr Ala Glu Ser
    210                 215                 220

Phe Gly Leu Asn Thr Arg Gln Ile Ile Asp Gly Val Cys Leu Asp Pro
225                 230                 235                 240

Arg Ile Gly Asn Tyr Tyr Asn Asn Pro Ser Phe Gly Tyr Gly Gly Tyr
                245                 250                 255

Cys Leu Pro Lys Asp Thr Lys Gln Leu Leu Ala Asn Tyr Gln Ser Val
            260                 265                 270

Pro Asn Lys Leu Ile Ser Ala Ile Val Asp Ala Asn Arg Thr Arg Lys
        275                 280                 285

Asp Phe Ile Thr Asn Val Ile Leu Lys His Arg Pro Gln Val Val Gly
    290                 295                 300

Val Tyr Arg Leu Ile Met Lys Ser Gly Ser Asp Asn Phe Arg Asp Ser
305                 310                 315                 320

Ser Ile Leu Gly Ile Ile Lys Arg Ile Lys Lys Lys Gly Val Lys Val
                325                 330                 335

Ile Ile Tyr Glu Pro Leu Ile Ser Gly Asp Thr Phe Phe Asn Ser Pro
            340                 345                 350

Leu Glu Arg Glu Leu Ala Ile Phe Lys Gly Lys Ala Asp Ile Ile Ile
        355                 360                 365

Thr Asn Arg Met Ser Glu Glu Leu Asn Asp Val Val Asp Lys Val Tyr
    370                 375                 380

Ser Arg Asp Leu Phe Lys Cys Asp
385                 390
```

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6

```
agctgagtcg acccccagga aaaattggtt aataac                          36
```

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7

```
agctgagcat gcttccaact gcgctaatga cgc                             33
```

<210> SEQ ID NO 8
<211> LENGTH: 313
<212> TYPE: DNA
<213> ORGANISM: Artificial Sequence
<220> FEATURE:

<223> OTHER INFORMATION: promoter

<400> SEQUENCE: 8

```
gcatgcttcc aactgcgcta atgacgcagc tggacgaagg cgggattctc gtcttacccg     60

taggggagga gcaccagtat ttgaaacggg tgcgtcgtcg gggaggcgaa tttattatcg    120

ataccgtgga ggccgtgcgc tttgtccctt tagtgaaggg tgagctggct taaaacgtga    180

ggaaatacct ggatttttcc tggttatttt gccgcaggtc agcgtatcgt gaacatcttt    240

tccagtgttc agtagggtgc cttgcacggt aattatgtca ctggttatta accaattttt    300

cctgggggtc gac                                                       313
```

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9

```
agctgatcta gaaaacagaa tttgcctggc ggc                                  33
```

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10

```
agctgaggat ccaggaagag tttgtagaaa cgc                                  33
```

<210> SEQ ID NO 11
<211> LENGTH: 369
<212> TYPE: DNA
<213> ORGANISM: Artificial Sequence
<220> FEATURE:
<223> OTHER INFORMATION: terminator

<400> SEQUENCE: 11

```
tctagaaaca gaatttgcct ggcggcagta gcgcggtggt cccacctgac cccatgccga     60

actcagaagt gaaacgccgt agcgccgatg gtagtgtggg gtctccccat gcgagagtag    120

ggaactgcca ggcatcaaat aaaacgaaag gctcagtcga aagactgggc ctttcgtttt    180

atctgttgtt tgtcggtgaa cgctctcctg agtaggacaa atccgccggg agcggatttg    240

aacgttgcga agcaacggcc cggagggtgg cgggcaggac gcccgccata aactgccagg    300

catcaaatta agcagaaggc catcctgacg gatggccttt ttgcgtttct acaaactctt    360

cctggatcc                                                            369
```

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12

```
ttcctggggg tcgacatgac tacgaaaatt tttaa                                35
```

<210> SEQ ID NO 13
<211> LENGTH: 35

<212> TYPE: DNA
<213> ORGANISM: Artificial Sequence
<220> FEATURE:
<223> OTHER INFORMATION: primer

<400> SEQUENCE: 13
attctgtttt ctagactaag gaaccaacac aagct 35

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
gtcgaccccc aggaaaaatt ggttaataac 30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
tctagaaaac agaatttgcc tggcggcagt 30

<210> SEQ ID NO 16
<211> LENGTH: 1980
<212> TYPE: DNA
<213> ORGANISM: Flavobacterium heparinum

<400> SEQUENCE: 16
atgactacga aaatttttaa aaggatcatt gtatttgctg taattgccct atcgtcggga 60
aatatacttg cacaaagctc ttccattacc aggaaagatt ttgaccacat caaccttgag 120
tattccggac tggaaaaggt taataaagca gttgctgccg gcaactatga cgatgcggcc 180
aaagcattac tggcatacta cagggaaaaa agtaaggcca gggaacctga tttcagtaat 240
gcagaaaagc ctgccgatat acgccagccc atagataagg ttacgcgtga aatggccgac 300
aaggctttgg tccaccagtt tcaaccgcac aaaggctacg gctattttga ttatggtaaa 360
gacatcaact ggcagatgtg gccggtaaaa gacaatgaag tacgctggca gttgcaccgt 420
gtaaaatggt ggcaggctat ggccctggtt tatcacgcta cgggcgatga aaaatatgca 480
agagaatggg tatatcagta cagcgattgg gccagaaaaa acccattggg cctgtcgcag 540
gataatgata aatttgtgtg gcggcccctt gaagtgtcgg acagggtaca aagtcttccc 600
ccaaccttca gcttatttgt aaactcgcca gcctttaccc cagccttttt aatggaattt 660
ttaaacagtt accaccaaca ggccgattat ttatctacgc attatgccga acagggaaac 720
caccgtttat ttgaagccca acgcaacttg tttgcagggg tatctttccc tgaatttaaa 780
gattcaccaa gatggaggca aaccggcata tcggtgctga acaccgagat caaaaaacag 840
gtttatgccg atgggatgca gtttgaactt tcaccaattt accatgtagc tgccatcgat 900
atcttcttaa aggcctatgg ttctgcaaaa cgagttaacc ttgaaaaaga atttccgcaa 960
tcttatgtac aaactgtaga aaatatgatt atggcgctga tcagtatttc actgccagat 1020
tataacaccc ctatgtttgg agattcatgg attacagata aaaatttcag gatggcacag 1080
tttgccagct gggcccgggt tttcccggca aaccaggcca taaaatattt tgctacagat 1140

```
ggcaaacaag gtaaggcgcc taacttttta tccaaagcat tgagcaatgc aggcttttat   1200

acgtttagaa gcggatggga taaaaatgca accgttatgg tattaaaagc cagtcctccc   1260

ggagaatttc atgcccagcc ggataacggg acttttgaac tttttataaa gggcagaaac   1320

tttaccccag acgccggggt atttgtgtat agcggcgacg aagccatcat gaaactgcgg   1380

aactggtacc gtcaaacccg catacacagc acgcttacac tcgacaatca aaatatggtc   1440

attaccaaag cccggcaaaa caaatgggaa acaggaaata accttgatgt gcttacctat   1500

accaacccaa gctatccgaa tctggaccat cagcgcagtg tacttttcat caacaaaaaa   1560

tactttctgg tcatcgatag ggcaataggc gaagctaccg gaaacctggg cgtacactgg   1620

cagcttaaag aagacagcaa ccctgttttc gataagacaa agaaccgggt ttacaccact   1680

tacagagatg gtaacaacct gatgatccaa tcgttgaatg cggacaggac cagcctcaat   1740

gaagaagaag gaaaggtatc ttatgtttac aataaggagc tgaaaagacc tgctttcgta   1800

tttgaaaagc ctaaaaagaa tgccggcaca caaaatttg tcagtatagt ttatccatac   1860

gacggccaga aggctccaga gatcagcata cgggaaaaca agggcaatga ttttgagaaa   1920

ggcaagctta atctaaccct taccattaac ggaaaacaac agcttgtgtt ggttccttag   1980
```

```
<210> SEQ ID NO 17
<211> LENGTH: 659
<212> TYPE: PRT
<213> ORGANISM: Flavobacterium heparinum

<400> SEQUENCE: 17

Met Thr Thr Lys Ile Phe Lys Arg Ile Ile Val Phe Ala Val Ile Ala
1               5                   10                  15

Leu Ser Ser Gly Asn Ile Leu Ala Gln Ser Ser Ser Ile Thr Arg Lys
            20                  25                  30

Asp Phe Asp His Ile Asn Leu Glu Tyr Ser Gly Leu Glu Lys Val Asn
        35                  40                  45

Lys Ala Val Ala Ala Gly Asn Tyr Asp Asp Ala Ala Lys Ala Leu Leu
    50                  55                  60

Ala Tyr Tyr Arg Glu Lys Ser Lys Ala Arg Glu Pro Asp Phe Ser Asn
65                  70                  75                  80

Ala Glu Lys Pro Ala Asp Ile Arg Gln Pro Ile Asp Lys Val Thr Arg
                85                  90                  95

Glu Met Ala Asp Lys Ala Leu Val His Gln Phe Gln Pro His Lys Gly
            100                 105                 110

Tyr Gly Tyr Phe Asp Tyr Gly Lys Asp Ile Asn Trp Gln Met Trp Pro
        115                 120                 125

Val Lys Asp Asn Glu Val Arg Trp Gln Leu His Arg Val Lys Trp Trp
    130                 135                 140

Gln Ala Met Ala Leu Val Tyr His Ala Thr Gly Asp Glu Lys Tyr Ala
145                 150                 155                 160

Arg Glu Trp Val Tyr Gln Tyr Ser Asp Trp Ala Arg Lys Asn Pro Leu
                165                 170                 175

Gly Leu Ser Gln Asp Asn Asp Lys Phe Val Trp Arg Pro Leu Glu Val
            180                 185                 190

Ser Asp Arg Val Gln Ser Leu Pro Pro Thr Phe Ser Leu Phe Val Asn
        195                 200                 205

Ser Pro Ala Phe Thr Pro Ala Phe Leu Met Glu Phe Leu Asn Ser Tyr
    210                 215                 220

His Gln Gln Ala Asp Tyr Leu Ser Thr His Tyr Ala Glu Gln Gly Asn
```

```
225                 230                 235                 240

His Arg Leu Phe Glu Ala Gln Arg Asn Leu Phe Ala Gly Val Ser Phe
                245                 250                 255

Pro Glu Phe Lys Asp Ser Pro Arg Trp Arg Gln Thr Gly Ile Ser Val
            260                 265                 270

Leu Asn Thr Glu Ile Lys Lys Gln Val Tyr Ala Asp Gly Met Gln Phe
        275                 280                 285

Glu Leu Ser Pro Ile Tyr His Val Ala Ala Ile Asp Ile Phe Leu Lys
    290                 295                 300

Ala Tyr Gly Ser Ala Lys Arg Val Asn Leu Glu Lys Glu Phe Pro Gln
305                 310                 315                 320

Ser Tyr Val Gln Thr Val Glu Asn Met Ile Met Ala Leu Ile Ser Ile
                325                 330                 335

Ser Leu Pro Asp Tyr Asn Thr Pro Met Phe Gly Asp Ser Trp Ile Thr
            340                 345                 350

Asp Lys Asn Phe Arg Met Ala Gln Phe Ala Ser Trp Ala Arg Val Phe
        355                 360                 365

Pro Ala Asn Gln Ala Ile Lys Tyr Phe Ala Thr Asp Gly Lys Gln Gly
    370                 375                 380

Lys Ala Pro Asn Phe Leu Ser Lys Ala Leu Ser Asn Ala Gly Phe Tyr
385                 390                 395                 400

Thr Phe Arg Ser Gly Trp Asp Lys Asn Ala Thr Val Met Val Leu Lys
                405                 410                 415

Ala Ser Pro Pro Gly Glu Phe His Ala Gln Pro Asp Asn Gly Thr Phe
            420                 425                 430

Glu Leu Phe Ile Lys Gly Arg Asn Phe Thr Pro Asp Ala Gly Val Phe
        435                 440                 445

Val Tyr Ser Gly Asp Glu Ala Ile Met Lys Leu Arg Asn Trp Tyr Arg
    450                 455                 460

Gln Thr Arg Ile His Ser Thr Leu Thr Leu Asp Asn Gln Asn Met Val
465                 470                 475                 480

Ile Thr Lys Ala Arg Gln Asn Lys Trp Glu Thr Gly Asn Asn Leu Asp
                485                 490                 495

Val Leu Thr Tyr Thr Asn Pro Ser Tyr Pro Asn Leu Asp His Gln Arg
            500                 505                 510

Ser Val Leu Phe Ile Asn Lys Lys Tyr Phe Leu Val Ile Asp Arg Ala
        515                 520                 525

Ile Gly Glu Ala Thr Gly Asn Leu Gly Val His Trp Gln Leu Lys Glu
    530                 535                 540

Asp Ser Asn Pro Val Phe Asp Lys Thr Lys Asn Arg Val Tyr Thr Thr
545                 550                 555                 560

Tyr Arg Asp Gly Asn Asn Leu Met Ile Gln Ser Leu Asn Ala Asp Arg
                565                 570                 575

Thr Ser Leu Asn Glu Glu Glu Gly Lys Val Ser Tyr Val Tyr Asn Lys
            580                 585                 590

Glu Leu Lys Arg Pro Ala Phe Val Phe Glu Lys Pro Lys Lys Asn Ala
        595                 600                 605

Gly Thr Gln Asn Phe Val Ser Ile Val Tyr Pro Tyr Asp Gly Gln Lys
    610                 615                 620

Ala Pro Glu Ile Ser Ile Arg Glu Asn Lys Gly Asn Asp Phe Glu Lys
625                 630                 635                 640

Gly Lys Leu Asn Leu Thr Leu Thr Ile Asn Gly Lys Gln Gln Leu Val
                645                 650                 655
```

Leu Val Pro

<210> SEQ ID NO 18
<211> LENGTH: 44
<212> TYPE: DNA
<213> ORGANISM: Artificial Sequence
<220> FEATURE:
<223> OTHER INFORMATION: primer

<400> SEQUENCE: 18
ttcagaattc ggatccaata aatgtagcag cgataaagca attc 44

<210> SEQ ID NO 19
<211> LENGTH: 44
<212> TYPE: DNA
<213> ORGANISM: Artificial Sequence
<220> FEATURE:
<223> OTHER INFORMATION: primer

<400> SEQUENCE: 19
ggccagtgcc aagcttttaa ttgtgttttg cacggctacc tttc 44

<210> SEQ ID NO 20
<211> LENGTH: 6646
<212> TYPE: DNA
<213> ORGANISM: Artificial Sequence
<220> FEATURE:
<223> OTHER INFORMATION: plasmid

<400> SEQUENCE: 20
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg taagttagct cactcattag 1200
gcacaattct catgtttgac agcttatcat cgactgcacg gtgcaccaat gcttctggcg 1260

```
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga aacagccagt ccgtttaggt gttttcacga   1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acgggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcagaattc   2700
ggatcctcta gagtcgacct gcaggcaagc ttggcactgg ccgtcgtttt acaacgtcgt   2760
gactgggaaa accctggcgt tacccaactt aatcgccttg cagcacatcc ccctttcgcc   2820
agctggcgta atagcgaaga ggcccgcacc gatcgccctt cccaacagtt gcgcagcctg   2880
aatggcgaat ggcagcttgg ctgttttggc ggatgagata agattttcag cctgatacag   2940
attaaatcag aacgcagaag cggtctgata aaacagaatt tgcctggcgg cagtagcgcg   3000
gtggtcccac ctgaccccat gccgaactca gaagtgaaac gccgtagcgc cgatggtagt   3060
gtggggtctc cccatgcgag agtagggaac tgccaggcat caaataaaac gaaaggctca   3120
gtcgaaagac tgggcctttc gttttatctg ttgtttgtcg gtgaacgctc tcctgagtag   3180
gacaaatccg ccgggagcgg atttgaacgt tgcgaagcaa cggcccggag ggtggcgggc   3240
aggacgcccg ccataaactg ccaggcatca aattaagcag aaggccatcc tgacggatgg   3300
cctttttgcg tttctacaaa ctctttttgt ttatttttct aaatacattc aaatatgtat   3360
ccgctcatga gacaataacc ctgataaatg cttcaataat attgaaaaag gaagagtatg   3420
agtattcaac atttccgtgt cgcccttatt cccttttttg cggcattttg ccttcctgtt   3480
tttgctcacc cagaaacgct ggtgaaagta aaagatgctg aagatcagtt gggtgcacga   3540
gtgggttaca tcgaactgga tctcaacagc ggtaagatcc ttgagagttt tcgccccgaa   3600
gaacgttctc caatgatgag cacttttaaa gttctgctat gtggcgcggt attatcccgt   3660
```

```
gttgacgccg ggcaagagca actcggtcgc cgcatacact attctcagaa tgacttggtt   3720
gagtactcac cagtcacaga aaagcatctt acggatggca tgacagtaag agaattatgc   3780
agtgctgcca taaccatgag tgataacact gcggccaact tacttctgac aacgatcgga   3840
ggaccgaagg agctaaccgc tttttttgcac aacatggggg atcatgtaac tcgccttgat   3900
cgttgggaac cggagctgaa tgaagccata ccaaacgacg agcgtgacac cacgatgcct   3960
gtagcaatgg caacaacgtt gcgcaaacta ttaactggcg aactacttac tctagcttcc   4020
cggcaacaat taatagactg gatggaggcg gataaagttg caggaccact tctgcgctcg   4080
gcccttccgg ctggctggtt tattgctgat aaatctggag ccggtgagcg tgggtctcgc   4140
ggtatcattg cagcactggg gccagatggt aagccctccc gtatcgtagt tatctacacg   4200
acggggagtc aggcaactat ggatgaacga aatagacaga tcgctgagat aggtgcctca   4260
ctgattaagc attggtaact gtcagaccaa gtttactcat atatacttta gattgattta   4320
ccccggttga taatcagaaa agccccaaaa acaggaagat tgtataagca aatatttaaa   4380
ttgtaaacgt taatattttg ttaaaattcg cgttaaattt ttgttaaatc agctcatttt   4440
ttaaccaata ggccgaaatc ggcaaaatcc cttataaatc aaaagaatag accgagatag   4500
ggttgagtgt tgttccagtt tggaacaaga gtccactatt aaagaacgtg gactccaacg   4560
tcaaagggcg aaaaaccgtc tatcagggcg atggcccact acgtgaacca tcacccaaat   4620
caagtttttt ggggtcgagg tgccgtaaag cactaaatcg gaaccctaaa gggagccccc   4680
gatttagagc ttgacgggga aagccggcga acgtggcgag aaaggaaggg aagaaagcga   4740
aaggagcggg cgctagggcg ctggcaagtg tagcggtcac gctgcgcgta accaccacac   4800
ccgccgcgct taatgcgccg ctacagggcg cgtaaaagga tctaggtgaa gatccttttt   4860
gataatctca tgaccaaaat cccttaacgt gagttttcgt tccactgagc gtcagacccc   4920
gtagaaaaga tcaaaggatc ttcttgagat cctttttttc tgcgcgtaat ctgctgcttg   4980
caaacaaaaa aaccaccgct accagcggtg gtttgtttgc cggatcaaga gctaccaact   5040
ctttttccga aggtaactgg cttcagcaga gcgcagatac caaatactgt ccttctagtg   5100
tagccgtagt taggccacca cttcaagaac tctgtagcac cgcctacata cctcgctctg   5160
ctaatcctgt taccagtggc tgctgccagt ggcgataagt cgtgtcttac cgggttggac   5220
tcaagacgat agttaccgga taaggcgcag cggtcgggct gaacgggggg ttcgtgcaca   5280
cagcccagct tggagcgaac gacctacacc gaactgagat acctacagcg tgagctatga   5340
gaaagcgcca cgcttcccga agggagaaag gcggacaggt atccggtaag cggcagggtc   5400
ggaacaggag agcgcacgag ggagcttcca gggggaaacg cctggtatct ttatagtcct   5460
gtcgggtttc gccacctctg acttgagcgt cgatttttgt gatgctcgtc aggggggcgg   5520
agcctatgga aaaacgccag caacgcggcc tttttacggt tcctggcctt ttgctggcct   5580
tttgctcaca tgttctttcc tgcgttatcc cctgattctg tggataaccg tattaccgcc   5640
tttgagtgag ctgataccgc tcgccgcagc cgaacgaccg agcgcagcga gtcagtgagc   5700
gaggaagcgg aagagcgcct gatgcggtat tttctcctta cgcatctgtg cggtatttca   5760
caccgcatat atggtgcact ctcagtacaa tctgctctga tgccgcatag ttaagccagt   5820
atacactccg ctatcgctac gtgactgggt catggctgcg ccccgacacc cgccaacacc   5880
cgctgacgcg ccctgacggg cttgtctgct cccggcatcc gcttacagac aagctgtgac   5940
cgtctccggg agctgcatgt gtcagaggtt ttcaccgtca tcaccgaaac gcgcgaggca   6000
```

```
gctgcggtaa agctcatcag cgtggtcgtg cagcgattca cagatgtctg cctgttcatc   6060

cgcgtccagc tcgttgagtt tctccagaag cgttaatgtc tggcttctga taaagcgggc   6120

catgttaagg gcggtttttt cctgtttggt cactgatgcc tccgtgtaag ggggatttct   6180

gttcatgggg gtaatgatac cgatgaaacg agagaggatg ctcacgatac gggttactga   6240

tgatgaacat gcccggttac tggaacgttg tgagggtaaa caactggcgg tatggatgcg   6300

gcgggaccag agaaaaatca ctcagggtca atgccagcgc ttcgttaata cagatgtagg   6360

tgttccacag ggtagccagc agcatcctgc gatgcagatc cggaacataa tggtgcaggg   6420

cgctgacttc cgcgtttcca gactttacga aacacggaaa ccgaagacca ttcatgttgt   6480

tgctcaggtc gcagacgttt tgcagcagca gtcgcttcac gttcgctcgc gtatcggtga   6540

ttcattctgc taaccagtaa ggcaaccccg ccagcctagc cgggtcctca acgacaggag   6600

cacgatcatg cgcacccgtg gccaggaccc aacgctgccc gaaatt                  6646
```

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21

```
aagcttggca ctggccgtcg ttttacaacg tcgtg                                35
```

<210> SEQ ID NO 22
<211> LENGTH: 35
<212> TYPE: DNA
<213> ORGANISM: Artificial Sequence
<220> FEATURE:
<223> OTHER INFORMATION: primer

<400> SEQUENCE: 22

```
ggatccgaat tctgaaatcc ttccctcgat cccga                                35
```

<210> SEQ ID NO 23
<211> LENGTH: 1770
<212> TYPE: DNA
<213> ORGANISM: Homo sapiens

<400> SEQUENCE: 23

```
aataaatgta gcagcgataa agcaattcag tttccgcgtc gtagcagcag cggttttcgt     60

gttgatggtt ttgaaaaacg tgcagcagcc agcgaaagca ataactatat gaatcatgtt    120

gccaaacagc agagcgaaga agcatttccg caagaacagc agaaagcacc gcctgttgtt    180

ggtggtttta atagcaatgt tggtagcaaa gttctgggcc tgaaatatga agaaattgac    240

tgcctgatca acgatgagca taccattaaa ggtcgtcgtg aaggtaatga agtttttctg    300

ccgtttacct gggtggagaa atactttgat gtttatggta aagtggtgca gtatgatggc    360

tatgatcgtt ttgaatttag ccatagctac agcaaagttt atgcacagcg tgcaccgtat    420

catcctgatg gtgtttttat gagctttgag ggctataatg ttgaagttcg tgatcgcgtt    480

aaatgcatta gcggtgttga aggtgttccg ctgagcaccc agtggggtcc gcagggttat    540

ttctatccga ttcagattgc acagtatggc ctgagccatt atagcaaaaa tctgaccgaa    600

aaaccgcctc acattgaagt ttatgaaacc gcagaagatc gcgacaaaaa caaaccgaat    660

gattggaccg ttccgaaagg ttgttttatg gcaaatgttg cagataaaag ccgcttcacc    720

aatgtgaaac agtttattgc accggaaacc agcgaaggtg ttagcctgca gctgggtaat    780
```

```
accaaagatt ttatcattag cttcgatctg aaatttctga ccaatggtag cgttagcgtt    840

gttctggaaa ccaccgaaaa aaatcagctg tttaccatcc attatgtgag caatgcccag    900

ctgattgcat ttaaagaacg cgatatctat tatggcattg gtccgcgtac cagttggagc    960

accgttaccc gtgatctggt taccgatctg cgtaaaggtg ttggtctgag caatacaaaa   1020

gcagttaaac cgaccaaaat tatgccgaaa aaagttgttc gtctgatcgc caaaggtaaa   1080

ggttttctgg ataacattac cattagcacc accgcacata tggcagcatt ttttgcagca   1140

agcgattggc tggttcgtaa ccaggatgaa aaaggtggtt ggccgattat ggttacccgt   1200

aaactgggtg aaggttttaa aagcctggaa ccgggttggt atagcgcaat ggcacagggt   1260

caggcaatta gcaccctggt tcgtgcatat ctgctgacca aagatcatat tttctgaat   1320

agcgcactgc gtgcaaccgc accgtacaaa tttctgtcag aacagcatgg tgttaaagcc   1380

gtgtttatga acaaacacga ttggtatgaa gaatatccga ccaccccgag cagctttgtt   1440

ctgaatggtt ttatgtatag cctgatcggt ctgtacgacc tgaaagaaac agccggtgaa   1500

aaactgggta aagaagcacg tagcctgtac gaacgtggta tggaaagcct gaaagcaatg   1560

ctgccgctgt atgataccgg tagcggcacc atttatgatc tgcgtcattt tatgctgggt   1620

atcgcaccga atctggcacg ttgggattat cataccaccc atattaatca gctgcaactg   1680

ctgagtacca ttgatgaaag tccggtgttt aaagaatttg tgaaacgctg gaaaagctac   1740

ctgaaaggta gccgtgcaaa acacaattaa                                    1770


<210> SEQ ID NO 24
<211> LENGTH: 589
<212> TYPE: PRT
<213> ORGANISM: Homo sapiens

<400> SEQUENCE: 24

Asn Lys Cys Ser Ser Asp Lys Ala Ile Gln Phe Pro Arg Arg Ser Ser
1               5                   10                  15

Ser Gly Phe Arg Val Asp Gly Phe Glu Lys Arg Ala Ala Ala Ser Glu
            20                  25                  30

Ser Asn Asn Tyr Met Asn His Val Ala Lys Gln Gln Ser Glu Glu Ala
        35                  40                  45

Phe Pro Gln Glu Gln Gln Lys Ala Pro Pro Val Val Gly Gly Phe Asn
    50                  55                  60

Ser Asn Val Gly Ser Lys Val Leu Gly Leu Lys Tyr Glu Glu Ile Asp
65                  70                  75                  80

Cys Leu Ile Asn Asp Glu His Thr Ile Lys Gly Arg Arg Glu Gly Asn
                85                  90                  95

Glu Val Phe Leu Pro Phe Thr Trp Val Glu Lys Tyr Phe Asp Val Tyr
            100                 105                 110

Gly Lys Val Val Gln Tyr Asp Gly Tyr Asp Arg Phe Glu Phe Ser His
        115                 120                 125

Ser Tyr Ser Lys Val Tyr Ala Gln Arg Ala Pro Tyr His Pro Asp Gly
    130                 135                 140

Val Phe Met Ser Phe Glu Gly Tyr Asn Val Glu Val Arg Asp Arg Val
145                 150                 155                 160

Lys Cys Ile Ser Gly Val Glu Gly Val Pro Leu Ser Thr Gln Trp Gly
                165                 170                 175

Pro Gln Gly Tyr Phe Tyr Pro Ile Gln Ile Ala Gln Tyr Gly Leu Ser
            180                 185                 190
```

```
His Tyr Ser Lys Asn Leu Thr Glu Lys Pro Pro His Ile Glu Val Tyr
        195                 200                 205

Glu Thr Ala Glu Asp Arg Asp Lys Asn Lys Pro Asn Asp Trp Thr Val
    210                 215                 220

Pro Lys Gly Cys Phe Met Ala Asn Val Ala Asp Lys Ser Arg Phe Thr
225                 230                 235                 240

Asn Val Lys Gln Phe Ile Ala Pro Glu Thr Ser Glu Gly Val Ser Leu
                245                 250                 255

Gln Leu Gly Asn Thr Lys Asp Phe Ile Ile Ser Phe Asp Leu Lys Phe
            260                 265                 270

Leu Thr Asn Gly Ser Val Ser Val Val Leu Glu Thr Thr Glu Lys Asn
        275                 280                 285

Gln Leu Phe Thr Ile His Tyr Val Ser Asn Ala Gln Leu Ile Ala Phe
    290                 295                 300

Lys Glu Arg Asp Ile Tyr Tyr Gly Ile Gly Pro Arg Thr Ser Trp Ser
305                 310                 315                 320

Thr Val Thr Arg Asp Leu Val Thr Asp Leu Arg Lys Gly Val Gly Leu
                325                 330                 335

Ser Asn Thr Lys Ala Val Lys Pro Thr Lys Ile Met Pro Lys Lys Val
            340                 345                 350

Val Arg Leu Ile Ala Lys Gly Lys Gly Phe Leu Asp Asn Ile Thr Ile
        355                 360                 365

Ser Thr Thr Ala His Met Ala Ala Phe Phe Ala Ala Ser Asp Trp Leu
    370                 375                 380

Val Arg Asn Gln Asp Glu Lys Gly Gly Trp Pro Ile Met Val Thr Arg
385                 390                 395                 400

Lys Leu Gly Glu Gly Phe Lys Ser Leu Glu Pro Gly Trp Tyr Ser Ala
                405                 410                 415

Met Ala Gln Gly Gln Ala Ile Ser Thr Leu Val Arg Ala Tyr Leu Leu
            420                 425                 430

Thr Lys Asp His Ile Phe Leu Asn Ser Ala Leu Arg Ala Thr Ala Pro
        435                 440                 445

Tyr Lys Phe Leu Ser Glu Gln His Gly Val Lys Ala Val Phe Met Asn
    450                 455                 460

Lys His Asp Trp Tyr Glu Glu Tyr Pro Thr Thr Pro Ser Ser Phe Val
465                 470                 475                 480

Leu Asn Gly Phe Met Tyr Ser Leu Ile Gly Leu Tyr Asp Leu Lys Glu
                485                 490                 495

Thr Ala Gly Glu Lys Leu Gly Lys Glu Ala Arg Ser Leu Tyr Glu Arg
            500                 505                 510

Gly Met Glu Ser Leu Lys Ala Met Leu Pro Leu Tyr Asp Thr Gly Ser
        515                 520                 525

Gly Thr Ile Tyr Asp Leu Arg His Phe Met Leu Gly Ile Ala Pro Asn
    530                 535                 540

Leu Ala Arg Trp Asp Tyr His Thr Thr His Ile Asn Gln Leu Gln Leu
545                 550                 555                 560

Leu Ser Thr Ile Asp Glu Ser Pro Val Phe Lys Glu Phe Val Lys Arg
                565                 570                 575

Trp Lys Ser Tyr Leu Lys Gly Ser Arg Ala Lys His Asn
            580                 585
```

<210> SEQ ID NO 25
<211> LENGTH: 36
<212> TYPE: DNA

<213> ORGANISM: Artificial Sequence
<220> FEATURE:
<223> OTHER INFORMATION: primer

<400> SEQUENCE: 25
ttcagaattc ggatcccgtg aaattgaaca gcgtca 36

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26
ggccagtgcc aagcttttaa ttgcttttcg gataga 36

<210> SEQ ID NO 27
<211> LENGTH: 918
<212> TYPE: DNA
<213> ORGANISM: Cricetulus griseus

<400> SEQUENCE: 27
cgtgaaattg aacagcgtca taccatggat ggtccgcgtc aggatgcagc agttgatgaa 60
gaagaagata tcgtcattat ctataaccgt gttccgaaaa ccgcaagcac cagctttacc 120
aatattgcaa ttgatctgtg cgccaaaaat cgctatcatg tgctgcatat caacaccacc 180
aaaaataacc cggttatgag cctgcaggat caggttcgtt ttgttaaaaa cattaccacc 240
tggaacgaaa tgaaaccggg tttttatcat ggccatatca gctatctgga ttttgcgaaa 300
tttggcgtga aaaaaaaacc gatctacatc aacgttattc gcgatccgat tgaacgtctg 360
gttagctatt attactttct gcgcttcggt gatgattatc gtccgggtct gcgtcgtcgt 420
aaacagggcg acaaaaaaac ctttgatgaa tgtgttgccg aaggtggtag cgattgtgca 480
ccggaaaaac tgtggctgca gattccgttt ttttgcggtc atagcagcga atgttggaat 540
gttggtagcc gttgggcaat ggatcaggcc aaatataacc tgatcaacga atattttctg 600
gtgggtgtga ccgaagaact ggaagatttc attatgctgc tggaagcagc actgcctcgt 660
ttttttcgtg gtgcaaccga tctgtatcgt accggtaaaa aaagccatct gcgtaaaacg 720
acggaaaaaa aactgccgac caaacagacc attgcaaaac tgcagcagag cgatatttgg 780
aaaatggaaa acgagtttta tgaatttgcc ctggaacagt ttcagtttat tcgtgcacat 840
gcagttcgtg aaaaagatgg tgatctgtat attctggccc agaacttctt ctacgaaaaa 900
atctatccga aaagcaat 918

<210> SEQ ID NO 28
<211> LENGTH: 306
<212> TYPE: PRT
<213> ORGANISM: Cricetulus griseus

<400> SEQUENCE: 28

Arg Glu Ile Glu Gln Arg His Thr Met Asp Gly Pro Arg Gln Asp Ala
1 5 10 15

Ala Val Asp Glu Glu Glu Asp Ile Val Ile Ile Tyr Asn Arg Val Pro
20 25 30

Lys Thr Ala Ser Thr Ser Phe Thr Asn Ile Ala Ile Asp Leu Cys Ala
35 40 45

Lys Asn Arg Tyr His Val Leu His Ile Asn Thr Thr Lys Asn Asn Pro
50 55 60

```
Val Met Ser Leu Gln Asp Gln Val Arg Phe Val Lys Asn Ile Thr Thr
65                  70                  75                  80

Trp Asn Glu Met Lys Pro Gly Phe Tyr His Gly His Ile Ser Tyr Leu
                85                  90                  95

Asp Phe Ala Lys Phe Gly Val Lys Lys Lys Pro Ile Tyr Ile Asn Val
            100                 105                 110

Ile Arg Asp Pro Ile Glu Arg Leu Val Ser Tyr Tyr Tyr Phe Leu Arg
        115                 120                 125

Phe Gly Asp Asp Tyr Arg Pro Gly Leu Arg Arg Arg Lys Gln Gly Asp
    130                 135                 140

Lys Lys Thr Phe Asp Glu Cys Val Ala Glu Gly Gly Ser Asp Cys Ala
145                 150                 155                 160

Pro Glu Lys Leu Trp Leu Gln Ile Pro Phe Phe Cys Gly His Ser Ser
                165                 170                 175

Glu Cys Trp Asn Val Gly Ser Arg Trp Ala Met Asp Gln Ala Lys Tyr
            180                 185                 190

Asn Leu Ile Asn Glu Tyr Phe Leu Val Gly Val Thr Glu Glu Leu Glu
        195                 200                 205

Asp Phe Ile Met Leu Leu Glu Ala Ala Leu Pro Arg Phe Phe Arg Gly
    210                 215                 220

Ala Thr Asp Leu Tyr Arg Thr Gly Lys Lys Ser His Leu Arg Lys Thr
225                 230                 235                 240

Thr Glu Lys Lys Leu Pro Thr Lys Gln Thr Ile Ala Lys Leu Gln Gln
                245                 250                 255

Ser Asp Ile Trp Lys Met Glu Asn Glu Phe Tyr Glu Phe Ala Leu Glu
            260                 265                 270

Gln Phe Gln Phe Ile Arg Ala His Ala Val Arg Glu Lys Asp Gly Asp
        275                 280                 285

Leu Tyr Ile Leu Ala Gln Asn Phe Phe Tyr Glu Lys Ile Tyr Pro Lys
    290                 295                 300

Ser Asn
305
```

<210> SEQ ID NO 29
<211> LENGTH: 311
<212> TYPE: PRT
<213> ORGANISM: Mus musculus

<400> SEQUENCE: 29

```
Met Thr Leu Leu Leu Leu Gly Ala Val Leu Leu Val Ala Gln Pro Gln
1               5                   10                  15

Leu Val His Ser His Pro Ala Ala Pro Gly Pro Gly Leu Lys Gln Gln
            20                  25                  30

Glu Leu Leu Arg Lys Val Ile Ile Leu Pro Glu Asp Thr Gly Glu Gly
        35                  40                  45

Thr Ala Ser Asn Gly Ser Thr Gln Gln Leu Pro Gln Thr Ile Ile Ile
    50                  55                  60

Gly Val Arg Lys Gly Gly Thr Arg Ala Leu Leu Glu Met Leu Ser Leu
65                  70                  75                  80

His Pro Asp Val Ala Ala Ala Glu Asn Glu Val His Phe Phe Asp Trp
                85                  90                  95

Glu Glu His Tyr Ser Gln Gly Leu Gly Trp Tyr Leu Thr Gln Met Pro
            100                 105                 110

Phe Ser Ser Pro His Gln Leu Thr Val Glu Lys Thr Pro Ala Tyr Phe
```

```
        115                 120                 125

Thr Ser Pro Lys Val Pro Glu Arg Ile His Ser Met Asn Pro Thr Ile
    130                 135                 140

Arg Leu Leu Leu Ile Leu Arg Asp Pro Ser Glu Arg Val Leu Ser Asp
145                 150                 155                 160

Tyr Thr Gln Val Leu Tyr Asn His Leu Gln Lys His Lys Pro Tyr Pro
                165                 170                 175

Pro Ile Glu Asp Leu Leu Met Arg Asp Gly Arg Leu Asn Leu Asp Tyr
            180                 185                 190

Lys Ala Leu Asn Arg Ser Leu Tyr His Ala His Met Leu Asn Trp Leu
        195                 200                 205

Arg Phe Phe Pro Leu Gly His Ile His Ile Val Asp Gly Asp Arg Leu
    210                 215                 220

Ile Arg Asp Pro Phe Pro Glu Ile Gln Lys Val Glu Arg Phe Leu Lys
225                 230                 235                 240

Leu Ser Pro Gln Ile Asn Ala Ser Asn Phe Tyr Phe Asn Lys Thr Lys
                245                 250                 255

Gly Phe Tyr Cys Leu Arg Asp Ser Gly Lys Asp Arg Cys Leu His Glu
            260                 265                 270

Ser Lys Gly Arg Ala His Pro Gln Val Asp Pro Lys Leu Leu Asp Lys
        275                 280                 285

Leu His Glu Tyr Phe His Glu Pro Asn Lys Lys Phe Phe Lys Leu Val
    290                 295                 300

Gly Arg Thr Phe Asp Trp His
305                 310
```

<210> SEQ ID NO 30
<211> LENGTH: 808
<212> TYPE: DNA
<213> ORGANISM: Artificial Sequence
<220> FEATURE:
<223> OTHER INFORMATION: 3-OST-1 gene optimized for expression of E. coli

<400> SEQUENCE: 30

```
gaattcgggc accgcaagca atggtagcac ccagcagctg ccgcagacca ttattatcgg      60

tgttcgtaaa ggtggcaccc gtgcactgct ggaaatgctg agcctgcatc ctgatgttgc     120

agcagcagaa aatgaagtgc atttttttga ttgggaggaa cattatagcc agggtctggg     180

ttggtatctg acccagatgc cgtttagcag tccgcatcag ctgaccgttg aaaaaacacc     240

ggcatatttc accagcccga aagtgccgga acgtattcat agcatgaatc cgaccattcg     300

cctgctgctg attctgcgtg atccgagcga acgtgttctg agcgattata cccaggttct     360

gtataatcat ctgcagaaac ataaaccgta tccgcctatt gaagatctgc tgatgcgtga     420

tggtcgtctg aatctggatt ataaagcact gaatcgtagc ctgtatcatg cccatatgct     480

gaattggctg cgtttttttc cgctgggtca tattcatatt gttgatggtg atcgtctgat     540

tcgtgatccg tttcctgaaa ttcagaaagt ggaacgtttt ctgaaactga gtccgcagat     600

taatgccagc aacttctatt ttaacaaaac caaaggcttc tattgcctgc gtgatagcgg     660

taaagatcgt tgtctgcatg aaagcaaagg tcgtgcacat ccgcaggttg atccgaaact     720

gctggataaa ctgcatgaat attttcatga accgaacaaa aaattcttta aactggtggg     780

tcgtaccttc gattggcatt aagtcgac                                        808
```

<210> SEQ ID NO 31

<211> LENGTH: 26
<212> TYPE: DNA
<213> ORGANISM: Artificial Sequence
<220> FEATURE:
<223> OTHER INFORMATION: primer

<400> SEQUENCE: 31
ataagatctg ctgccgaacc cgccaa 26

<210> SEQ ID NO 32
<211> LENGTH: 59
<212> TYPE: DNA
<213> ORGANISM: Artificial Sequence
<220> FEATURE:
<223> OTHER INFORMATION: primer

<400> SEQUENCE: 32
ataaagcttg gatccgagct cgaggcggcc gccagggctg catcgacagt ctgacgacc 59

<210> SEQ ID NO 33
<211> LENGTH: 6556
<212> TYPE: DNA
<213> ORGANISM: Artificial Sequence
<220> FEATURE:
<223> OTHER INFORMATION: plasmid

<400> SEQUENCE: 33
ccgacaccat cgaatggtgc aaaacctttc gcggtatggc atgatagcgc ccggaagaga 60
gtcaattcag ggtggtgaat gtgaaaccag taacgttata cgatgtcgca gagtatgccg 120
gtgtctctta tcagaccgtt tcccgcgtgg tgaaccaggc cagccacgtt tctgcgaaaa 180
cgcgggaaaa agtggaagcg gcgatggcgg agctgaatta cattcccaac cgcgtggcac 240
aacaactggc gggcaaacag tcgttgctga ttggcgttgc cacctccagt ctggccctgc 300
acgcgccgtc gcaaattgtc gcggcgatta aatctcgcgc cgatcaactg ggtgccagcg 360
tggtggtgtc gatggtagaa cgaagcggcg tcgaagcctg taaagcggcg gtgcacaatc 420
ttctcgcgca acgcgtcagt gggctgatca ttaactatcc gctggatgac caggatgcca 480
ttgctgtgga agctgcctgc actaatgttc cggcgttatt tcttgatgtc tctgaccaga 540
cacccatcaa cagtattatt ttctcccatg aagacggtac gcgactgggc gtggagcatc 600
tggtcgcatt gggtcaccag caaatcgcgc tgttagcggg cccattaagt tctgtctcgg 660
cgcgtctgcg tctggctggc tggcataaat atctcactcg caatcaaatt cagccgatag 720
cggaacggga aggcgactgg agtgccatgt ccggttttca acaaaccatg caaatgctga 780
atgagggcat cgttcccact gcgatgctgg ttgccaacga tcagatggcg ctgggcgcaa 840
tgcgcgccat taccgagtcc gggctgcgcg ttggtgcgga tatctcggta gtgggatacg 900
acgataccga agacagctca tgttatatcc cgccgttaac caccatcaaa caggattttc 960
gcctgctggg gcaaaccagc gtggaccgct tgctgcaact ctctcagggc caggcggtga 1020
agggcaatca gctgttgccc gtctcactgg tgaaaagaaa aaccaccctg gcgcccaata 1080
cgcaaaccgc ctctccccgc gcgttggccg attcattaat gcagctggca cgacaggttt 1140
cccgactgga aagcgggcag tgagcgcaac gcaattaatg taagttagct cactcattag 1200
gcacaattct catgtttgac agcttatcat cgactgcacg gtgcaccaat gcttctggcg 1260
tcaggcagcc atcggaagct gtggtatggc tgtgcaggtc gtaaatcact gcataattcg 1320
tgtcgctcaa ggcgcactcc cgttctggat aatgtttttt gcgccgacat cataacggtt 1380
ctggcaaata ttctgaaatg agctgttgac aattaatcat cggctcgtat aatgtgtgga 1440

```
attgtgagcg gataacaatt tcacacagga aacagccagt ccgtttaggt gttttcacga   1500
gcacttcacc aacaaggacc atagcatatg aaaatcgaag aaggtaaact ggtaatctgg   1560
attaacggcg ataaaggcta taacggtctc gctgaagtcg gtaagaaatt cgagaaagat   1620
accggaatta aagtcaccgt tgagcatccg gataaactgg aagagaaatt cccacaggtt   1680
gcggcaactg gcgatggccc tgacattatc ttctgggcac acgaccgctt tggtggctac   1740
gctcaatctg gcctgttggc tgaaatcacc ccggacaaag cgttccagga caagctgtat   1800
ccgtttacct gggatgccgt acgttacaac ggcaagctga ttgcttaccc gatcgctgtt   1860
gaagcgttat cgctgattta taacaaagat ctgctgccga acccgccaaa aacctgggaa   1920
gagatcccgg cgctggataa agaactgaaa gcgaaaggta agagcgcgct gatgttcaac   1980
ctgcaagaac cgtacttcac ctggccgctg attgctgctg acgggggtta tgcgttcaag   2040
tatgaaaacg gcaagtacga cattaaagac gtgggcgtgg ataacgctgg cgcgaaagcg   2100
ggtctgacct tcctggttga cctgattaaa aacaaacaca tgaatgcaga caccgattac   2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc cgcagatgtc cgctttctgg tatgccgtgc gtactgcggt gatcaacgcc   2580
gccagcggtc gtcagactgt cgatgcagcc ctggcggccg cctcgagctc ggatccaagc   2640
ttggcactgg ccgtcgtttt acaacgtcgt gactgggaaa accctggcgt tacccaactt   2700
aatcgccttg cagcacatcc ccctttcgcc agctggcgta atagcgaaga ggcccgcacc   2760
gatcgccctt cccaacagtt gcgcagcctg aatggcgaat ggcagcttgg ctgttttggc   2820
ggatgagata agattttcag cctgatacag attaaatcag aacgcagaag cggtctgata   2880
aaacagaatt tgcctggcgg cagtagcgcg gtggtcccac ctgaccccat gccgaactca   2940
gaagtgaaac gccgtagcgc cgatggtagt gtggggtctc cccatgcgag agtagggaac   3000
tgccaggcat caaataaaac gaaaggctca gtcgaaagac tgggcctttc gttttatctg   3060
ttgtttgtcg gtgaacgctc tcctgagtag gacaaatccg ccgggagcgg atttgaacgt   3120
tgcgaagcaa cggcccggag ggtggcgggc aggacgcccg ccataaactg ccaggcatca   3180
aattaagcag aaggccatcc tgacggatgg cctttttgcg tttctacaaa ctctttttgt   3240
ttatttttct aaatacattc aaatatgtat ccgctcatga gacaataacc ctgataaatg   3300
cttcaataat attgaaaaag gaagagtatg agtattcaac atttccgtgt cgcccttatt   3360
ccctttttttg cggcattttg ccttcctgtt tttgctcacc cagaaacgct ggtgaaagta   3420
aaagatgctg aagatcagtt gggtgcacga gtgggttaca tcgaactgga tctcaacagc   3480
ggtaagatcc ttgagagttt tcgccccgaa gaacgttctc caatgatgag cacttttaaa   3540
gttctgctat gtggcgcggt attatcccgt gttgacgccg ggcaagagca actcggtcgc   3600
cgcatacact attctcagaa tgacttggtt gagtactcac cagtcacaga aaagcatctt   3660
acggatggca tgacagtaag agaattatgc agtgctgcca taaccatgag tgataacact   3720
gcggccaact tacttctgac aacgatcgga ggaccgaagg agctaaccgc ttttttgcac   3780
```

```
aacatggggg atcatgtaac tcgccttgat cgttgggaac cggagctgaa tgaagccata   3840
ccaaacgacg agcgtgacac cacgatgcct gtagcaatgg caacaacgtt gcgcaaacta   3900
ttaactggcg aactacttac tctagcttcc cggcaacaat taatagactg gatggaggcg   3960
gataaagttg caggaccact tctgcgctcg gcccttccgg ctggctggtt tattgctgat   4020
aaatctggag ccggtgagcg tgggtctcgc ggtatcattg cagcactggg gccagatggt   4080
aagccctccc gtatcgtagt tatctacacg acggggagtc aggcaactat ggatgaacga   4140
aatagacaga tcgctgagat aggtgcctca ctgattaagc attggtaact gtcagaccaa   4200
gtttactcat atatacttta gattgattta ccccggttga taatcagaaa agccccaaaa   4260
acaggaagat tgtataagca aatatttaaa ttgtaaacgt taatattttg ttaaaattcg   4320
cgttaaattt ttgttaaatc agctcatttt ttaaccaata ggccgaaatc ggcaaaatcc   4380
cttataaatc aaaagaatag accgagatag ggttgagtgt tgttccagtt tggaacaaga   4440
gtccactatt aaagaacgtg gactccaacg tcaaagggcg aaaaaccgtc tatcagggcg   4500
atggcccact acgtgaacca tcacccaaat caagtttttt ggggtcgagg tgccgtaaag   4560
cactaaatcg gaaccctaaa gggagccccc gatttagagc ttgacgggga aagccggcga   4620
acgtggcgag aaaggaaggg aagaaagcga aaggagcggg cgctagggcg ctggcaagtg   4680
tagcggtcac gctgcgcgta accaccacac ccgccgcgct taatgcgccg ctacagggcg   4740
cgtaaaagga tctaggtgaa gatccttttt gataatctca tgaccaaaat cccttaacgt   4800
gagttttcgt tccactgagc gtcagacccc gtagaaaaga tcaaaggatc ttcttgagat   4860
cctttttttc tgcgcgtaat ctgctgcttg caaacaaaaa aaccaccgct accagcggtg   4920
gtttgtttgc cggatcaaga gctaccaact ctttttccga aggtaactgg cttcagcaga   4980
gcgcagatac caaatactgt ccttctagtg tagccgtagt taggccacca cttcaagaac   5040
tctgtagcac cgcctacata cctcgctctg ctaatcctgt taccagtggc tgctgccagt   5100
ggcgataagt cgtgtcttac cgggttggac tcaagacgat agttaccgga taaggcgcag   5160
cggtcgggct gaacgggggg ttcgtgcaca cagcccagct tggagcgaac gacctacacc   5220
gaactgagat acctacagcg tgagctatga gaaagcgcca cgcttcccga agggagaaag   5280
gcggacaggt atccggtaag cggcagggtc ggaacaggag agcgcacgag ggagcttcca   5340
gggggaaacg cctggtatct ttatagtcct gtcgggtttc gccacctctg acttgagcgt   5400
cgatttttgt gatgctcgtc aggggggcgg agcctatgga aaaacgccag caacgcggcc   5460
tttttacggt tcctggcctt ttgctggcct tttgctcaca tgttctttcc tgcgttatcc   5520
cctgattctg tggataaccg tattaccgcc tttgagtgag ctgataccgc tcgccgcagc   5580
cgaacgaccg agcgcagcga gtcagtgagc gaggaagcgg aagagcgcct gatgcggtat   5640
tttctcctta cgcatctgtg cggtatttca caccgcatat atggtgcact ctcagtacaa   5700
tctgctctga tgccgcatag ttaagccagt atacactccg ctatcgctac gtgactgggt   5760
catggctgcg ccccgacacc cgccaacacc cgctgacgcg ccctgacggg cttgtctgct   5820
cccggcatcc gcttacagac aagctgtgac cgtctccggg agctgcatgt gtcagaggtt   5880
ttcaccgtca tcaccgaaac gcgcgaggca gctgcggtaa agctcatcag cgtggtcgtg   5940
cagcgattca cagatgtctg cctgttcatc cgcgtccagc tcgttgagtt tctccagaag   6000
cgttaatgtc tggcttctga taaagcgggc catgttaagg gcggtttttt cctgtttggt   6060
cactgatgcc tccgtgtaag ggggatttct gttcatgggg gtaatgatac cgatgaaacg   6120
agagaggatg ctcacgatac gggttactga tgatgaacat gcccggttac tggaacgttg   6180
```

tgagggtaaa caactggcgg tatggatgcg gcgggaccag agaaaaatca ctcagggtca 6240
atgccagcgc ttcgttaata cagatgtagg tgttccacag ggtagccagc agcatcctgc 6300
gatgcagatc cggaacataa tggtgcaggg cgctgacttc cgcgtttcca gactttacga 6360
aacacggaaa ccgaagacca ttcatgttgt tgctcaggtc gcagacgttt tgcagcagca 6420
gtcgcttcac gttcgctcgc gtatcggtga ttcattctgc taaccagtaa ggcaaccccg 6480
ccagcctagc cgggtcctca acgacaggag cacgatcatg cgcacccgtg gccaggaccc 6540
aacgctgccc gaaatt 6556

<210> SEQ ID NO 34
<211> LENGTH: 48
<212> TYPE: DNA
<213> ORGANISM: Artificial Sequence
<220> FEATURE:
<223> OTHER INFORMATION: primer

<400> SEQUENCE: 34
atagcggccg cgtcttctgg aggcctgaaa tatgaagaaa ttgactgc 48

<210> SEQ ID NO 35
<211> LENGTH: 31
<212> TYPE: DNA
<213> ORGANISM: Artificial Sequence
<220> FEATURE:
<223> OTHER INFORMATION: primer

<400> SEQUENCE: 35
atactcgagt taattgtgtt ttgcacggct a 31

<210> SEQ ID NO 36
<211> LENGTH: 1575
<212> TYPE: DNA
<213> ORGANISM: Homo sapiens

<400> SEQUENCE: 36
ggccgcgtct tctggaggcc tgaaatatga agaaattgac tgcctgatca acgatgagca 60
taccattaaa ggtcgtcgtg aaggtaatga agtttttctg ccgtttacct gggtggagaa 120
atactttgat gtttatggta aagtggtgca gtatgatggc tatgatcgtt ttgaatttag 180
ccatagctac agcaaagttt atgcacagcg tgcaccgtat catcctgatg gtgtttttat 240
gagctttgag ggctataatg ttgaagttcg tgatcgcgtt aaatgcatta gcggtgttga 300
aggtgttccg ctgagcaccc agtggggtcc gcagggttat ttctatccga ttcagattgc 360
acagtatggc ctgagccatt atagcaaaaa tctgaccgaa aaaccgcctc acattgaagt 420
ttatgaaacc gcagaagatc gcgacaaaaa caaaccgaat gattggaccg ttccgaaagg 480
ttgttttatg gcaaatgttg cagataaaag ccgcttcacc aatgtgaaac agtttattgc 540
accggaaacc agcgaaggtg ttagcctgca gctgggtaat accaaagatt ttatcattag 600
cttcgatctg aaatttctga ccaatggtag cgttagcgtt gttctggaaa ccaccgaaaa 660
aaatcagctg tttaccatcc attatgtgag caatgcccag ctgattgcat ttaaagaacg 720
cgatatctat tatggcattg gtccgcgtac cagttggagc accgttaccc gtgatctggt 780
taccgatctg cgtaaaggtg ttggtctgag caatacaaaa gcagttaaac cgaccaaaat 840
tatgccgaaa aaagttgttc gtctgatcgc caaaggtaaa ggttttctgg ataacattac 900
cattagcacc accgcacata tggcagcatt ttttgcagca agcgattggc tggttcgtaa 960

```
ccaggatgaa aaaggtggtt ggccgattat ggttacccgt aaactgggtg aaggttttaa   1020

aagcctggaa ccgggttggt atagcgcaat ggcacagggt caggcaatta gcaccctggt   1080

tcgtgcatat ctgctgacca aagatcatat ttttctgaat agcgcactgc gtgcaaccgc   1140

accgtacaaa tttctgtcag aacagcatgg tgttaaagcc gtgtttatga acaaacacga   1200

ttggtatgaa gaatatccga ccaccccgag cagctttgtt ctgaatggtt ttatgtatag   1260

cctgatcggt ctgtacgacc tgaaagaaac agccggtgaa aaactgggta aagaagcacg   1320

tagcctgtac gaacgtggta tggaaagcct gaaagcaatg ctgccgctgt atgataccgg   1380

tagcggcacc atttatgatc tgcgtcattt tatgctgggt atcgcaccga atctggcacg   1440

ttgggattat cataccaccc atattaatca gctgcaactg ctgagtacca ttgatgaaag   1500

tccggtgttt aaagaatttg tgaaacgctg gaaaagctac ctgaaaggta gccgtgcaaa   1560

acacaattaa ctcga                                                    1575


<210> SEQ ID NO 37
<211> LENGTH: 517
<212> TYPE: PRT
<213> ORGANISM: Homo sapiens

<400> SEQUENCE: 37

Gly Leu Lys Tyr Glu Glu Ile Asp Cys Leu Ile Asn Asp Glu His Thr
1               5                   10                  15

Ile Lys Gly Arg Arg Glu Gly Asn Glu Val Phe Leu Pro Phe Thr Trp
            20                  25                  30

Val Glu Lys Tyr Phe Asp Val Tyr Gly Lys Val Val Gln Tyr Asp Gly
        35                  40                  45

Tyr Asp Arg Phe Glu Phe Ser His Ser Tyr Ser Lys Val Tyr Ala Gln
    50                  55                  60

Arg Ala Pro Tyr His Pro Asp Gly Val Phe Met Ser Phe Glu Gly Tyr
65                  70                  75                  80

Asn Val Glu Val Arg Asp Arg Val Lys Cys Ile Ser Gly Val Glu Gly
                85                  90                  95

Val Pro Leu Ser Thr Gln Trp Gly Pro Gln Gly Tyr Phe Tyr Pro Ile
            100                 105                 110

Gln Ile Ala Gln Tyr Gly Leu Ser His Tyr Ser Lys Asn Leu Thr Glu
        115                 120                 125

Lys Pro Pro His Ile Glu Val Tyr Glu Thr Ala Glu Asp Arg Asp Lys
    130                 135                 140

Asn Lys Pro Asn Asp Trp Thr Val Pro Lys Gly Cys Phe Met Ala Asn
145                 150                 155                 160

Val Ala Asp Lys Ser Arg Phe Thr Asn Val Lys Gln Phe Ile Ala Pro
                165                 170                 175

Glu Thr Ser Glu Gly Val Ser Leu Gln Leu Gly Asn Thr Lys Asp Phe
            180                 185                 190

Ile Ile Ser Phe Asp Leu Lys Phe Leu Thr Asn Gly Ser Val Ser Val
        195                 200                 205

Val Leu Glu Thr Thr Glu Lys Asn Gln Leu Phe Thr Ile His Tyr Val
    210                 215                 220

Ser Asn Ala Gln Leu Ile Ala Phe Lys Glu Arg Asp Ile Tyr Tyr Gly
225                 230                 235                 240

Ile Gly Pro Arg Thr Ser Trp Ser Thr Val Thr Arg Asp Leu Val Thr
                245                 250                 255

Asp Leu Arg Lys Gly Val Gly Leu Ser Asn Thr Lys Ala Val Lys Pro
```

```
            260                 265                 270

Thr Lys Ile Met Pro Lys Lys Val Val Arg Leu Ile Ala Lys Gly Lys
        275                 280                 285

Gly Phe Leu Asp Asn Ile Thr Ile Ser Thr Thr Ala His Met Ala Ala
    290                 295                 300

Phe Phe Ala Ala Ser Asp Trp Leu Val Arg Asn Gln Asp Glu Lys Gly
305                 310                 315                 320

Gly Trp Pro Ile Met Val Thr Arg Lys Leu Gly Glu Gly Phe Lys Ser
                325                 330                 335

Leu Glu Pro Gly Trp Tyr Ser Ala Met Ala Gln Gly Gln Ala Ile Ser
            340                 345                 350

Thr Leu Val Arg Ala Tyr Leu Leu Thr Lys Asp His Ile Phe Leu Asn
        355                 360                 365

Ser Ala Leu Arg Ala Thr Ala Pro Tyr Lys Phe Leu Ser Glu Gln His
    370                 375                 380

Gly Val Lys Ala Val Phe Met Asn Lys His Asp Trp Tyr Glu Glu Tyr
385                 390                 395                 400

Pro Thr Thr Pro Ser Ser Phe Val Leu Asn Gly Phe Met Tyr Ser Leu
                405                 410                 415

Ile Gly Leu Tyr Asp Leu Lys Glu Thr Ala Gly Glu Lys Leu Gly Lys
            420                 425                 430

Glu Ala Arg Ser Leu Tyr Glu Arg Gly Met Glu Ser Leu Lys Ala Met
        435                 440                 445

Leu Pro Leu Tyr Asp Thr Gly Ser Gly Thr Ile Tyr Asp Leu Arg His
    450                 455                 460

Phe Met Leu Gly Ile Ala Pro Asn Leu Ala Arg Trp Asp Tyr His Thr
465                 470                 475                 480

Thr His Ile Asn Gln Leu Gln Leu Leu Ser Thr Ile Asp Glu Ser Pro
                485                 490                 495

Val Phe Lys Glu Phe Val Lys Arg Trp Lys Ser Tyr Leu Lys Gly Ser
            500                 505                 510

Arg Ala Lys His Asn
        515
```

<210> SEQ ID NO 38
<211> LENGTH: 63
<212> TYPE: DNA
<213> ORGANISM: Artificial Sequence
<220> FEATURE:
<223> OTHER INFORMATION: primer

<400> SEQUENCE: 38

```
atagcggccg cgcagactaa tgcagcagcg gatgaagaag aagatatcgt cattatctat     60

aac                                                                    63
```

<210> SEQ ID NO 39
<211> LENGTH: 36
<212> TYPE: DNA
<213> ORGANISM: Artificial Sequence
<220> FEATURE:
<223> OTHER INFORMATION: primer

<400> SEQUENCE: 39

```
atactcgagt taattgcttt tcggatagat tttttc                                36
```

<210> SEQ ID NO 40
<211> LENGTH: 897

<212> TYPE: DNA
<213> ORGANISM: Cricetulus griseus

<400> SEQUENCE: 40

```
ggccgcgcag actaatgcag cagcggatga agaagaagat atcgtcatta tctataaccg      60
tgttccgaaa accgcaagca ccagctttac caatattgca tatgatctgt gcgccaaaaa     120
tcgctatcat gtgctgcata ttaacaccac caaaaataac ccggttatga gcctgcagga     180
tcaggttcgt tttgttaaaa acattaccac ctggaacgaa atgaaaccgg gtttttatca     240
tggccatatc agctatctgg attttgcgaa atttggcgtg aaaaaaaaac cgatctacat     300
caacgttatt cgcgatccga ttgaacgtct ggttagctat tattactttc tgcgcttcgg     360
tgatgattat cgtccgggtc tgcgtcgtcg taaacagggc gacaaaaaaa cctttgatga     420
atgtgttgcc gaaggtggta gcgattgtgc accggaaaaa ctgtggctgc agattccgtt     480
tttttgcggt catagcagcg aatgttggaa tgttggtagc cgttgggcaa tggatcaggc     540
caaatataac ctgatcaacg aatattttct ggtgggtgtg accgaagaac tggaagattt     600
cattatgctg ctggaagcag cactgcctcg ttttttcgt ggtgcaaccg atctgtatcg     660
taccggtaaa aaaagccatc tgcgtaaaac gacggaaaaa aaactgccga ccaaacagac     720
cattgcaaaa ctgcagcaga gcgatatttg gaaaatggaa aacgagtttt atgaatttgc     780
cctggaacag tttcagttta ttcgtgcaca tgcagttcgt gaaaaagatg gtgatctgta     840
tattctggcc cagaacttct tctacgaaaa aatctatccg aaaagcaatt aactcga       897
```

<210> SEQ ID NO 41
<211> LENGTH: 288
<212> TYPE: PRT
<213> ORGANISM: Cricetulus griseus

<400> SEQUENCE: 41

```
Asp Glu Glu Glu Asp Ile Val Ile Ile Tyr Asn Arg Val Pro Lys Thr
1               5                   10                  15

Ala Ser Thr Ser Phe Thr Asn Ile Ala Tyr Asp Leu Cys Ala Lys Asn
            20                  25                  30

Arg Tyr His Val Leu His Ile Asn Thr Thr Lys Asn Asn Pro Val Met
        35                  40                  45

Ser Leu Gln Asp Gln Val Arg Phe Val Lys Asn Ile Thr Thr Trp Asn
    50                  55                  60

Glu Met Lys Pro Gly Phe Tyr His Gly His Ile Ser Tyr Leu Asp Phe
65                  70                  75                  80

Ala Lys Phe Gly Val Lys Lys Lys Pro Ile Tyr Ile Asn Val Ile Arg
                85                  90                  95

Asp Pro Ile Glu Arg Leu Val Ser Tyr Tyr Tyr Phe Leu Arg Phe Gly
            100                 105                 110

Asp Asp Tyr Arg Pro Gly Leu Arg Arg Arg Lys Gln Gly Asp Lys Lys
        115                 120                 125

Thr Phe Asp Glu Cys Val Ala Glu Gly Gly Ser Asp Cys Ala Pro Glu
    130                 135                 140

Lys Leu Trp Leu Gln Ile Pro Phe Phe Cys Gly His Ser Ser Glu Cys
145                 150                 155                 160
```

-continued

```
Trp Asn Val Gly Ser Arg Trp Ala Met Asp Gln Ala Lys Tyr Asn Leu
                165                 170                 175

Ile Asn Glu Tyr Phe Leu Val Gly Val Thr Glu Glu Leu Glu Asp Phe
            180                 185                 190

Ile Met Leu Leu Glu Ala Ala Leu Pro Arg Phe Phe Arg Gly Ala Thr
        195                 200                 205

Asp Leu Tyr Arg Thr Gly Lys Lys Ser His Leu Arg Lys Thr Thr Glu
    210                 215                 220

Lys Lys Leu Pro Thr Lys Gln Thr Ile Ala Lys Leu Gln Gln Ser Asp
225                 230                 235                 240

Ile Trp Lys Met Glu Asn Glu Phe Tyr Glu Phe Ala Leu Glu Gln Phe
                245                 250                 255

Gln Phe Ile Arg Ala His Ala Val Arg Glu Lys Asp Gly Asp Leu Tyr
            260                 265                 270

Ile Leu Ala Gln Asn Phe Phe Tyr Glu Lys Ile Tyr Pro Lys Ser Asn
        275                 280                 285
```

HEPARAN SULFATE HAVING HIGH 3-O-SULFATION RATE IN GLUCOSAMINE RESIDUES

This application is a Continuation of, and claims priority under 35 U.S.C. § 120 to, International Application No. PCT/JP2016/087689, filed Dec. 16, 2016, and claims priority therethrough under 35 U.S.C. § 119 to Japanese Patent Application No. 2015-257022, filed Dec. 28, 2015, the entireties of which are incorporated by reference herein. Also, the Sequence Listing filed electronically herewith is hereby incorporated by reference (File name: 2018-06-26T_US-580 Seq List; File size: 96 KB; Date recorded: Jun. 26, 2018).

BACKGROUND OF THE INVENTION

Field of the Invention

The present invention relates to a novel sulfated polysaccharide having anticoagulant activity. The sulfated polysaccharide having anticoagulant activity is useful, for example, in the medical field.

Brief Description of the Related Art

Various heparan sulfates such as heparin are known to be sulfated polysaccharides having anticoagulant activity. That is, heparin is an anticoagulant, and is used for the treatment of thromboembolism and disseminated intravascular coagulation (DIC) and for the prevention of the blood coagulation in artificial dialysis or extracorporeal circulation.

Heparin exhibits an anticoagulation effect through activation of antithrombin III. Antithrombin III is an anticoagulation factor that inhibits thrombin, factor Xa, which is the active form of a factor X, and other serine proteases by binding to an active serine site. Thrombin is a blood coagulation factor, and factor Xa is involved in maturation of thrombin. Heparin binds to antithrombin III, and as a result, changes its structure and activates its inhibitory action. Thrombin has a higher affinity for the heparin-antithrombin III complex than factor Xa.

Low molecular weight heparin with an average molecular weight of 4000 to 6000 Da, obtained by an enzymatic/chemical treatment and fractionation of heparin, has fewer side effects, such as bleeding, and has become more frequently used in recent years. Low molecular weight heparin can bind to antithrombin III due to its short sugar chain, but scarcely binds to thrombin. Here, thrombin needs to bind to heparin in the inhibition of thrombin by heparin-antithrombin III complex, whereas factor Xa does not need to bind to heparin in the inhibition of factor Xa by heparin-antithrombin III complex. Thus, the low molecular weight heparin scarcely inhibits the action of thrombin, whereas it can inhibit an action of factor Xa.

At present, a majority of heparin preparations are extraction products from porcine intestinal mucosa. However, a fatal accident caused by contamination occurred in 2008, and thus the development of the production of quality-controlled non-animal-derived heparin has been investigated.

Many methods of producing non-animal-derived heparin have been reported, and are broadly divided into two types. In the first type, heparosan, which is a sugar chain skeleton of heparin, is produced by a fermentation method using a microorganism such as an *Escherichia coli* K5 strain, and is converted to an anticoagulant polysaccharide like heparin using a chemical or enzymatic technique, followed by depolymerizing it using a chemical, enzymatic or physical technique (Lindahl et al. (2005), J. Med. Chem., 48(2): 349-352; Zhang et al. (2008), Journ. of the ACS, 130 (39): 12998-13007). In the second type, sugar chains are linked solely by a chemical synthesis method (US20120116066).

Methods of producing heparin using heparosan as a starting material have been reported, and mainly involve chemical or enzymatic conversion. The produced heparin-analogous polysaccharides are different in structural characteristics and strength of the anticoagulant activity (U.S. Pat. No. 8,227,449; US20120322114).

In the heparin-analogous polysaccharides produced via a chemical conversion method, the 3-O-sulfation rate in glucosamine residues is high, and a portion of glucuronic acid residues are also 3-O-sulfated. The 3-O-sulfated glucuronic acid residues have a structure that is not present in animal-derived heparin, and its in vivo side reaction is a potential problem.

Alternatively, while the heparin-analogous polysaccharides produced in the enzymatic conversion method have the same sulfation pattern as that in animal-derived heparin, its anticoagulant activity is about one half of that in animal-derived products.

Therefore, a heparin-analogous polysaccharide having the same sulfation pattern as that in animal-derived heparin and exhibiting a high anticoagulant activity has not been reported.

SUMMARY OF THE INVENTION

It is an aspect of the present invention to provide a novel sulfated polysaccharide having an anticoagulant activity.

A sulfated polysaccharide is described that includes a repetitive disaccharide unit composed of a hexuronic acid, also called a "HexA" residue and an α-D-glucosamine, also called a "GlcN" residue. This sulfated polysaccaharide exhibits a high 3-O-sulfation rate in GlcN residues and has an anticoagulant activity.

It is an aspect of the present invention to provide a polysaccharide having an anticoagulant activity, said polysaccharide comprising a repetitive disaccharide unit having the following general formula (I):

(I)

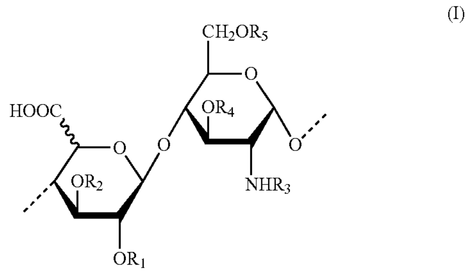

wherein $R_1$, $R_2$, $R_4$ and $R_5$ each independently represent a hydrogen or a sulfate group; $R_3$ represents a hydrogen, a sulfate group or an acetyl group; at least a portion of the $R_3$ is the sulfate group; the rate of the sulfate group as $R_4$ is 13% or more; and the rate of the sulfate group as $R_5$ is 50% or more.

It is a further aspect of the present invention to provide the polysaccharide as described above, wherein the content rate of said disaccharide unit is 90% or more.

It is a further aspect of the present invention to provide the polysaccharide as described above, wherein 50% or more of the total number of sugar chains present in said polysaccharide have the following general formula (II):

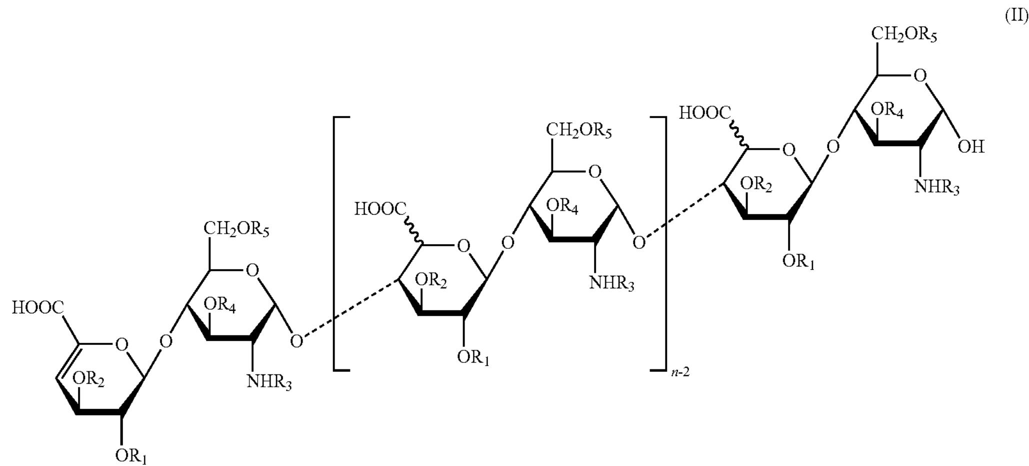

wherein $R_1$ to $R_5$ are the same as $R_1$ to $R_5$ in said general formula (I); and n is 3 to 30 as an average value.

It is a further aspect of the present invention to provide the polysaccharide as described above, wherein 50% or more of the total number of sugar chains present in said polysaccharide have the following general formula (II):

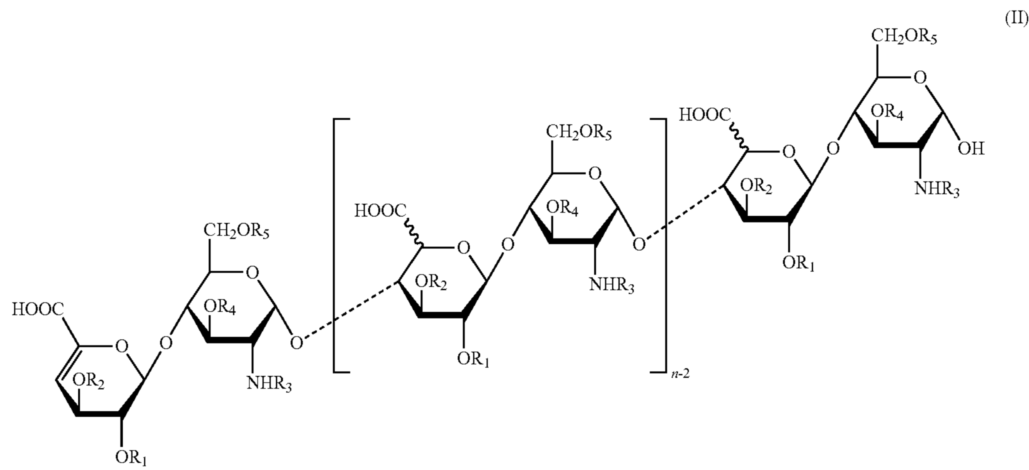

wherein $R_1$ to $R_5$ are the same as $R_1$ to $R_5$ in said general formula (I); and n is 3 to 15 as the average value.

It is a further aspect of the present invention to provide the polysaccharide as described above, wherein the average number of linked sugar residues is 6 to 60.

It is a further aspect of the present invention to provide the polysaccharide as described above, wherein the average number of linked sugar residues is 6 to 30.

It is a further aspect of the present invention to provide the polysaccharide as described above, wherein the number average molecular weight measured by gel permeation chromatography using pullulan as a standard is 8000 to 60000.

It is a further aspect of the present invention to provide the polysaccharide as described above, wherein the number average molecular weight measured by gel permeation chromatography using pullulan as a standard is 12000 to 40000.

It is a further aspect of the present invention to provide the polysaccharide as described above, wherein the weight average molecular weight measured by gel permeation chromatography using pullulan as a standard is 10000 to 100000.

It is a further aspect of the present invention to provide the polysaccharide as described above, wherein the weight average molecular weight measured by gel permeation chromatography using pullulan as a standard is 15000 to 50000.

It is a further aspect of the present invention to provide the polysaccharide as described above, wherein the rate of iduronic acid residues as hexuronic acid residues in said disaccharide unit is 0% to 70%.

It is a further aspect of the present invention to provide the polysaccharide as described above, wherein the rate of a sulfate group as $R_1$ is 0% to 80%.

It is a further aspect of the present invention to provide the polysaccharide as described above, wherein the rate of a sulfate group as $R_1$ in a iduronic acid residues 0% to 100%.

It is a further aspect of the present invention to provide the polysaccharide as described above, wherein the rate of a sulfate group as $R_1$ in glucuronic acid residues 0% to 50%.

It is a further aspect of the present invention to provide the polysaccharide as described above, wherein the rate of a sulfate group as $R_2$ is less than 1%.

It is a further aspect of the present invention to provide the polysaccharide as described above, wherein the rate of a sulfate group as $R_3$ is 70% to 100%.

It is a further aspect of the present invention to provide the polysaccharide as described above, wherein the rate of an acetyl group as $R_3$ is 0 to 33%.

It is a further aspect of the present invention to provide the polysaccharide as described above, wherein the rate of a sulfate group as $R_4$ is 45% or less.

It is a further aspect of the present invention to provide the polysaccharide as described above, wherein the rate of a sulfate group as $R_5$ is 70% to 100%.

It is a further aspect of the present invention to provide the polysaccharide as described above, comprising a disaccharide unit selected from the group consisting of GlcA-GlcN (NS3S6S), GlcA(2S)-GlcN(NS6S), IdoA(2S)-GlcN(NS6S), GlcA-GlcN(NS6S), IdoA(2S)-GlcN(NS), IdoA(2S)-GlcN (NS3S), IdoA-GlcN(NS6S), GlcA-GlcN(NS), and combinations thereof at a total content rate of 50% or more.

It is a further aspect of the present invention to provide the polysaccharide as described above, wherein the ratio of anti-factor Xa activity to anti-factor IIa activity is 1.5 or more.

It is a further aspect of the present invention to provide the polysaccharide as described above, wherein the ratio (Mw/Mn) of a weight average molecular weight (Mw) to a number average molecular weight (Mn) measured by gel permeation chromatography using pullulan as a standard is 1.5 or less.

It is a further aspect of the present invention to provide the polysaccharide as described above, which is a free form, or a pharmacologically acceptable salt, or a mixture thereof.

It is a further aspect of the present invention to provide the polysaccharide as described above, wherein said salt is selected from the group consisting of an ammonium salt, a sodium salt, a lithium salt, and a calcium salt.

It is a further aspect of the present invention to provide a pharmaceutical composition comprising the polysaccharide as described above.

It is a further aspect of the present invention to provide a method of preventing, ameliorating, and/or treating a symptom attributed to blood coagulation comprising administering the composition as described above.

It is a further aspect of the present invention to provide the method as described above, wherein said symptom is selected from the group consisting of disseminated intravascular coagulation syndrome, thrombotic embolism, blood coagulation in artificial dialysis, and blood coagulation in extracorporeal circulation.

The present invention provides a novel sulfated polysaccharide having anticoagulant activity.

DETAILED DESCRIPTION OF THE EXEMPLARY EMBODIMENTS

<1> Polysaccharide

The polysaccharide as described herein is a novel sulfated polysaccharide having an anticoagulant activity. The polysaccharide can be optionally referred to as "heparan sulfate". The polysaccharide may be composed of a single type of sugar chain or may be a mixture of multiple types of sugar chains. The polysaccharide is typically obtained as a mixture of multiple types of sugar chains. The "mixture of multiple types of sugar chains" can refer to a combination of two or more types of sugar chains that are different in structure, such as in the number of linked sugars, molecular weight, and/or type and position of a substituent, and the like. When the polysaccharide is composed of a single type of sugar chain, each parameter that identifies the polysaccharide corresponds to that parameter in that sugar chain unless otherwise specified. When the polysaccharide is a mixture of multiple types of sugar chains, each parameter that identifies the polysaccharide corresponds to an averaged value of the parameters in the entire mixture unless otherwise specified. The same applies to other polysaccharides such as intermediates upon producing the polysaccharide.

Each parameter that identifies the polysaccharide can be determined by known techniques used for detection and identification of compounds such as polysaccharides. Examples of such techniques can include a disaccharide analysis, a molecular weight analysis, such as gel permeation chromatography; GPC, aqueous size exclusion chromatography (SEC) using a ultraviolet and visible light absorbance detector (UV), and a refractive index detector (RI) (SEC-RI/UV method), as well as HPLC, LC/MS, NMR. These techniques can be used alone or in combination as appropriate. These techniques can be appropriately chosen depending on the type of parameter to be determined. For example, the disaccharide structure or a content rate thereof can be determined by disaccharide analysis. The disaccharide analysis can be performed by a standard method. The disaccharide analysis can be performed according to the conditions in a previous report (T. Imanari, et. al., "High-performance liquid chromatographic analysis of glycosaminoglycan-derived oligosaccharides." J. O. Chromato. A, 720, 275-293(1996)). That is, for example, the amount of constituent disaccharides can be quantified by, as needed, decomposing a polysaccharide N-sulfated into unsaturated disaccharides using heparinase, and separating and quantifying the decomposed products. Examples of heparinase can include heparinase I, heparinase II, and heparinase III. Heparinase can be used alone or in combination as appropriate. Heparinase can be appropriately chosen depending on various conditions such as the type of hexuronic acid (HexA) residue present in the polysaccharide. For example, a combination of heparinase II and III can be utilized for the disaccharide analysis of a polysaccharide including a β-D-glucuronic acid (GlcA) residue. Also for example, a combination of heparinase I and II can be utilized for the disaccharide analysis of a polysaccharide including an α-L-iduronic acid (IdoA) residue. The amount of each constituent disaccharide can be quantified by decomposing the polysaccharide with a nitrous acid and separating and quantifying the decomposed product. The separation and quantification of the decomposed product can be performed by known methods used for identification of compounds such as HPLC, LC/MS. Conditions for the disaccharide analysis specifically can include, for example, the conditions described in the Examples herein. The amount of a target disaccharide unit can be calculated based on the amount of each constituent disaccharide. When a polysaccharide is cleaved using heparinase such as heparinase III, typically, the linkage between C4 and C5 becomes a double bond in a HexA residue at a resulting unreduced terminus. The IdoA residue and the GlcA residue are indistinguishable in the HexA residue when there is a double bond between C4 and C5. Thus, to distinguish the IdoA residue from the GlcA residue, disaccharide analysis can be performed by a technique such as nitrous acid decomposition method that can distinguish the IdoA residue from the GlcA residue. Each parameter that identifies other polysaccharides such as intermediates when the polysaccharide is produced can also be determined as well.

The average molecular weight, that is, the number average molecular weight (Mn) and the weight average molecular weight (Mw), can directly be determined using pullulan as a standard unless otherwise indicated. Alternatively, a true average molecular weight of heparan sulfate may be calculated indirectly by proportional calculation based on a molecule having a known true average molecular weight, for example, enoxaparin sodium. The average molecular weight of heparan sulfate may be measured directly or indirectly as above, and can be measured directly.

The polysaccharide as described herein is specifically a polysaccharide having an anticoagulant activity that includes a repetitive structure of a disaccharide unit as shown in the following general formula (I):

(I)

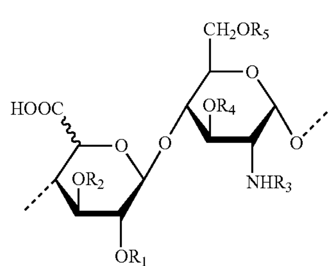

In the formula, $R_1$, $R_2$, $R_4$ and $R_5$ each independently represent a hydrogen (—H) or a sulfate group (—$SO_3H$), and $R_3$ represents a hydrogen (—H), a sulfate group (—$SO_3H$), or an acetyl group (—$COCH_3$). $R_1$ to $R_5$ are independently selected in each repeated unit and each sugar chain. A type of a hexuronic acid (HexA) residue is also independently selected in each repeated unit and each sugar chain.

The polysaccharide can include the above repetitive structure as a major constituent element. That "the polysaccharide may include the above repetitive structure as a major constituent element" may mean that the above repetitive structure is present in an amount of 90% or more, 95% or more, 97% or more, 99% or more or 100% (all) of the polysaccharide. That "the polysaccharide may include the above repetitive structure as a major constituent element" may substantially mean that the above disaccharide unit, that is, the disaccharide unit shown in the general formula (I), is present in an amount of 90% or more, 95% or more, 97% or more, 99% or more or 100% (all) of the polysaccharide). The percentage of the portion of the above disaccharide unit in the polysaccharide can also be referred to as the "content rate of the above disaccharide unit". That is, the content rate of the above disaccharide unit in the polysaccharide may be expressed, for example, as being 90% or more, 95% or more, 97% or more, 99% or more or 100% of the entire polysaccharide. The content rate of the above disaccharide unit can be measured by, for example, disaccharide analysis. That is, the content rate of the above disaccharide unit can be calculated, for example, as a percentage (molar ratio) of the total amount of the above disaccharide units relative to the total amount of disaccharide when the polysaccharide is subjected to the disaccharide analysis.

The number of average repeats of the above disaccharide unit, an average number of linked sugars, the number average molecular weight (Mn), and the weight average molecular weight (Mw) in the polysaccharide can be appropriately configured. The number of average repeats of the above disaccharide unit may be, for example, 3 or more, 4 or more, 5 or more, or 6 or more; and 50 or less, 30 or less, 20 or less, 15 or less, 12 or less, or 9 or less, or a combination thereof. Specifically, the number of average repetition of the above disaccharide unit may be 3 to 15, or 6 to 9. The average number of linked sugars (number of residues) may be, for example, 6 or more, 8 or more, 10 or more, or 12 or more; and 100 or less, 60 or less, 40 or less, 30 or less, 24 or less, or 18 or less, or a combination thereof. Specifically, the average number of linked sugars may be, for example, 6 to 60, 6 to 30, or 12 to 18 residues. The average number of repetitions and the average number of linked sugars can be determined by techniques used for detection or identification of compounds as exemplified above. Specifically, the average number of repetitions and the average number of linked sugars can be determined, for example, based on a molecular weight. The molecular weight can be measured by a standard method. A method of measuring the molecular weight can include gel permeation chromatography (GPC), and aqueous size exclusion chromatography (SEC) using a ultraviolet and visible light absorbance detector (UV) and a refractive index detector (RI) (SEC-RI/UV method; according to the European Pharmacopeia (EP)). Specifically, conditions for measuring the molecular weight by GPC can include, for example, conditions described in Examples herein. The number average molecular weight (Mn) may be, for example, 7000 or more, 8000 or more, 10000 or more, 12000 or more, 15000 or more, or 18000 or more; and 150000 or less, 100000 or less, 60000 or less, 50000 or less, 43000 or less or 40000 or less, or a combination thereof, as measured by GPC using pullulan as a standard. Specifically, the number average molecular weight (Mn) may be, for example, 8000 to 60000, or 12000 to 40000, or 18000 to 43000 as measured by GPC using pullulan as a standard. The weight average molecular weight (Mw) may be, for example, 9000 or more, 10000 or more, 12000 or more, 15000 or more, 21000 or more, or 25000 or more; and 200000 or less, 150000 or less, 100000 or less, 80000 or less, 60000 or less, or 50000 or less, or a combination thereof as measured by GPC using pullulan as a standard. Specifically, the weight average molecular weight (Mw) may be, for example, 10000 to 100000 or 15000 to 50000, or 25000 to 60000 as measured by GPC using pullulan as a standard. A ratio (Mw/Mn) of the weight average molecular weight (Mw) to the number average molecular weight (Mn) may be, for example, 1 or more; and 2.0 or less, 1.9 or less, 1.8 or less, 1.7 or less, 1.6 or less, 1.55 or less, 1.5 or less, 1.45 or less, 1.4 or less, 1.35 or less, 1.3 or less, 1.25 or less, or 1.2 or less, or a combination thereof as measured by GPC using pullulan as a standard. Specifically, the ratio of the weight average molecular weight to the number average molecular weight (Mw/Mn) may be, for example, 1 to 1.6, 1 to 1.5 or 1 to 1.4 as measured by GPC using pullulan as a standard.

The above disaccharide unit is composed of a hexuronic acid (HexA) residue (left sugar residue in the formula) and α-D-glucosamine (GlcN) residue (right sugar residue in the formula). In the above disaccharide unit, a HexA residue side (left side) and a GlcN residue side (right side) can also be referred to as a "non-reduced terminal side" and a "reduced terminal side", respectively. The hexuronic acid residue can be a β-D-glucuronic acid (GlcA) residue or an α-L-iduronic acid (IdoA) residue. That is, the term "hexuronic acid (HexA)" can be an inclusive or generic term for β-D-glucuronic acid (GlcA) and α-L-iduronic acid (IdoA).

The term "hexuronic acid (HexA)", that is, the term, "β-D-glucuronic acid (GlcA)" and "α-L-iduronic acid (IdoA)" can include all possible derivatives depending on selection of $R_1$ and $R_2$, unless otherwise specified. The term "α-D-glucosamine" can include potentially all derivatives depending on selection of $R_3$, $R_4$, and $R_5$ unless otherwise specified.

The polysaccharide as described herein may have the above repetition structure so that the above disaccharide unit is present in a part or all of the non-reduced terminus. For example, 90% or more, 95% or more, 97% or more, 99% or more or 100% of disaccharide units at the non-reduced terminus of the polysaccharide may be the above disaccharide unit. That is, for example, 90% or more, 95% or more, 97% or more, 99% or more or 100% of sugar residues at the non-reduced terminus of the polysaccharide may be the HexA residue. Also the polysaccharide may have the above repetition structure so that the above disaccharide unit is present in a part or all of the reduced terminus. For example, 90% or more, 95% or more, 97% or more, 99% or more or 100% of disaccharide units at the reduced terminus of the polysaccharide may be the above disaccharide unit. That is, for example, 90% or more, 95% or more, 97% or more, 99% or more or 100% of sugar residues at the reduced terminus of the polysaccharide may be the GlcN residue. When the above disaccharide unit is present at the terminus of the sugar chain, a terminal glycoside linkage may be appropriately replaced with an adequate structure as a terminus. That is, the glycoside linkage at position C-4 of the HexA residue at the non-reduced terminus may be replaced with a hydroxyl group (—OH) or with a double bond between C-4 and C-5. In the HexA residue having a double bond between C-4 and C-5, the IdoA residue and the GlcA residue are indistinguishable. Thus, when each parameter that identifies the polysaccharide is determined, the HexA residue is noted as being neither the IdoA residue nor the GlcA residue unless otherwise specified. Also, the glycoside linkage at position C-1 of the GlcN residue at the reduced terminus may be replaced with, for example, a hydroxyl group (—OH).

More specifically, the polysaccharide may include a structure shown in the following general formula (II). For example, a part or all of the polysaccharide, that is, a part or all of the sugar chains that make up the polysaccharide may have the structure shown in the following formula (II). For example, of the total number of sugar chains in the polysaccharide, 50% or more, 70% or more, 80% or more, 90% or more, 95% or more, 97% or more, 99% or more, or 100% that make up the polysaccharide can have the structure shown in the following formula (II). In the formula, $R_1$ to $R_5$ are as described above. In the formula, the number "n" represents the number of repeats of the above disaccharide unit in the formula. The number "n" may be configured so that the polysaccharide can have the number of repeats of the above disaccharide unit, the average number of linked sugar chains, the number average molecular weight (Mn), the weight average molecular weight (Mw) or combinations thereof as described above. The number "n" can be calculated by further converting a weight average molecular weight in terms of pullulan using a molecular weight of enoxaparin sodium (Sanofi-Aventis, France), that is, a low molecular weight heparin formulation. Specifically, the value 3.75, which is calculated by dividing the value 16215, which is the measured value of enoxaparin sodium based on GPC method, by the value 4325, which is the measured value based on SEC-RI/UV method according to the EP, is used as a conversion factor, and the number "n" can be calculated by dividing the weight average molecular weight in terms of pullulan of the polysaccharide by the conversion factor 3.75 and the heparin disaccharide average molecular weight 665.4. In each sugar chain, the number "n" may be, for example, 3 to 200, 3 to 100, or 3 to 50. Also, the number "n" may be specifically, for example, the number of the average repeats of the above disaccharide unit (e.g., 3 to 30, 3 to 15, or 6 to 9) in the polysaccharide, as an average value of the entire mixture of the sugar chains.

(II)

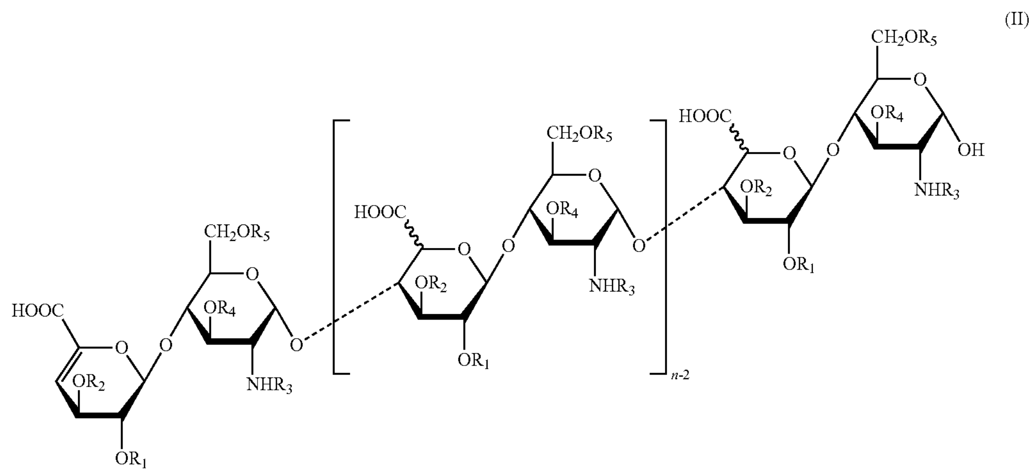

The percentage of IdoA residues in the HexA residue, also referred to as an "epimerization rate", can be, for example, 0% or more, 10% or more, 20% or more, 30% or more, 40% or more, or 50% or more; and 100% or less, 90% or less, 80% or less, 70% or less, or 60% or less, or a combination thereof. Specifically, the epimerization rate may be, for example, 0% to 70%, 20% to 70% or 30% to 60%. In this case, the "HexA residue" upon calculating the epimerization rate refers to the IdoA residue and the GlcA residue provided that the HexA residue does not have a double bond between C-4 and C-5. The epimerization rate can be measured, for example, by the disaccharide analysis. That is, the epimerization rate can be calculated as a percentage (molar ratio) of the amount of the above disaccharide units where the HexA residue is the IdoA residue relative to the total amount of the above disaccharide units where the HexA residue is the IdoA residue or the GlcA residue when the polysaccharide is subjected to the disaccharide analysis. A linkage between C-4 and C-5 of the HexA residue may be a double bond. The position of the HexA residue having a double bond between C-4 and C-5 is not particularly limited. For example in particular, the linkage between C-4 and C-5 may be a double bond in the HexA residue at the non-reduced terminus. That is, for example, 50% or more, 70% or more, 80% or more, 90% or more, 95% or more, 97% or more, 99% or more, or 100% of the HexA residues having a double bond between C-4 and C-5 may be present at the non-reduced terminus. Also, for example, 50% or more, 70% or more, 80% or more, 90% or more, 95% or more, 97% or more, 99% or more, or 100% of the HexA residues not having a double bond between C-4 and C-5 may be present at positions other than the non-reduced terminus. Also, for example, the linkage between C-4 and C-5 may be a double bond in 50% or more, 70% or more, 80% or more, 90% or more, 95% or more, 97% or more, 99% or more, or 100% of the HexA residues at the non-reduced terminus. Also, for example, the linkage between C-4 and C-5 may not be a double bond in 50% or more, 70% or more, 80% or more, 90% or more, 95% or more, 97% or more, 99% or more, or 100% of the HexA residues at positions other than the non-reduced terminus.

$R_1$ represents a hydrogen (—H) or a sulfate group (—$SO_3H$). The percentage of $R_1$ that is the sulfate group may be or may not be identical to that in the IdoA residue and the GlcA residue. The percentage of $R_1$ that is the sulfate group in all of the HexA residues, which also can be referred to as "2-O-sulfation rate of the HexA residues", the percentage of $R_1$ that is the sulfate group in the IdoA residues, which also can be referred to as "2-O-sulfation rate of the IdoA residues", and the percentage of $R_1$ that is the sulfate group in the GlcA residues, which can also be referred to as "2-O-sulfation rate of the GlcA residues", each may be, for example, 0% or more, 5% or more, 10% or more, 15% or more, 20% or more, 30% or more, 40% or more, 50% or more, 60% or more, 70% or more, 80% or more, or 90% or more; and 100% or less, 95% or less, 90% or less, 85% or less, 80% or less, 70% or less, 60% or less, 50% or less, 40% or less, or 30% or less, or a consistent combination thereof. Specifically, the 2-O-sulfation rate of the HexA residues may be, for example, 0% to 80%, 10% to 70% or 15% to 70%. Specifically, the 2-O-sulfation rate of the IdoA residues may be, for example, 0% to 100%, 15% to 100%, or 30% to 100%. Specifically, the 2-O-sulfation rate of the GlcA residues may be, for example, 0% to 50%, 0% to 40% or 0% to 30%. The percentage of $R_1$ that is the sulfate group can be measured by, for example, disaccharide analysis. That is, the 2-O-sulfation rate of the HexA residue can be calculated as a percentage (molar ratio) of the amount of the above disaccharide units where the HexA residue is a 2-O-sulfated HexA residue relative to the total amount of the above disaccharide units when the polysaccharide is subjected to disaccharide analysis. Also, the 2-O-sulfation rate of the IdoA residue can be calculated as a percentage (molar ratio) of the amount of the above disaccharide units where the HexA residue is a 2-O-sulfated IdoA residue relative to the total amount of the above disaccharide units where the HexA residue is the IdoA residue, when the polysaccharide is subjected to disaccharide analysis. Also, the 2-O-sulfation rate of the GlcA residue can be calculated as a percentage (molar ratio) of the amount of the above disaccharide units where the HexA residue is a 2-O-sulfated GlcA residue relative to a total amount of the above disaccharide units where the HexA residue is the GlcA residue, when the polysaccharide is subjected to disaccharide analysis.

$R_2$ represents a hydrogen (—H) or a sulfate group (—$SO_3H$). The percentage of $R_2$ that is the sulfate group may be or may not be identical in the IdoA residues and the GlcA residues. The sulfate group of $R_2$ is not present in naturally occurring heparin. Thus, for example, due to concerns about a possible in vivo side reaction, the percentage of $R_2$ that is the sulfate group should be low. The percentage of $R_2$ that is the sulfate group of all the HexA residues, which can also be referred to as a "3-O-sulfation rate in HexA residues", the percentage of $R_2$ that is the sulfate group in the IdoA residues, which also can be referred to as a "3-O-sulfation rate in IdoA residues", and the percentage of $R_2$ that is the sulfate group in the GlcA residues, which also can be referred to as a "3-O-sulfation rate in GlcA residues", each may be, for example, less than 15%, less than 10%, less than 5%, less than 3%, less than 1%, less than 0.5%, less than 0.1%, or 0%. The percentage of $R_2$ that is the sulfate group can be measured, for example, by disaccharide analysis. That is, the 3-O-sulfation rate in the HexA residues can be calculated as a percentage (molar ratio) of the amount of the above disaccharide units where the HexA residue is a 3-O-sulfated HexA residue relative to the total amount of the above disaccharide units when the polysaccharide is subjected to the disaccharide analysis. Also, the 3-O-sulfation rate in IdoA residues can be calculated as a percentage (molar ratio) of the amount of the above disaccharide units where the HexA residue is a 3-O-sulfated IdoA residue relative to the total amount of the above disaccharide units where the HexA residue is the IdoA residue, when the polysaccharide is subjected to disaccharide analysis. Also, the 3-O-sulfation rate in GlcA residues can be calculated as a percentage (molar ratio) of the amount of the above disaccharide units where the HexA residue is a 3-O-sulfated GlcA residue relative to the total amount of the above disaccharide units where the HexA residue is the GlcA residue, when the polysaccharide is subjected to disaccharide analysis.

$R_3$ represents a hydrogen (—H), a sulfate group (—$SO_3H$) or an acetyl group (—$COCH_3$). At least a portion of the $R_3$ is the sulfate group. The percentage of $R_3$ that is the sulfate group, which can also be referred to as an "N-sulfation rate", in $R_3$ may be, for example, 60% or more, 70% or more, or 80% or more; and 100% or less, 95% or less, or 90% or less, or a combination thereof. Specifically, the N-sulfation rate may be, for example, 70% to 100% or 80% to 95%. A percentage of $R_3$ that is the acetyl group, which can also be referred to as an "N-acetylation rate", may be, for example, 0% or more, 1% or more, 1.5% or more, 3% or more, 5% or more, 7% or more, 9% or more, or 11% or more and 50% or less, 45% or less, 40% or less, 35% or less, 33% or less, 30% or less, 25% or less, 20% or less, or 17% or less, or a combination thereof. Specifically, the N-acetylation rate may be, for example, 0% to 33%, 1% to 33%, 7% to 33%, 7% to 30%, or 11% to 17%. The N-sulfation rate and the N-acetylation rate can be measured, for example, by disaccharide analysis. That is, the N-sulfation rate can be calculated as a percentage (molar ratio) of the amount of the above disaccharide units where the GlcN residue is an N-sulfated GlcN residue relative to the total amount of the above disaccharide units, when the polysaccharide is subjected to disaccharide analysis. Also, the N-acetylation rate can be calculated as a percentage (molar ratio) of the amount of the above disaccharide units where the GlcN residue is an N-deacetylated GlcN residue relative to the total amount of the above disaccharide units, when the polysaccharide is subjected to the disaccharide analysis. The position of the GlcN residue where $R_3$ is a hydrogen, a sulfate group or an acetyl group is not particularly limited. For example, in particular, $R_3$ may be a hydrogen or an acetyl group in the GlcN residue at the reduced terminus. That is, for example, 50% or more, 70 or more, 80 or more, 90 or more, 95 or more, 97 or more, 99 or more, or 100% of the GlcN residues where $R_3$ is a hydrogen or an acetyl group may be present at the reduced terminus.

$R_4$ represents a hydrogen (—H) or a sulfate group (—$SO_3H$). The percentage of $R_4$ that is the sulfate group, which can also be referred to as "3-O-sulfation rate in GlcN residues" or simply "3-O-sulfation rate", is 13% or more. The 3-O-sulfation rate in GlcN residues may be, for example, 45% or less, 40% or less or 33% or less. Specifically, the 3-O-sulfation rate in GlcN residues may be, for example, 13% to 45%, 13% to 40%, or 13% to 33%. The N-sulfation rate of the GlcN residues can be measured, for example, by disaccharide analysis. That is, the N-sulfation rate of the GlcN residues can be calculated as a percentage (molar ratio) of the amount of the above disaccharide units where the GlcN group is a 3-O-sulfated GlcN group relative to the total amount of the above disaccharide units, when the polysaccharide is subjected to disaccharide analysis.

$R_5$ represents a hydrogen (—H) or a sulfate group (—$SO_3H$). At least a portion of $R_5$ is the sulfate group. The percentage of $R_5$ that is the sulfate group, which can also be referred to as "6-O-sulfation rate of the GlcN groups" or simply "6-O-sulfation rate", may be, for example, 50% or more, 60% or more, 70% or more, 80% or more, or 90% or more; and 100% or less, or 95% or less, or a combination thereof. Specifically, the 6-O-sulfation rate may be, for example, 50 to 100%, 60 to 100%, or 70 to 100%. The 6-O-sulfation rate can be measured, for example, by disaccharide analysis. That is, the 6-O-sulfation rate can be calculated as a percentage (molar ratio) of the amount of the above disaccharide units where the GlcN residue is a 6-O-sulfated GlcN residue relative to the total amount of the above disaccharide units, when the polysaccharide is subjected to the disaccharide analysis.

Specifically, the polysaccharide may include, for example, one or more disaccharide units, such as GlcA-GlcN(NS3S6S), GlcA(2S)-GlcN(NS6S), IdoA(2S)-GlcN (NS6S), GlcA-GlcN(NS6S), IdoA(2S)-GlcN(NS), IdoA (2S)-GlcN(NS3S), IdoA-GlcN(NS6S), and/or GlcA-GlcN (NS). The total content rate of GlcA-GlcN(NS3S6S), GlcA (2S)-GlcN(NS6S), IdoA(2S)-GlcN(NS6S), GlcA-GlcN (NS6S), IdoA(2S)-GlcN(NS), IdoA(2S)-GlcN(NS3S), IdoA-GlcN(NS6S), and/or GlcA-GlcN(NS) in the polysaccharide may be, for example, 50% or more, 60% or more, 70% or more, 80% or more, or 90% or more. The total content rate can be measured, for example, by disaccharide analysis. That is, the total content rate can be calculated as a percentage (molar ratio) of the total amount of GlcA-GlcN (NS3S6S), GlcA(2S)-GlcN(NS6S), IdoA(2S)-GlcN(NS6S), GlcA-GlcN(NS6S), IdoA(2S)-GlcN(NS), IdoA(2S)-GlcN (NS3S), IdoA-GlcN(NS6S), and/or GlcA-GlcN(NS) relative to the total amount of the disaccharides, when the polysaccharide is subjected to the disaccharide analysis. In the description of such a disaccharide unit, the position and type of a substituent is written in a parenthesis, and $R_1$ to $R_5$ that is not written in the parenthesis represent a hydrogen (—H).

The polysaccharide has an anticoagulant activity. The anticoagulant activity specifically can mean an anti-blood coagulation activity. The anticoagulant activity can include an anti-factor Xa activity and an anti-factor IIa activity. The polysaccharide may have at least the anti-factor Xa activity. The anti-factor Xa activity in the polysaccharide may be, for example, 100 IU/mg or more, 200 IU/mg or more, 300 IU/mg or more, or 400 IU/mg or more. The anti-factor Xa activity in the polysaccharide particularly has no upper limit, and may be, for example, 5000 IU/mg or less, 2000 IU/mg or less, or 1000 IU/mg or less. Also the polysaccharide may have a high ratio of anti-factor Xa activity/anti-factor IIa activity. The ratio of anti-factor Xa activity/anti-factor IIa activity in the polysaccharide may be, for example, 1.5 or more, 2 or more, 2.5 or more, or 3 or more. Also, the ratio of anti-factor Xa activity/anti-factor IIa activity in the polysaccharide particularly has no upper limit, and may be, for example, 50 or less, 20 or less, or 10 or less. Both the anti-factor Xa activity and the anti-factor IIa activity can be measured by standard methods. Methods for measuring the anti-factor Xa activity and the anti-factor IIa activity can include, for example, methods described in Examples herein.

The polysaccharide may be a free form, a salt form, or a mixture thereof. That is, the term "polysaccharide, for example, heparan sulfate" can mean a free from of the polysaccharide, or a salt form thereof, or a mixture thereof unless otherwise specified. That is, any functional group that is present in the polysaccharide and can form a salt may be a free form, may form a salt, or may be a combination thereof unless otherwise specified. Specifically, for example, any functional group capable of forming a salt in the general formula (I) and the general formula (II) may be a free form, may form a salt, or may be a combination thereof unless otherwise specified. The functional group capable of forming the salt in the general formula (I) and the general formula (II) can include an amino group (—$NH_2$) of the GlcN residue and a carboxyl group (—COOH) of the HexA residue when $R_1$ to $R_5$ are sulfate groups (—$SO_3H$) and $R_3$ is a hydrogen (—H). That is, the term "sulfate group" can refer to a free form of the sulfate group, or the sulfate group that forms a salt, or a combination thereof. This explanation for the sulfate group can apply to other functional groups capable of forming a salt. The salts can include pharmacologically acceptable salts. The pharmacologically acceptable salt can be appropriately chosen depending on various conditions such as utilization aspects of the polysaccharide. The pharmacologically acceptable salts can include the following. Examples of salts for an acidic group such as a sulfate group specifically can include an ammonium salt, a salt with an alkaline metal such as sodium, potassium, and lithium, a salt with an alkaline earth metal such as calcium and magnesium, an aluminum salt, a zinc salt, a salt with organic amine such as triethylamine, ethanolamine, morpholine, pyrrolidine, piperidine, piperazine, and dicyclohexylamine, and a salt with a basic amino acid such as arginine and lysine. Also, examples of salts for a basic group such as an amino group specifically can include a salt with an inorganic acid such as hydrochloric acid, sulfuric acid, phosphoric acid, nitric acid, and hydrobromic acid, a salt with an organic carboxylic acid such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and a salt with organic sulfonic acid such as methanesulfonic acid, benzenesulfonic acid, and p-toluenesulfonic acid. The salt may be, for example, an ammonium salt, a sodium salt, a lithium salt and a calcium salt. As the salt, one salt may be used, or two or more salts may be used in combination.

<2> Method of Producing Polysaccharide

The technique for producing the polysaccharide as described herein is not particularly limited. The polysaccharide can be derived from another polysaccharide, that is, by using the other polysaccharide as a raw material. Other polysaccharides can include glycosaminoglycan (GAG). GAG can include N-acetyl heparosan (also simply referred to as "heparosan") and heparan sulfates other than the polysaccharide. Heparosan is a polysaccharide composed of a repetitive structure of a disaccharide composed of glucuronic acid (GlcA) residue and N-acetyl-D-glucosamine (GlcNAc) residue. The production of the polysaccharide using the other polysaccharide as a raw material can be performed by, for example, a physical technique, a chemical technique, an enzymatic technique, or a combination thereof. Specifically, when using another polysaccharide as a raw material, the polysaccharide can be produced by adjustment to a predetermined molecular weight, isomerization at a predetermined ratio, introduction or removal of a functional group at a predetermined ratio, or a combination thereof. The polysaccharide can be entirely synthesized from monosaccharides and the like as a raw materials.

One example of a method of producing the polysaccharide from heparosan is explained below.

The polysaccharide can be produced, for example, by partially N-deacetylating heparosan followed by treating it with heparinase III to conduct depolymerization, and then converting the produced low molecular weight products into the polysaccharide. That is, the method of producing the polysaccharide can include a method that includes a step (A) of partially N-deacetylating heparosan, a step (B) of treating the product in step (A) with heparinase III to conduct depolymerization, and a step (C) of producing the polysaccharide from the product in step (B). Steps (A), (B) and (C) can also be referred to as "N-deacetylation step", "depolymerization step", and "heparan sulfate production step", respectively. According to this method, in particular, the polysaccharide having a desired average molecular weight can be produced efficiently.

<2-1> Production of Heparosan

Heparosan can be produced by a fermentation method utilizing a bacterium having an ability to produce heparosan (also referred to as a "heparosan producing bacterium") (WO2015/050184)

The "bacterium having the ability to produce heparosan (heparosan-producing bacterium) refers to a bacterium that has an ability to produce heparosan when cultured in a medium and to accumulate heparosan in the medium to the extent that heparosan can recovered. The bacterium having the ability to produce heparosan may be a bacterium that can accumulate heparosan, for example, in an amount of 50 mg/L or more, 100 mg/L or more, 200 mg/L or more, or 300 mg/L or more in the medium.

The type of the bacterium is not particularly limited. The bacterium can include bacteria belonging to genus *Escherichia*. The bacteria belonging to genus *Escherichia* are not particularly limited, and can include bacteria classified into genus *Escherichia* by classification known to microbiological experts. The bacteria belonging to genus *Escherichia* can include, for example, those described in a literature by Neidhardt et al. (Backmann, B. J. 1996. Derivations and Genotypes of some mutant derivatives of *Escherichia coli* K-12, p. 2460-2488. Table 1. In F. D. Neidhardt (ed.), *Escherichia coli* and *Salmonella* Cellular and Molecular Biology/Second Edition, American Society for Microbiology Press, Washington, D.C.). Examples of the bacteria belonging to genus *Escherichia* can include *Escherichia coli*. Examples of *Escherichia coli* can include *Escherichia coli* K-12 strain such as W3110 strain (ATCC 27325) and MG1655 strain (ATCC 47076); *Escherichia coli* K5 strain (ATCC 23506); *Escherichia coli* B strain such as BL21 (DE3) strain, and derivative strains thereof.

These bacterial strains can be purchased from American Type Culture Collection (address: P. O. Box 1549, Manassas, Va. 20108, United States of America). That is, an access number has been given to each bacterial strain, and the bacterial strain can be purchased utilizing this access number (see atcc.org). The access number corresponding to each bacterial strain is listed in the catalogue of American Type Culture Collection. BL21 (DE3) strain is available from, for example, Life Technologies (product number C6000-03).

The bacterium having the ability to produce heparosan may inherently have the ability to produce heparosan or can be modified to have the ability to produce heparosan. The bacterium inherently having the ability to produce heparosan can include *Escherichia coli* K5 strain (ATCC 23506). The bacterium having the ability to produce heparosan can be acquired by imparting the ability to produce heparosan to the bacterium as above. The bacterium inherently having the ability to produce heparosan may be modified to increase the ability to produce heparosan.

The ability to produce heparosan can be imparted by introducing a gene encoding a protein involved in production of heparosan. The protein involved in production of heparosan can include glycosyltransferase and a heparosan efflux carrier protein. One gene may be introduced, or two or more genes may be introduced. Introduction of the gene can be performed similar to the technique for increasing a copy number of a gene described herein.

"Glycosyltransferase" can refer to a protein having an activity to catalyze a reaction in which N-acetyl-D-glucosamine (GlcNAc) and/or glucuronic acid (GlcA) is added to a non-reduced terminus of a sugar chain to extend a heparosan chain. This activity can also be referred to as a "glycosyltransferase activity". The gene encoding glycosyltransferase can include a kfiA gene, a kfiC gene and a pmHS1 gene.

The kfiA gene and the kfiC gene can include the kfiA gene and the kfiC gene native to *Escherichia coli* K5 strain. A KfiA protein encoded by the kfiA gene in *Escherichia coli* K5 strain adds GlcNAc to the non-reduced terminus of the sugar chain using UDP-GlcNAc as a substrate. A KfiC protein encoded by the kfiC gene in *Escherichia coli* K5 strain adds GlcA to the non-reduced terminus of the sugar chain using UDP-GlcA as a substrate. The kfiA gene and the kfiC gene in *Escherichia coli* K5 strain together with a kfiB and kfiD genes make up the KfiABCD operon (also referred to as Region 2). The nucleotide sequence of a region including the KfiABCD operon in *Escherichia coli* K5 strain is shown in SEQ ID NO:1. In the nucleotide sequence shown in SEQ ID NO:1, the kfiA, kfiB, kfiC and kfiD genes correspond to the sequence at positions 445 to 1164, the sequence at positions 1593 to 3284, the sequence at positions 4576 to 6138, and the sequence at positions 6180 to 7358, respectively. Amino acid sequences of the KfiA, KfiB, KfiC and KfiD proteins are shown in SEQ ID NOS:2 to 5.

The pmHS1 gene can include a pmHS1 gene native to *Pasteurella multocida* type D strain. A PmHS1 protein encoded by the pmHS1 gene in *Pasteurella multocida* type D strain alternately adds GlcNAc and GlcA to the non-reduced terminus of the sugar chain using both UDP-GlcNAc and UDP-GlcA as substrates.

The "heparosan efflux carrier protein" can refer to a protein having an activity to excrete the heparosan chain out of a cell through a cell membrane. This activity is also referred to as a "heparosan efflux activity". Genes encoding the heparosan efflux carrier protein can include kpsC, kpsD, kpsE, kpsM, kpsS, and kpsT genes. The kpsC, kpsD, kpsE, kpsM, kpsS, and kpsT genes can include a kpsC, kpsD, kpsE, kpsM, kpsS, and kpsT genes native to the *Escherichia coli* K5 strain and *Escherichia coli* B strain. The KpsC, kpsD, kpsE and KpsS genes in these strains together with a kpsF and kpsU genes make up the kpsFEDUCS operon (also referred to as Region 1). Also, the kpsM and kpsT genes make up the kpsMT operon (also referred to as Region 3).

The gene to be introduced can be appropriately chosen depending on the chosen bacterium. That is, the ability to produce heparosan can be imparted to a bacterium by modifying the bacterium to have both the gene encoding glycosyltransferase and the gene encoding the heparosan efflux carrier protein. For example, *Escherichia coli* B strain has the gene encoding the heparosan efflux carrier protein, but does not have the gene encoding glycosyltransferase. Thus, the ability to produce heparosan can be imparted to *Escherichia coli* B strain by introducing the gene encoding glycosyltransferase. Also, for example, the *Escherichia coli* K-12 strain has neither the gene encoding glycosyltransferase nor the gene encoding the heparosan efflux carrier protein. Thus, the ability to produce heparosan can be imparted to *Escherichia coli* K-12 strain by introducing both the gene encoding glycosyltransferase and the gene encoding the heparosan efflux carrier protein.

That is, examples of genus *Escherichia* bacteria having the ability to produce heparosan can include *Escherichia coli* K5 strain; strains obtained by introducing the kfiA gene and the kfiC gene native to *Escherichia coli* K5 strain into *Escherichia coli* B strain such as BL21 (DE3); strains obtained by introducing the kfiA gene and the kfiC gene native to *Escherichia coli* K5 strain and the kpsC, kpsD, kpsE, kpsM, kpsS, and kpsT genes native to *Escherichia coli* K5 strain or *Escherichia coli* B strain into *Escherichia coli* K-12 strain such as W3110 strain and MG1655 strain; and derivative strains thereof. Examples of the strain obtained by introducing the kfiA gene and the kfiC gene native to *Escherichia coli* K5 strain into *Escherichia coli* B strain specifically can include *Escherichia coli* BL21 (DE3)/pVK9-kfiABCD (WO2015/050184).

Also, the bacterium having the ability to produce heparosan may be modified so as to enhance the expression of native gene(s), among the genes encoding proteins involved in production of heparosan. That is, for example, the *Escherichia coli* K5 strain may be modified so that the expression of one or more genes encoding a protein involved in the production of heparosan is enhanced. Also, for example, the *Escherichia coli* B strain may be modified so that the expression of one or more genes encoding the heparosan efflux carrier protein is enhanced.

Also, as long as the ability to produce heparosan is not impaired, other modifications may be made to the bacterium having the ability to produce heparosan. For example, the bacterium having the ability to produce heparosan may be modified so that the expression of one or more of the kfiB, kfiD, kpsF, and kpsU genes is/are enhanced. That is, for example, when the gene encoding glycosyltransferase is introduced, Region 2 may be collectively introduced, and when the gene encoding glycosyltransferase and the gene encoding the heparosan efflux carrier protein are introduced, Regions 1 to 3 may collectively be introduced. The kfiB gene and the kfiD gene can include the kfiB gene and the kfiD gene in *Escherichia coli* K5 strain. The kpsF gene and the kpsU gene can include the kpsF gene and the kpsU gene in *Escherichia coli* K5 strain and *Escherichia coli* B strain.

The bacterium having the ability to produce heparosan may be modified so that the expression of one or more of the following genes is/are enhanced: rbsR, rbsK, rbsB, hsrA, glgB, lgX, micF, rcsD, rcsB, ybiX, ybiI, ybiJ, ybiC, ybiB, rfaH, nusG, pcoR, pcoS, pcoE, yhcN, yhcO, aaeB, aaeA, aaeX, g1455, alpA, g1453, yrbA, mlaB, mlaC, mlaD, mlaE, mlaF, yrbG, norW, ybjI, ybjJ, ybjK, rybB, yjjY, yjtD, thrL, thrA, thrB, fruA, psuK, ytfT, yjfF, fbp, yagU, paoA, paoB, gsiC, gsiD, yliE, irp2, irp1, bhsA, ycfS, lepB, rnc, era, dapA, gcvR, bcp, hyfA, rpoE, nadB, yfiC, srmB, g1414, g1413, nuoE, nuoF, nuoG, glmZ, hemY, hemX, hemD, rlmL, artQ, artM, artJ, rlmC, ybjO, yejO, yejM, yejL, rpoS, ygbN, ygbM, ygbL, g3798, g3797, g3796, g3795, g3794, g3793, g3792, ryjA, soxR, soxS, yjcC, yjcB, efeU, efeO, slyA, hns, pgm, galF, ugd, glmU, glmS, glmM, and rcsA (WO2015/050184, Journal of Technical Disclosure No. 2015-501775). These genes can include genes native to *Escherichia coli* such as *Escherichia coli* K-12 MG1655 strain, BL21 (DE3) strain, and K5 strain, and genes native to other various bacteria.

The phrase "the expression of a gene is enhanced" encompasses not only increasing the expression amount of the target gene in a bacterial strain that originally expresses the target gene, but also expressing the target gene in a bacterial strain that does not originally express the target gene. That is, "the expression of a gene is enhanced" encompasses, for example, introducing a target gene into a bacterial strain that does not originally express the target gene and expressing the target gene. The expression of the gene can be enhanced by, for example, increasing a copy number of the gene and increasing transcription and translation of the gene. The copy number of the gene can be increased by introducing a vector into which the gene has been inserted into a host or introducing the gene onto a chromosome of the host. The gene to be introduced can be obtained by cloning it from an organism to which the gene is native, or by chemically synthesizing it. The obtained gene can be utilized in its original state or with appropriate modifications. The transcription and translation of the gene can be increased by modifying an expression regulating sequence of the gene such as promotors and SD sequences.

Nucleotide sequences of genes used for the modification of bacteria, such as by imparting the ability to produce heparosan, and amino acid sequences of proteins encoded by such genes can be obtained from public databases such as NCBI (ncbi.nlm.nih.gov) and references such as WO2015/050184 and Journal of Technical Disclosure No. 2015-501775.

The genes used for modification of bacteria, such as by imparting the ability to produce heparosan, are not limited to the genes exemplified above and the genes having a known nucleotide sequence, but may be variants of these genes as long as the gene encodes a protein that maintains its original function. The variants can include homologs and artificially modified genes of the known genes. The phrase "maintaining its original function" can refer to a variant of a protein having a glycosyltransferase activity in the case of the function of glycosyltransferase, and a variant of a protein having a heparosan efflux carrier activity in the case of the function of the heparosan efflux carrier protein. For example, the genes used for the modification of bacteria, such as by imparting the ability to produce heparosan, may be genes encoding proteins having an amino acid sequence having one or several, that is, for example, 1 to 50, 1 to 40, 1 to 30, 1 to 20, 1 to 10, 1 to 5, or 1 to 3 amino acid substitutions, deletions, insertions, or additions at one or several positions in an amino acid sequence of a known protein. For example, the genes used for the modification of bacteria, such as by imparting the ability to produce heparosan, may be genes encoding proteins having, for example, 50% or more, 65% or more, 80% or more, 90% or more, 95% or more, 97% or more, and or 99% or more identity to the amino acid sequence of the known protein. The description for such variants can apply to other proteins such as heparinase III and genes encoding them.

Heparosan can be accumulated in a medium by culturing a heparosan-producing bacterium. Culture conditions for the heparosan-producing bacterium are not particularly limited as long as the desired amount of heparosan is obtained. The culture conditions of the heparosan-producing bacterium can be appropriately configured depending on various conditions such the chosen host and expression system for the gene involved in heparosan production. Cultivation can be performed aerobically, for example, using a liquid medium containing various organic ingredients and inorganic ingredients such as a carbon source, a nitrogen source, and trace nutrition, at 30 to 37° C. for 16 to 72 hours (WO2015/050184).

Heparosan may be subjected to an N-deacetylation step while being included in a culture solution, or may be recovered from the culture solution followed by being subjected to the N-deacetylation step. The procedure for recovering heparosan from the culture solution is not particularly limited. The procedure for recovering heparosan can include known techniques used for separation and purification of a compound, such as a membrane treatment method and a precipitation method. For example, heparosan in a culture supernatant can be precipitated and recovered by separating the supernatant from the culture solution and then adding a water-miscible organic solvent such as ethanol or methanol (WO2015/050184). The amount of the organic solvent to be added may be 2.5 to 3.5 times the amount of the supernatant. Heparosan may be appropriately subjected to treatment such as purification, dilution, concentration, drying, and dissolution, followed by being subjected to the N-deacetylation step. The purification may be performed to the desired extent. These treatments may be performed alone or in combination as appropriate.

<2-2> N-deacetylation Step

The N-deacetylation step is a step in which heparosan is partially N-deacetylated. Partially N-deacetylated heparosan is produced by N-deacetylation step. A product of the N-deacetylation step (partially N-deacetylated heparosan) can also be referred to as "N-deacetylated heparosan". "Heparosan is partially N-deacetylated" can refer to N-deacetylating heparosan so that some of the N-acetyl groups of heparosan remain. By allowing some of the N-acetyl groups of heparosan to remain, a site of a glucosamine residue having the N-acetyl group can be preferentially cleaved in a depolymerization step, and the polysaccharide having the desired average molecular weight can be produced efficiently. The degree of the N-deacetylation is not particularly limited as long as the polysaccharide can be produced. The N-deacetylation step can be performed so that the residual rate of the N-acetyl group or degree of N-deacetylation is the following value. That is, the residual rate of the N-acetyl group may be, for example, 1% or more, 1.5% or more, 3% or more, 5% or more, 7% or more, 9% or more, or 11% or more; and 50% or less, 45% or less, 40% or less, 35% or less, 33% or less, 30% or less, 25% or less, 20% or less, or 17% or less, or a combination thereof. Specifically, the residual rate of the N-acetyl group may be for example, 1% to 33%, 7% to 33%, 7% to 30%, or 11% to 17%. For example, the residual rate of the N-acetyl group of 7% to 30% approximately corresponds to a state where the N-acetyl groups are present at a rate of one N-acetyl group per 6 to 28 sugar residues (one per 3 to 14 units as a disaccharide unit). Also for example, the residual rate of the N-acetyl group of 11% to 17% approximately corresponds to a state where the N-acetyl groups are present at a rate of one N-acetyl group per 12 to 18 sugar residues (one per 6 to 9 units as a disaccharide unit). The degree of N-deacetylation, that is, the residual rate of the N-acetyl groups, can be confirmed, for example, by the disaccharide analysis. The residual rate of the N-acetyl groups can be measured as the aforementioned N-acetylation rate.

Residual N-acetyl groups may be appropriately removed after the depolymerization step. For example, further N-deacetylation may be performed, or further N-deacetylation and N-sulfation may be performed at any time after the depolymerization step.

The procedure for performing the N-deacetylation step is not particularly limited as long as the desired degree of N-deacetylation is obtained. The N-deacetylation step can be performed chemically using a deacetylation agent. The deacetylation agent can include sodium hydroxide and hydrazine.

As conditions for N-deacetylation utilizing sodium hydroxide, for example, the previously reported conditions (Kuberan B. et al., (2003) "Chemoenzymatic Synthesis of Classical and Non-classical Anticoagulant Heparan Sulfate Polysaccharides." J. Biol. Chem., 278 (52): 52613-52621. and US2011281820A1) can be referenced. That is, N-deacetylation can be performed by dissolving heparosan in an aqueous solution of sodium hydrogen and heating it. The concentration, reaction temperature, and reaction time period of each component in the reaction system can be appropriately configured so that the desired degree of N-deacetylation is obtained. The concentration of heparosan may be, for example, 0.05% (w/v) to 50% (w/v). The concertation of sodium hydroxide may be, for example, 1 M to 5 M. The reaction temperature may be, for example, 40 to 80° C. The reaction time period may be, for example, 5 minutes to 30 hours.

As conditions for N-deacetylation utilizing hydrazine, for example, the previously reported conditions (Glycobiology, 10 (2000) 159-171, Carbohydrate Research, 290 (1996) 87-96, Biochem. J. 217 (1984) 187-197) can be referenced. Also the conditions for N-deacetylation utilizing hydrazine specifically can include, for example, the conditions described in the Examples herein. That is, the N-acetylation can be performed, for example, by dissolving heparosan in an aqueous solution of hydrazine containing sulfuric acid or hydrazine sulfate, replacing the gas phase with an inert gas such as nitrogen, and heating it. Hydrazine can include hydrazine anhydrate and hydrazine monohydrate. For example, hydrazine monohydrate may be utilized directly or by appropriately diluting as an aqueous solution of hydrazine. After heating, the reaction can be stopped with ice-cooling. Then the terminus of the sugar chain can be reduced with iodine. The concentration, reaction temperature, and reaction time period of each component in the reaction system can be appropriately configured so that a desired degree of the N-deacetylation is obtained. The concentration of heparosan may be, for example, 0.05% (w/v) to 50% (w/v). The concentration of hydrazine may be, for example, 10% (w/v) to 70% (w/v). The concentration of sulfuric acid or hydrazine sulfate may be, for example, 0.01 M to 0.1 M. The reaction temperature may be, for example, 60 to 118° C.

The reaction time period may be, for example, 5 minutes to 20 hours. Specifically for example, when the N-deacetylation is performed under the conditions described in the Examples herein, the reaction time period may be, for example, 4 to 5 hours.

N-deacetylated heparosan is produced by performing the N-deacetylation in this way. N-deacetylated heparosan may be subjected to the depolymerization step in the reaction solution at the N-deacetylation step, or may be recovered from the reaction solution and then subjected to the depolymerization step. The procedure for recovering N-deacetylated heparosan from the reaction solution is not particularly limited. The procedure for recovering N-deacetylated heparosan can include known techniques used for separation and purification of a compound, such as a membrane treatment method and a precipitation method. N-deacetylated heparosan may be appropriately subjected to treatments such as purification, neutralization, desalting, dilution, concentration, drying, and dissolution, followed by the depolymerization step. The purification may be performed to the desired extent. These treatments may be performed alone or in combination as appropriate.

<2-3> Depolymerization Step

The depolymerization step is a step where N-deacetylated heparosan is cleaved with heparinase III to make small molecules. Low-molecularized N-deacetylated heparosan is produced by the depolymerization step. The product of the depolymerization step (low-molecularized N-deacetylated heparosan) can also be referred to as "low molecular weight N-deacetylated heparosan". The degree of depolymerization is not particularly limited as long as the polysaccharide as described herein can be produced. The depolymerization step can be performed, for example, so that the average molecular weight of low molecular weight N-deacetylated heparosan is the average molecular weight of the polysaccharide as described herein (e.g., a number average molecular weight (Mn) of 1000 to 150000, or 8000 to 60000 and a weight average molecular eight (Mw) of 2000 to 300000, or 10000 to 100000 as measured by GPC using pullulan as a standard).

The degree of the depolymerization can be confirmed, for example, by measuring its molecular weight. Measurement of the molecular weight can be performed by a standard method. Methods for measuring the molecular weight can include gel permeation chromatography (GPC), and aqueous size exclusion chromatography (SEC) using a ultraviolet and visible light absorbance detector (UV) and a refractive index detector (RI) (SEC-RI/UV method; according to the European Pharmacopeia (EP)). Specifically, conditions for measuring the molecular weight by GPC can include, for example, the conditions described in the Examples herein. The number average molecular weight (Mn) of depolymerized N-deacetylated heparosan may be, for example, 1000 to 150000, 3000 to 36000, or 4000 to 26000, or 5000 to 36000, or 12000 to 26000 as measured by GPC using pullulan as a standard. The weight average molecular weight (Mw) of depolymerized N-deacetylated heparosan may be, for example, 2000 to 300000, 5000 to 60000, 6000 to 70000, or 9000 to 35000, or may be 7000 to 60000, or 17000 to 35000 as measured by GPC using pullulan as a standard. The molecular weight can be measured to confirm a degree of the depolymerization after performing some or all of the steps of producing heparan sulfate such as the step of sulfation described later. When the molecular weight is measured after performing some or all of steps of producing heparan sulfate, variation of the molecular weight depending on the performed step can be considered. When a molecular weight of a product is measured after performing some or all of steps of producing heparan sulfate, the number average molecular weight (Mn) of the product may be 1000 to 150000, 2000 to 100000, 4000 to 80000, 7000 to 42000 or 15000 to 30000, and the weight average molecular weight (Mw) of the product may be 2000 to 300000, 5000 to 150000, 5000 to 100000, 8000 to 70000, 8000 to 41000, or 21000 to 41000 as values measured by GPC using pullulan as a standard.

"Heparinase III" can refer to an enzyme (typically EC 4.2.2.8) that cleaves the site of N-sulfated or N-deacetylated glucosamine residue of glycosaminoglycan such as heparosan. Heparinase III is not particularly limited as long as it can preferentially cleave the site of a glucosamine residue having an N-acetyl group in N-deacetylated heparosan. The phrase "cleaving preferentially the site of the glucosamine residue having the N-acetyl group" can refer to cleaving the site of the glucosamine residue having the N-acetyl group more preferentially than the site of the glucosamine residue having no N-acetyl group. The phrase "cleaving preferentially the site of the glucosamine residue having the N-acetyl group" may mean that the site of the glucosamine residue having the N-acetyl group is cleaved but the site of the glucosamine residue having no N-acetyl group is not substantially cleaved. Cleaving the site of the glucosamine residue can refer to cleaving α-1,4-glycoside linkage between the glucosamine residue and a glucuronic acid (GlcA) residue downstream thereof (on a side of the reduced terminus).

The origin of heparinase III is not particularly limited, and heparinase may be native to any microorganism, animal or plant. Variants such as homologs and artificially modified enzymes of known heparinase III may be utilized as heparinase III. Specifically, heparinase III can include bacterial heparinase III native to *Flavobacterium heparinum, Bacteroides thetaiotaomicron, Bacteroides eggerthii*, and the like. A nucleotide sequence of a hepC gene encoding heparinase III in *Flavobacterium heparinum* ATCC 13125 and an amino acid sequence of heparinase III (HepC) are shown in SEQ ID NOS:16 and 17, respectively.

Heparinase III can be produced by allowing a host having a gene encoding heparinase III (heparinase III gene) to express the gene. The host having the heparinase III gene can also be referred to as a host having heparinase III. The host having the heparinase III gene may inherently having the heparinase III gene or may be modified to have the heparinase III gene. The host inherently having the heparinase III gene can include the above bacteria to which heparinase III is native. The host modified to have the heparinase III gene can include a host in which the heparinase III gene has been introduced. The host into which the heparinase III gene is introduced is not particularly limited as long as it can express functional heparinase III. The host can include bacteria, actinomycetes, yeasts, fungi, plant cells, insect cells and animal cells. The bacteria can include Enterobacteriaceae bacteria and coryneform group of bacteria. Enterobacteriaceae bacteria can include the genus *Escherichia* bacteria such as *Escherichia coli*. The coryneform group of bacteria can include the genus *Corynebacterium* bacteria such as *Corynebacterium glutamicum*. The host inherently having the heparinase III gene may be modified to enhance the expression of the heparinase III gene. The heparinase III gene can be expressed and a culture containing heparinase III is obtained by culturing the host having the heparinase III gene. Conditions for culturing the host can be appropriately configured depending on various conditions such as the chosen host and expression system of the heparinase III gene.

Heparinase III can also be produced by expressing the heparinase III gene in a cell free protein synthesis system.

Also, a commercially available heparinase III can be used.

Heparinase III contained in the culture solution and the like may directly be used or heparinase III may be used after recovering it from the culture solution and the like. That is, purified heparinase III (purified enzyme) may be used, or any fraction containing heparinase III may be used as heparinase III. The recovery of heparinase III can be performed by a known technique for separation and purification of proteins. Heparinase III may be purified to a desired extent. Heparinase III may be utilized in a free state or in a state where the enzyme is immobilized to a solid phase such as a resin. The fraction containing heparinase III is not particularly limited as long as the heparinase III fraction is able to act upon N-deacetylated heparosan. The fraction containing heparinase III can include a culture of a host having the heparinase III gene, a microbial cell collected from the culture (cultured microbial cell), a disrupted product of the microbial cell, a lysed product of the microbial cell, an extracted product of the microbial cell (cell free extract solution), a treated microbial cell such as an immobilized microbial cell obtained by immobilizing the microbial cell to a carrier such as acrylamide or carrageenan, a culture supernatant collected from the culture, and a partially purified product thereof (crude purified product). These fractions each may be utilized alone or in combination with purified heparinase III.

The depolymerization step can be performed by allowing heparinase III to act upon N-deacetylated heparosan. Specifically, allowing heparinase III to act upon N-deacetylated heparosan can be accomplished by allowing heparinase III and N-deacetylated heparosan to coexist in a reaction solution. That is, the depolymerization step can be performed in an appropriate reaction solution. The depolymerization step may be performed by a batch system or a column system. In the batch system, for example, the depolymerization step can be performed by mixing heparinase III and N-deacetylated heparosan in the reaction solution in a reaction container. The depolymerization step may be performed by leaving it to stand or performed with stirring or shaking. In the column system, for example, the depolymerization step can be performed by passing a reaction solution containing N-deacetylated heparosan through a column packed with immobilized microbial cells or an immobilized enzyme. The reaction solution can include aqueous media (aqueous solvent) such as water and aqueous buffers.

The reaction solution may contain, if necessary, a component other than N-deacetylated heparosan in addition to N-deacetylated heparosan. The component other than N-deacetylated heparosan can include metal ions and pH buffering agents. The type and concentration of the component in the reaction solution can be appropriately configured depending on various conditions such as the chosen heparinase III.

Conditions, such as the pH of the reaction solution, reaction temperature, reaction time period, concentration of each component and the like. are not particularly limited as long as the desired degree of the depolymerization is obtained. That is, the reaction conditions can be appropriately configured so that the desired degree of the depolymerization is obtained. Specifically, the reaction conditions can include, for example, the conditions described in the Examples herein. The concentration of N-deacetylated heparosan in the reaction solution may be, for example, 0.05% (w/v) to 50% (w/v). The concentration of heparinase III in the reaction solution may be, for example, 6.3 IU/L to $6.3\times10^4$ IU/L or $6.3\times10^1$ IU/L to $6.3\times10^3$ IU/L. The pH value in the reaction solution may typically be, for example, 6.0 to 10.0, or 6.5 to 9.0. The reaction temperature may typically be, for example, 15 to 50° C., 15 to 45° C., or 20 to 40° C. The reaction time period may typically be, for example, 5 minutes to 20 hours, or 10 minutes to 10 hours. Specifically for example, when the depolymerization is performed under the conditions described in the Examples herein, the reaction time period may be 5 to 10 hours. In the case of the column system, a liquid passage speed of the reaction solution may be, for example, a speed so that the reaction time period is within the reaction time period exemplified above.

The activity of heparinase III can be measured, for example, based on production of an unsaturated hexuronic acid in a dependent manner on the enzyme and a substrate in an enzymatic reaction performed at pH 7.0 and 37° C. using heparosan as a substrate. The production of the unsaturated hexuronic acid can be measured as the increase in A232 nm. The amount of the enzyme that produces the unsaturated hexuronic acid of 1 μmol per minute is defined as one international unit(IU).

Heparinase III, N-deacetylated heparosan and the other component may additionally be supplied alone or in any combination to the reaction solution in the process of the depolymerization step. These components may be supplied once or multiple times, or may be supplied continuously.

Also, the reaction conditions may be uniform from start to finish of the depolymerization step, or may be changed during the depolymerization step. That "the reaction conditions are changed during the depolymerization step" can include not only that the reaction conditions are changed temporally but also that the reaction conditions are changed spatially. That "the reaction conditions are changed spatially" can mean, for example, that the reaction conditions such as the reaction temperature and an enzyme concentration and the like are different depending on the position on the flow path when the depolymerization step is performed in the column system.

Depolymerized N-deacetylated heparosan is produced by performing the depolymerization step in this way. Depolymerized N-deacetylated heparosan in the reaction solution of the depolymerization step may directly be subjected to a heparan sulfate production step, or may be recovered from the reaction solution and then subjected to the heparan sulfate production step. The procedure for recovering depolymerized N-deacetylated heparosan is not particularly limited. The procedure for recovering depolymerized N-deacetylated heparosan can include known techniques used for the separation and purification of the compound, such as the membrane treatment method and the precipitation method. Depolymerized N-deacetylated heparosan may be appropriately subjected to treatments such as purification, dilution, concentration, drying, and dissolution, and then subjected to the heparan sulfate production step. The purification may be performed to a desired extent. These treatments may be performed alone or in combination as appropriate.

<4> Heparan Sulfate Production Step

The heparan sulfate production step is a step of producing the polysaccharide from depolymerized N-deacetylated heparosan. The heparan sulfate production step may include one or more, for example, or all of the steps of N-sulfation, C5-epimerization, 2-O-sulfation, 3-O-sulfation in GlcN residues, and 6-O-sulfation of depolymerized N-deacetylated heparosan. Types of steps included in the heparan sulfate production are not particularly limited as long as the polysaccharide is obtained. That is, the types of the steps included in the heparan sulfate production can be appropriately configured depending on the structure of the polysaccharide. The heparan sulfate production step may include, for example, at least the steps of N-sulfation, 3-O-sulfation in GlcN residues and 6-O-sulfation.

The order of performing the respective steps included in the heparan sulfate production is not particularly limited as long as the polysaccharide is obtained. The order of performing the respective steps included in the heparan sulfate production can be appropriately configured depending on various conditions such as the procedure for performing the respective steps and the substrate specificity of enzymes used in respective steps. The steps included in the heparan sulfate production may each be performed separately or may not. That is, some or all of the steps included in the heparan sulfate production step may simultaneously be performed in some or all of the time period.

The heparan sulfate production may be performed in the order of the following steps:

(C1) N-sulfation (C3) 3-O-sulfation in GlcN residues and 6-O-sulfation.

The heparan sulfate production may also be performed in the order of the following steps:

(C1) N-sulfation (C2) C5-epimerization and 2-O-sulfation (C3) 3-O-sulfation in GlcN residues and 6-O-sulfation Step C2 may be performed in the order of C5-epimerization and 2-O-sulfation, or may be performed in the order of 2-O-sulfation and C5-epimerization. In step C2, C5-epimerization and 2-O-sulfation may be performed simultaneously in some or all of the reaction time period.

Step C3 may be performed in the order of 3-O-sulfation in GlcN residues and 6-O-sulfation, or may be performed in the order of 6-O-sulfation and 3-O-sulfation in GlcN residues.

Hereinafter, unless otherwise specified, each step is explained on the assumption that the heparan sulfate production is performed in the order of N-sulfation, C5-epimerization, 2-O-sulfation, 3-O-sulfation in GlcN residues, and 6-O-sulfation. When the type of steps included in the heparan sulfate production step and the order of performing respective steps are different from the above, the explanation can be appropriately read depending on the type of the selected step and the configured order of performing the steps.

The N-sulfation is a step of sulfating an amino group in depolymerized N-deacetylated heparosan. The N-sulfation can be performed chemically using a sulfation reagent. The sulfation reagent can include sulfur trioxide complex such as sulfur trioxide pyridine complex ($PySO_3$) and sulfur trioxide trimethylamine complex ($TMASO_3$). The reaction conditions for the N-sulfation can be appropriately configured by a person of ordinary skill in the art. As reaction conditions for the N-sulfation, the previously reported conditions (Kuberan B. et al., (2003) "Chemoenzymatic Synthesis of Classical and Non-classical Anticoagulant Heparan Sulfate Polysaccharides." J. Biol. Chem., 278 (52): 52613-52621.; U.S. Pat. No. 8,227,449B2 (Jul. 24, 2012)) can be referenced. Specifically, the reaction conditions for the N-sulfation can include, for example, the conditions described in the Examples herein. The degree or rate of the N-sulfation is not particularly limited as long as the polysaccharide is obtained. That is, the N-sulfation can be performed so that the N-sulfation rate exemplified above is obtained. Also, the N-sulfation can be performed so that 90% or more, 95% or more, 99% or more, or all of the N-deacetylated glucosamine residues is N-sulfated. The degree of the N-sulfation, that is, the N-sulfation rate can be confirmed, for example, by disaccharide analysis.

The C5-epimerization is a step of isomerizing the glucuronic acid (GlcA) residue in the N-sulfated product to the iduronic acid (IdoA) residue. The C5-epimerization can be performed enzymatically by utilizing C5-epimerase. C5-epimerase is not particularly limited as long as it can catalyze the isomerization of the glucuronic acid (GlcA) residue to the iduronic acid (IdoA) residue. Also, depending on the order of the C5-epimerization and the other steps, C5-epimerase having an adequate substrate specificity may be selected and used. C5-epimerase may be native to an animal, plant, microorganism, and the like. For example, human C5-epimerase can be utilized as C5-epimerase. Also, variants such as homologs and artificially modified enzymes of known C5-epimerase may be utilized as C5-epimerase. The description for production methods and utilization aspects for heparinase III can apply to production methods and utilization aspects for C5-epimerase. Reaction conditions for the C5-epimerization can be appropriately configured by a person of ordinary skill in the art. As reaction conditions for the C5-epimerization, the previously reported conditions (Chen J, et al., "Enzymatic redesigning of biologically active heparan sulfate." J. Biol. Chem. 2005 Dec. 30; 280(52): 42817-25) can be referenced. Specifically, the reaction conditions for the C5-epimerization can include, for example, the conditions described in the Examples herein. The degree of the C5-epimerization is not particularly limited as long as the polysaccharide is obtained. That is, the C5-epimerization can be performed so that the epimerization rate exemplified above is obtained.

The 2-O-sulfation is a step of sulfating position 2-0 in the IdoA residue in the product by the C5-epimerization. The 2-O-sulfation can be performed enzymatically by utilizing a 2-O-sulfation enzyme (2-OST). 2-OST is not particularly limited as long as it can catalyze the sulfation at position 2-0 of the IdoA residue. 2-OST may further be able to catalyze the sulfation at position 2-0 of the GlcA residue. 2-OST may further be able to catalyze the sulfation at position 2-0 of the HexA residue where a linkage between C4 and C5 is a double bond. Also, 2-OST having an adequate substrate specificity may be selected and used depending on the order of the 2-O-sulfation and the other steps. 2-OST may be native to an animal, plant, microorganism, and the like. For example, hamster 2-OST can be utilized as 2-OST. Also variants such as homologs and artificially modified enzymes of known 2-OST may be utilized as 2-OST. The description for production methods and utilization aspects for heparinase III can apply to production methods and utilization aspects for 2-OST. Reaction conditions for the 2-O-sulfation can be appropriately configured by a person of ordinary skill in the art. As reaction conditions for the 2-O-sulfation, the previously reported conditions (Chen J, et al., "Enzymatic redesigning of biologically active heparan sulfate." J. Biol. Chem. 2005 Dec. 30; 280(52): 42817-25.) can be referenced. Specifically, the reaction conditions for the 2-O-sulfation can include for example, the conditions described in the Examples herein. The degree of the 2-O-sulfation is not particularly limited as long as the polysaccharide is obtained. That is, the 2-O-sulfation can be performed so that the 2-O-sulfation rate exemplified above is obtained.

The isomerization of the GlcA residue to the IdoA residue by C5-epimerase is a reversible equilibrated reaction. That is, when the C5-epimerization is performed utilizing C5-epimerase, a portion of the IdoA residues produced by the C5-epimerization can be converted to the GlcA residues again. On the other hand, 2-O-sulfated hexuronic acid (HexA) residue is generally not a substrate of C5-epimerase. Thus, for example, by coupling the C5-epimerization and the 2-O-sulfation, the IdoA residue produced by the C5-epimerization can be 2-O-sulfated sequentially, and as a result the conversion of the IdoA residue back to the GlcA residue can be prevented. Therefore, the C5-epimerization rate can be enhanced by coupling the C5-epimerization and the 2-O-sulfation. In this way, the C5-epimerization and the 2-O-sulfation may simultaneously be performed during a portion of or for the entire reaction time period. For example, the C5-epimerization and the 2-O-sulfation can collectively be performed by allowing a the products of N-sulfation, C5-epimerase and 2-OST to coexist in the reaction system. Specifically, conditions for a coupled reaction of the C5-epimerization and the 2-O-sulfation can include the conditions described in the Examples herein.

The 6-O-sulfation is a step of sulfating the position 6-0 of an N-sulfated glucosamine (GlcNS) residue in a product produced by the 2-O-sulfation.

The 6-O-sulfation can be performed by using, for example, a 6-O-sulfation enzyme (6-OST). 6-OST is not particularly limited as long as it can catalyze the sulfation at position 0-6 in the N-sulfated glucosamine (GlcNS) residue. 6-OST having an adequate substrate specificity may be selected and used depending on the order of the 6-O-sulfation and the other steps. 6-OST may be native to an animal, plant, microorganism, and the like. 6-OST can include 6-OST-1, 6-OST-2 and 6-OST-3. For example, hamster 6-OST-1 and mouse 6-OST-3 can be utilized as 6-OST. Also variants such as homologs and artificially modified enzymes of known 6-OST may be utilized as 6-OST. The description for production methods and utilization aspects for heparinase III can apply to production methods and utilization aspects for 6-OST. Reaction conditions for the 6-O-sulfation can be appropriately configured by a person of ordinary skill in the art. As reaction conditions for the 6-O-sulfation, the previously reported conditions (Chen J, et al., "Enzymatic redesigning of biologically active heparan sulfate." J. Biol. Chem. 2005 Dec. 30; 280(52): 42817-25.) can be referenced.

The 6-O-sulfation can also be performed chemically by utilizing a sulfation reagent. The sulfation reagent can include sulfur trioxide complex such as sulfur trioxide pyridine complex ($PySO_3$) and sulfur trioxide trimethylamine complex ($TMASO_3$). Reaction conditions for the 6-O-sulfation can be appropriately configured by a person of ordinary skill in the art. As reaction conditions for the 6-O-sulfation utilizing the sulfation reagent, the previously reported conditions (U.S. Pat. No. 8,227,449B2 (Jul. 24, 2012)) can be referenced. Specifically, the reaction conditions for the 6-O-sulfation utilizing the sulfation reagent can include, for example, the conditions described in the Examples herein. The 6-O-sulfation utilizing the sulfation reagent can be performed in an organic solvent such as N,N-dimethylformamide (DMF). The reaction temperature in the 6-O-sulfation may be, for example, −20° C. to 5° C., or −20° C. to 0° C. The amount of the sulfation reagent used for the 6-O-sulfation may be, for example, 1.5 to 10 molar equivalents, or 2 to 5 molar equivalents relative to an amount of a hydroxyl group targeted by the 6-O-sulfation.

The degree or rate of the 6-O-sulfation is not particularly limited as long as the polysaccharide is obtained. That is, the 6-O-sulfation can be performed so that the 6-O-sulfation rate exemplified above is obtained.

The 3-O-sulfation in GlcN residues is a step of sulfating position 3-O of the glucosamine residues that are N-sulfated and 6-O-sulfated in a product by the 6-O-sulfation. The 3-O-sulfation in GlcN residues can be performed enzymatically by utilizing a 3-O-sulfation enzyme (3-OST). 3-OST is not particularly limited as long as it can catalyze the sulfation at position O-3 of the N-sulfated 6-O-sulfated glucosamine residue. 3-OST having an adequate substrate specificity may be used depending on the order of the 3-O-sulfation in GlcN residues and the other steps. 3-OST may be native to an animal, plant, microorganism, and the like. 3-OST can include 3-OST-1, 3-OST-2, 3-OST-3, 3-OST-4, and 3-OST-5. For example, 3-OST-1 from a mouse can be utilized as 3-OST. Also variants such as homologs and artificially modified enzymes of known 3-OST may be utilized as 3-OST. The description for production methods and utilization aspects for heparinase III can apply to production methods and utilization aspects for 3-OST. Reaction conditions for the 3-O-sulfation in GlcN residues can be appropriately configured by a person of ordinary skill in the art. As reaction conditions for the 6-O-sulfation of the GlcN residue, the previously reported conditions (Chen J, et al., "Enzymatic redesigning of biologically active heparan sulfate." J. Biol. Chem. 2005 Dec. 30; 280 (52): 42817-25.) can be referenced. Specifically, the reaction conditions for the 3-O-sulfation in GlcN residues can include, for example, the conditions described in the Examples herein. The degree or rate of the 3-O-sulfation in GlcN residues is not particularly limited as long as the polysaccharide is obtained. That is, the 3-O-sulfation in GlcN residues can be performed so that the 3-O-sulfation rate in GlcN residues exemplified above is obtained.

The product of each step contained in the reaction solution of each step may directly be subjected to a subsequent step, or may be recovered from the reaction solution and then subjected to the subsequent step. The procedure for recovering each product from the reaction solution is not particularly limited. The procedure for recovering each product can include known techniques used for the separation and purification of the compound, such as a membrane treatment method and a precipitation method. The product in each step may be appropriately subjected to the treatments such as purification, dilution, concentration, drying, dissolution, and inactivation of the enzyme, and then subjected to the subsequent step. The purification may be performed to the desired extent. These treatments may be performed alone or in combination as appropriate.

The polysaccharide is produced by performing the heparan sulfate production step(s) as described above. The polysaccharide can be appropriately recovered from the reaction solution. The polysaccharide can be recovered by a known technique used for the separation and purification of the compound. Examples of such a technique can include an ion exchange resin method, a membrane treatment method, a precipitation method, and a crystallization method. These techniques can be used in combination as appropriate. The recovered polysaccharide may include components such as water and components used when the polysaccharide is produced, in addition to the polysaccharide. That is, the polysaccharide may be provided, for example, as a mixture containing the polysaccharide. The polysaccharide may be purified to the desired extent. The polysaccharide can be appropriately configured depending on various conditions such as utilization aspects of the polysaccharide. For example, the polysaccharide may be purified to a pharmacologically acceptable extent for compounding and utilizing as an active ingredient of a pharmaceutical composition.

Specifically, the purity of the polysaccharide may be, for example, 30% (w/w) or more, 50% (w/w) or more, 70% (w/w) or more, 80% (w/w) or more, 90% (w/w) or more, or 95% (w/w) or more.

<3> Utilization of Polysaccharide

The polysaccharide can be compounded as an active ingredient in a composition, and utilized. That is, a compound containing the polysaccharide is provided. This composition can also be referred to as the "composition as described herein". The composition can include a pharmaceutical composition. The composition may be, for example, for prevention, amelioration and/or treatment of symptoms attributed to blood coagulation. That is, the composition may be, for example, a preventive agent, an improving agent and/or a therapeutic agent for the symptoms attributed to the blood coagulation. The symptoms attributed to the blood coagulation can include disseminated intravascular coagulation (DIC), thrombotic embolism (venous thrombosis, myocardial infarction, pulmonary embolism, cerebral embolism, limb arterial thrombotic embolism, thrombotic embolism during and after operation, and the like), blood coagulation in artificial dialysis and blood coagulation in extracorporeal circulation.

The composition contains the polysaccharide as described herein. The composition may include only the polysaccharide, or may contain other component(s). The "other component(s)" is not particularly limited as long as it/they is/are pharmacologically acceptable. The "other component(s)" can include, for example, components that are compounded in the pharmaceutical composition and utilized.

For example, the composition may be formulated into any dosage form. Examples of the dosage form can include liquid agents, suspensions, powdered agents, tablets, pills, capsules, and injectable agents. Upon being formulated, for example, pharmacologically acceptable additives such as excipients, binding agents, disintegrants, lubricants, stabilizing agents, flavoring agents, odor improving agents, perfumes, diluents, surfactants, and the like can be used.

The concentration of the polysaccharide in the composition is not particularly limited as long as it is an effective amount depending on the use of the composition. That is, the concentration of the polysaccharide in the composition may be a concentration effective for the prevention, the amelioration and/or the treatment of the symptoms attributed to the blood coagulation. The concentration of the polysaccharide in the composition can be appropriately configured depending on various conditions such as the anticoagulant activity of the polysaccharide, the dosage form of the composition, and use aspects of the composition. The concentration of the polysaccharide in the composition is not particularly limited, and may be, for example, 0.01% or more, 0.1% or more, or 1% or more, 100% or less, 10% or less, or 1% or less, or a combination thereof.

The symptoms attributed to the blood coagulation in a subject can be prevented, ameliorated and/or treated by administrating the composition to the subject. That is, the present invention provides a method of preventing, ameliorating and/or treating the symptoms attributed to the blood coagulation, by administrating the composition to the subject. Also for example, for the purpose of preventing the blood coagulation in the artificial dialysis or the extracorporeal circulation, the composition could be extracorporeally added into blood. "Administrating the composition to the subject" can include not only administrating to an organism such as human but also adding to an abiotic material such as blood. That is, the "subject" referred to here may be an organism such as human or an abiotic material such as blood.

The composition can directly be administered to the subject, or can be diluted, dissolved, or dispersed using a pharmacologically acceptable solvent such as water, saline, or buffer to administer to the subject. The method of administration is not particularly limited, and can include, for example, oral administration, invasive administration such as injection, and transdermal administration. The method of administration can be appropriately configured depending on various conditions such as use of the composition. A dosage of the composition can be appropriately configured depending on various conditions such as the anticoagulant activity of the polysaccharide, the concentration of the polysaccharide, the method of administration, age, sex, and level of symptoms.

Hereinafter, the present invention will be explained more specifically based on the following non-limiting Examples.

Example 1: Preparation of Heparosan (1) Heparosan Fermentation

A culture solution containing heparosan was obtained using the heparosan-producing bacterium (*Escherichia coli* BL21 (DE3)/pVK9-kfiABCD strain) and the culture conditions described in Example 1 of WO2015/050184.

(2) Purification of Heparosan

A culture supernatant was collected from the culture solution by centrifugation. In order to remove medium ingredients, 1 mL of the culture supernatant was washed with Milli-Q water using a UF membrane, and concentrated to 250 μL. To 250 μL of the solution concentrated with the UF membrane, 500 μL of 100% ethanol was added, and heparosan was precipitated by centrifugation. The resulting precipitate was dried in air to obtain heparosan. Also from the remaining culture supernatant, heparosan was purified by the same procedure. A total of 10 g of heparosan was obtained.

Example 2: N-deacetylation of Heparosan

1) To 1.22 g of the heparosan, 61 mL of hydrazine.$H_2O$ and 4.7 mL of 1 N sulfuric acid were added, and after replacing the gas phase with nitrogen, the mixture was heated to 100° C. and allowed to react for 4.75 hours.

2) After stopping the reaction by ice cooling, 61 mL of 16% NaCl aqueous solution and 610 mL of MeOH were added and the mixture was centrifuged. The supernatant was removed. The resulting precipitate was dissolved in 50 mL of $H_2O$, and was then desalted and concentrated using Amicon UF membrane (3 kDa).

3) To the resulting concentrated solution, two times the volume of $H_2O$ and an equivalent volume of 1 M $NaHCO_3$ were added, and then, 0.2 M $I_2$/0.4 M KI solution was dripped until turning yellow in color. Subsequently, hydrazine.$H_2O$ was dripped to reduce the excessive iodine to iodine ion, and then the solution was desalted and concentrated using Amicon UF membrane (3 kDa) again. The concentrated solution was dried under reduced pressure to obtain N-deacetylated heparosan. The residual rate of the acetyl group in the obtained N-deacetylated heparosan was 14.9% (described herein).

Example 3: Depolymerization of N-deacetylated Heparosan (1) Preparation of Heparinase III <Construction of *Flavobacterium heparinum*-Derived hepC Gene Expression Plasmid>

The hepC gene encoding heparinase III native to *Flavobacterium heparinum* was cloned into a pMIV-Pnlp0 vector (US Patent Application publication 20050196846) to construct the hepC gene expression plasmid pMIV-Pnlp0-hepC. The pMIV-Pnlp0-ter plasmid can can include a potent nlp0 promoter (Pnlp0) and an rrnB terminator, and can function as an expression unit by inserting an objective gene between the promoter and the terminator. "Pnlp0" represents a promoter for the wild-type nlpD gene native to *Escherichia coli* K-12.

Details for the construction of the expression plasmid is shown below. A DNA fragment that can include about 300 bp of a promoter region (Pnlp0) for the nlpD gene was obtained by PCR with chromosomal DNA from *Escherichia coli* MG1655 as a template using primer P1 (SEQ ID NO:6) and primer P2 (SEQ ID NO:7). Sites for restriction enzymes SalI and PaeI have been designed in the 5' terminus of each of these primers. PCR cycles were as follows. First, 95° C. for 3 minutes, then two cycles of 95° C. for 60 seconds, 50° C. for 30 seconds and 72° C. for 40 seconds, subsequently 25 cycles of 94° C. for 20 seconds, 55° C. for 20 seconds and 72° C. for 15 seconds, and finally 72° C. for 5 minutes. The resulting fragment was treated with SalI and PaeI, and inserted into the SalI-PaeI site of pMIV-5JS (Japanese Patent Application Publication No. 2008-99668) to obtain plasmid pMIV-Pnlp0. The nucleotide sequence of the PaeI-SalI fragment of the Pnlp0 promoter inserted into this pMIV-Pnlp0 plasmid is shown in SEQ ID NO:8.

Subsequently, a DNA fragment (SEQ ID NO:11) that can include about 300 bp of a terminator region of the rrnB gene was obtained by PCR with chromosomal DNA from MG1655 as a template using primer P3 (SEQID NO:9) and primer P4 (SEQ ID NO:10). Sites of restriction enzymes XbaI and BamHI have been designed at the 5' terminus of each of these primers. The PCR cycles were as follows. First, 95° C. for 3 minutes, then two cycles of 95° C. for 60 seconds, 50° C. for 30 seconds and 72° C. for 40 seconds, subsequently 25 cycles of 94° C. for 20 seconds, 59° C. for 20 seconds and 72° C. for 15 seconds, and finally 72° C. for 5 minutes. The resulting fragment was treated with XbaI and BamHI, and inserted into the XbaI-BamHI site of pMIV-Pnlp0 to obtain plasmid pMIV-Pnlp0-ter.

Subsequently, a DNA chain that can include ORF of the hepC gene native to *Flavobacterium heparinum* (ATCC 13125) (Su H. et. al., Appl. Environ. Microbiol., 1996, 62: 2723-2734) was artificially synthesized. A DNA fragment of the hepC gene was amplified by PCR with this DNA chain as a template using primer P5 (SEQ ID NO:12) and primer P6 (SEQ ID NO:13). The PCR was performed using PrimeStar polymerase (TaKaRa) in the reaction composition described in the protocol. The PCR cycle was as follows. First, 94° C. for 5 minutes, then 30 cycles of 98° C. for 5 seconds, 55° C. for 10 seconds and 72° C. for 8 minutes, and finally maintaining at 4° C. Also, a DNA fragment of pMIV-Pnlp0 was obtained by PCR with pMIV-Pnlp0 as a template DNA using oligonucleotides of a primer 7 (SEQ ID NO:14) and a primer 8 (SEQ ID NO:15) as primers. PCR was performed using PrimeStar polymerase (TaKaRa) and the reaction composition described in the protocol. The PCR cycle was as follows. First, 94° C. for 5 minutes, then 30 cycles of 98° C. for 5 seconds, 55° C. for 10 seconds and 72° C. for 6 minutes, and finally keeping at 4° C. Both resulting DNA fragments were ligated using In-Fusion (registered trademark) HD cloning kit (Clontech) to construct the hepC gene expression plasmid pMIV-Pnlp0-hepC. A nucleotide sequence of the cloned hepC gene and an amino acid sequence of heparinase III (HepC) encoded by it are shown in SEQ ID NOS:16 and 17, respectively.

<Construction of *Escherichia coli* BL21 (DE3) Strain Expressing hepC Gene and Preparation of Heparinase III Enzyme Solution>

The hepC gene expression plasmid pMIV-Pnlp0-hepC was introduced into *Escherichia coli* BL21 (DE3) strain (Life Technologies) by electroporation (Cell; 80 μL, 200Ω, 25 μF, 1.8 kV, cuvette; 0.1 mL) to obtain *Escherichia coli* BL21 (DE3)/pMIV-Pnlp0-hepC strain as a heparinase III-producing strain. This strain was pre-cultured in 25 μg/mL chloramphenicol-added LB medium at 37° C. overnight. Subsequently, the culture solution was inoculated to 300 mL LB medium in a Sakaguchi flask at a final concentration of 2% v/v. The cultivation with shaking was performed at 37° C. for 4 hours, and the cultivation was stopped. After centrifugation, the microbial cells were washed twice with 0.85% NaCl, and suspended in 30 mL of 50 mM HEPES buffer (pH 7.0). The suspension was subjected to sonication disruption to disrupt the microbial cells. The disrupted microbial cell solution was centrifuged to prepare a heparinase III enzyme solution as a supernatant (cell free extract solution).

(2) Depolymerization by Heparinase III Reaction

The 1 g of N-deacetylated heparosan with an N-acetyl group residual amount of 14.9% obtained in Example 2 and 2 mL of 31.3 mIU/μL heparinase III solution were dissolved in 100 mL of Tris buffer solution (pH 8.0) containing 100 mM NaCl and 1.5 mM $CaCl_2$, and allowed to react at 37° C. for 5.3 hours. To the reaction solution, 100 mL of 16% NaCl aqueous solution and 900 mL of EtOH were added and mixed, and were then centrifuged to remove a supernatant and obtain depolymerized N-deacetylated heparosan.

Example 4: N-sulfation of Depolymerized N-deacetylated Heparosan 1) 1 g of the depolymerized N-deacetylated heparosan obtained in Example 3 was dissolved in 50 mL of MilliQ water, and 50 mL of an aqueous solution of 20 mg/mL $NaHCO_3$/20 mg/mL trimethylamine.$SO_3$ was added thereto, and the mixture was allowed to react at 55° C. overnight.

2) To the mixture, 1 L of EtOH was added, which was then centrifuged to remove the supernatant to obtain N-sulfated depolymerized heparosan.

3) The N-sulfated depolymerized heparosan was dissolved in MilliQ water up to 500 μL, and a disaccharide analysis was performed to calculate a yield relative to N-deacetylated heparosan. Also, it was subjected to GPC to calculate the molecular weight distribution. The procedures are shown below.

<Disaccharide Analysis>

The disaccharide analysis of N-sulfated depolymerized heparosan was performed according to conditions previously reported (T. Imanari, et. al., "High-performance liquid chromatographic analysis of glycosaminoglycan-derived oligosaccharides." J. O. Chromato. A, 720, 275-293 (1996)). That is, an amount of each constituent disaccharide was quantified by decomposing N-sulfated depolymerized heparosan into unsaturated disaccharides using heparinases II and III and analyzing each decomposed product by HPLC.

Likewise, the disaccharide analysis of N-deacetylated heparosan was performed. The disaccharide analysis of N-deacetylated heparosan was performed after N-deacetylated heparosan was N-sulfated. That is, the amount of each constituent disaccharide was quantified by N-sulfating N-deacetylated heparosan, subsequently decomposing it into unsaturated disaccharides using heparinases II and III, and analyzing each decomposed product by HPLC. The N-sulfation of N-deacetylated heparosan was performed with the same as the N-sulfation of depolymerized N-deacetylated heparosan.

The disaccharide analysis was specifically performed by the following procedure.

1) 0.2 U of heparinase II (Sigma), 0.02 to 0.03 mIU of heparinase III, 5 μg of a polysaccharide sample, and 10 μL of enzymatic digestion buffer (100 mM $CH_3COONa$, 10 mM $(CH_3COO)_2Ca$, pH 7.0) were mixed and diluted with Milli-Q water up to 100 μL of measured volume to use as a reaction solution.

2) This reaction solution was allowed to react at 37° C. for 16 hours or longer, and subsequently boiled at 100° C. for 2 minutes to stop the reaction.

3) Impurities were removed through a 0.45 μm filter to obtain a solution, which was then used as the sample for the disaccharide analysis.

4) The analysis was performed using a column of Inertsil ODS-3 150 mm×2.1 mm with 5 μm particle size under the conditions of temperature at 50° C., a flow date of 0.25 mL/min and a detection wavelength of 230 nm, and using an eluent composition of 4% acetonitrile and 1.2 mM tributylamine as solution A and 4% acetonitrile and 0.1 M CsCl as solution B with a gradient from 1 to 90% of solution B.

The yield was calculated from the sum of the amounts of constituent disaccharides produced from each polysaccharide sample. That is, the yield was calculated as a percentage (molar ratio) of the total amount of disaccharides produced from N-sulfated depolymerized heparosan relative to the total amount of disaccharides produced from N-deacetylated heparosan. Also, at that time, it was confirmed that 99% or more of amino groups produced by N-acetylation were N-sulfated in the obtained N-sulfated depolymerized heparosan.

Also, the residual rate of the N-acetyl groups in N-deacetylated heparosan was calculated based on the amount of each constituent disaccharide produced from N-deacetylated heparosan. That is, the residual rate of the acetyl group was calculated as a percentage (molar ratio) of the amount of disaccharides having the acetyl group relative to the total amount of disaccharides. The residual rate of the acetyl groups was 14.9%.

<GPC Analysis>

A mixture of N-sulfated depolymerized heparosan and heparan sulfate (dissolved at 1 mg/mL in MilliQ water) was subjected to gel filtration by HPLC (GPC analysis). GS520 (Shodex, Asahipak GS-520HQ, 7.5 mm×300 mm, particle size of 7 μm) was used as a column, an aqueous solution of 100 mM potassium dihydrogen phosphate was used as an eluent, and the analysis was performed at a flow rate of 0.6 mL/min, at a column temperature of 40° C., and at a detection wavelength of 200 nm. Average molecular weights (Mn and Mw) were calculated using a molecular weight marker set of pullulan (Shodex, STANDARD P-82, molecular weight range from 5900 to 708000) as a standard.

Example 5: Coupled Reaction of C5-Epimerization and 2-O-sulfation (1) Expression and Purification of C5-Epimerase The fusion protein of the catalytic site of 5-epimerase native to human (Gln29 to Asn617) and maltose binding protein (MBP) (MBP-C5-epimerase) was used as C5-epimerase. Thus, the nucleotide sequence encoding this catalytic site was cloned into pMAL-c2x vector (New England Biolabs) to construct the MBP-C5-epimerase expression plasmid pMAL-c2x-MBP-C5epi. According to the pMAL-c2x vector, the cloned gene is expressed as a fusion protein with MBP.

Details for construction of the expression plasmid are shown below. With reference to Jin-ping Li et al's report (Li J. et. al., Jour. Biol. Chem. 1997, 272: 28158-28163), cDNA of C5-epimerase native to human was prepared by artificial gene synthesis (Thermo Fisher Scientific). A DNA fragment that can include a nucleotide sequence encoding the catalytic site of C5-epimerase (Gln29 to Asn617) was obtained by PCR with this cDNA as a template using C5-epi fw (SEQ ID NO:18) and C5-epi rv (SEQ ID NO:19) as primers. The PCR was performed using PrimeStar polymerase (TaKaRa) in the reaction composition described in the protocol. The PCR cycle was as follows. First, 94° C. for 5 minutes, subsequently 30 cycles of 98° C. for 5 seconds, 55° C. for 10 seconds and 72° C. for 2 minutes, and finally maintaining at 4° C. Also, a DNA fragment of pMAL-c2x was obtained by PCR with pMAL-c2x (SEQ ID NO:20, New England Biolabs) as a template DNA using oligonucleotides of SEQ ID NOS:21 and 22 as primers. The PCR was performed using PrimeStar polymerase in the reaction composition described in the protocol. The PCR cycle was as follows. First, 94° C. for 5 minutes, subsequently 30 cycles of 98° C. for 5 seconds, 55° C. for 10 seconds and 72° C. for 6 minutes, and finally maintaining at 4° C. Both resulting DNA fragments were ligated using In-Fusion (registered trademark) HD cloning kit (Clontech) to construct the MBP-C5-epimerase expression plasmid pMAL-c2x-MBP-C5epi, in which the nucleotide sequence encoding the catalytic site of C5-epimerase is fused with the MBP gene originally included in pMAL-c2x. The nucleotide sequence of the C5-epimerase insertion fragment, that is, the nucleotide sequence encoding the catalytic site of C5-epimerase, and the amino acid sequence encoded thereby are shown in SEQ ID NOS:23 and 24, respectively.

The MBP-C5-epimerase expression plasmid pMAL-c2x-MBP-C5epi and the chaperonin expression plasmid pGro7 (TaKaRa) were introduced into *Escherichia coli* Origami B (DE3) strain (Novagen) by electroporation (Cell; 80 μL, 200Ω, 25 μF, 1.8 kV, cuvette; 0.1 mL) to obtain Origami B(DE3)/pMAL-c2x-MBP-C5epi/pGro7 strain. This strain was inoculated into the LB medium (0.1% (w/v) peptone, 0.5% (w/v) yeast extract, 1.0% (w/v) NaCl) to which 100 μg/mL ampicillin and 25 μg/mL chloramphenicol had been added, and pre-cultured at 37° C. overnight. Subsequently, the resulting culture solution was inoculated into 100 mL of the LB medium in a Sakaguchi flask to a final concentration of 1%. After cultivation with shaking at 37° C. for 3 hours, isopropyl-β-D-thiogalactopyranoside (IPTG) (Nacalai Tesque) to a final concentration of 0.5 mM and arabinose (Wako Pure Chemical) to a final concentration of 0.2% were added, and the cultivation was continued at 22° C. overnight.

After centrifuging the culture solution, microbial cells were collected, washed once with a washing solution (20 mM Tris-HCl, pH 7.5, 200 mM NaCl), and suspended in the washing solution. FastBreak (Promega) was added to the resulting suspension, which was then incubated at 30° C. for 10 minutes to one hour, and subsequently centrifuged at 9,100 g for 10 minutes. The resulting supernatant was used as a microbial cell extract solution.

(2) Expression and Purification of 2-O-sulfation Enzyme (2-OST)

The fusion protein (MBP-2-OST) of the catalytic site (Arg51 to Asn356) of the mutant of 2-OST native to Chinese hamster with substitution of tyrosine residue at position 94 with isoleucine residue with maltose binding protein (MBP) was utilized as a 2-O-sulfation enzyme (2-OST). Thus, a nucleotide sequence encoding this catalytic site was cloned into a pMAL-c2x vector (New England Biolabs) to construct the MBP-2-OST expression plasmid pMAL-c2x-MBP-2OST.

Details for the construction of the expression plasmid are shown below. With reference to Kobayashi et al's report (Kobayashi M. et. al., Jour. Biol. Chem. 1997, 272: 13980-13985), cDNA of the mutant of 2-OST native to Chinese hamster with substitution of the tyrosine residue at position 94 with an isoleucine residue was made by the artificial gene synthesis (Thermo Fisher Scientific). The DNA fragment that can can include the nucleotide sequence encoding the catalytic site (Arg51 to Asn356) of the 2-OST mutant was obtained by PCR with this cDNA fragment as a template using 2-OST fw (SEQ ID NO:25) and 2-OST rv (SEQ ID NO:26) as primers. The PCR was performed using PrimeStar polymerase (TaKaRa) in the reaction composition described in the protocol. The PCR cycle was as follows. First, 94° C. for 5 minutes, subsequently 30 cycles of 98° C. for 5 seconds, 55° C. for 10 seconds and 72° C. for 2 minutes, and finally maintaining at 4° C. Also, the DNA fragment of pMAL-c2x was obtained by PCR with pMAL-c2x as a template DNA using oligonucleotides of SEQ ID NOS:21 and 22 as primers. The PCR was performed using PrimeStar polymerase in the reaction composition described in the protocol. The PCR cycle was as follows. First, 94° C. for 5 minutes, subsequently 30 cycles of 98° C. for 5 seconds, 55° C. for 10 seconds and 72° C. for 6 minutes, and finally maintaining at 4° C. Both resulting DNA fragments were ligated using In-Fusion (registered trademark) HD cloning kit (Clontech) to construct the MBP-2-OST expression plasmid pMAL-c2x-MBP-20ST, into which the nucleotide sequence encoding the catalytic site of the 2-OST mutant was used with the MBP gene originally included in pMAL-c2x. The nucleotide sequence of the 2-OST insertion fragment (nucleotide sequence encoding the catalytic site of the 2-OST mutant) and the amino acid sequence encoded thereby are shown in SEQ ID NOS:27 and 28, respectively.

The MBP-20ST expression plasmid pMAL-c2x-MBP-20ST and the chaperonin expression plasmid pGro7 (TaKaRa) were introduced into *Escherichia coli* Origami B (DE3) strain (Novagen) according to the same technique as in Example 5(1) to obtain Origami B(DE3)/pMAL-c2x-MBP-20ST/pGro7 strain. This strain was inoculated to the LB medium with 100 μg/mL ampicillin and 25 μg/mL chloramphenicol added, and pre-cultured at 37° C. overnight. Subsequently, the resulting culture solution was inoculated into 100 mL of the LB medium in a Sakaguchi flask to a final concentration of 1%. After cultivation with shaking at 37° C. for 3 hours, isopropyl-β-D-thiogalactopyranoside (IPTG) (Nacalai Tesque) to a final concentration of 0.5 mM and arabinose (Wako Pure Chemical) to a final concentration of 0.2% were added thereto, and the cultivation was continued at 22° C. overnight.

Purified MBP-2-OST was prepared from the culture solution by the following procedure. First, the culture solution was centrifuged to collect microbial cells. Then, the microbial cells were disrupted by sonication to obtain a microbial cell extract solution. Then, the microbial cell extract solution was mixed with amylose resin (New England Biolabs) equilibrated with 20 mM Tris (pH 7.5) and 200 mM NaCl to adsorb MBP-2-OST to the resin. Subsequently, the resin was washed with the equilibration buffer in an amount of 4 times the resin, and the equilibration buffer to which 10 mM maltose had been added (elution buffer) was added. Fractions containing MBP-2-OST were fractionated to use as purified MBP-2-OST.

(3) Enzymatic Reactions (Coupled Reaction of C5-Epimerization and 2-O-sulfation)

The C5-epimerization and the 2-O-sulfation were performed using the prepared MBP-C5-epimerase microbial cell extract solution and purified MBP-2-OST. 108 mL of the extract solution of the microbial cells expressing C5-epimerase to a final concentration of 0.9 mg/mL and 16.9 mL of purified MBP-2-OST to a final concentration of 0.5 mg/mL were added to 703 mL of a mixed solution of 166 mg of N-sulfated depolymerized heparosan obtained in Example 4, 50 mM MES (pH 7.0), 100 mM NaCl, and 1 mM PAPS to prepare a reaction solution in a total amount of 828 mL. This reaction solution was allowed to react at 37° C. for 24 hours.

(4) Quantification of Conversion Rate

A conversion rate (C5-epimerization rate and 2-O sulfation rate) was quantified by a disaccharide composition analysis using nitrous acid decomposition.

<Reagents>

$NaNO_2$ (CAS No.: 7632-00-0, MW: 69.01)

Citric acid (CAS No.: 77-92-9, MW: 192.1)

2,4-Dinitrophenylhydrazine (CAS No.: 119-26-6, MW: 198.1), 50% hydrous product (abbreviation: DNPH)

Heparin (manufactured by Aldrich)

<Test Solution>

Heparin standard solution: 1 mg/mL $NaNO_2$ aqueous solution: 49.5 mg of the reagent was dissolved in 1 mL of $H_2O$.

Citric acid aqueous solution: 384.2 mg of the reagent was dissolved in 1 mL of $H_2O$.

DNPH solution: 20.4 mg (50% hydrous) of the reagent was dissolved in 1 mL of acetonitrile.

<LC-MS Analysis Conditions>

<LC Conditions>

Column: ODS Z-CLUE 3 μm 2.0 mm×250 mm manufactured by Sumika Chemical Analysis Service Column oven temperature: 50° C.

Eluent flow rate: 0.3 mL/min

Detection: UV 365 nm

Injection amount: 5 μL

Eluent composition: solution A: 50 mM $HCOONH_4$ (pH 4.5)

solution B: MeCN

TABLE 1

| Gradient conditions for LC | | |
|---|---|---|
| Time (min) | Solution A (%) | Solution B (%) |
| 0.0 | 90 | 10 |
| 13.0 | 80 | 20 |
| 27.0 | 20 | 80 |
| 27.1 | 90 | 10 |
| 40.0 | 90 | 10 |

<MS Conditions>
Ionization method: Electrospray ionization (ESI (+/−))
DL temperature: 250° C.
Heat block: 250° C.
Nebulizer gas flow rate: 1.5 L/min
Dry gas flow rate: 15 L/min

TABLE 2

| Disaccharide derivative (Structure before nitrous acid decomposition) | m/z (—) | Relative retention time (min) |
|---|---|---|
| GlcA-GlcN(NS3S6S) | 677 | 0.83 |
| GlcA(2S)-GlcN(NS6S) | | 0.97 |
| IdoA(2S)-GlcN(NS6S) | | 1 |
| GlcA-GlcN(NS6S) | 597 | 1.35 |
| GlcA(2S)-GlcN(NS) | | 1.41 |
| IdoA(2S)-GlcN(NS) | | 1.50 |
| GlcA-GlcN(NS) | 517 | 1.73 |
| IdoA-GlcN(NS) | | 1.89 |

<Analysis Procedure and Results>

The 20 μL of the heparin standard solution, 20 μL of the citrate buffer aqueous solution, and 10 μL of the $NaNO_2$ aqueous solution were added in this order into a 1.5 mL microtube (Eppendorf), and the mixed solution was stirred at 65° C. for 2 hours (1000 rpm) to obtain a nitrous acid decomposition solution. To 40 μL of the resulting nitrous acid decomposition solution, 20 μL of the DNPH solution was added, and stirred at 45° C. for 2 hours (1000 rpm) to obtain a derivatization solution. The composition of the resulting derivatization solution was analyzed by LC-MS. The conversion factor was calculated from the peak of IdoA(2S)-GlcN(NS6S) obtained by analyzing the heparin standard solution. The concentration was calculated from the area value of each disaccharide derivative in a subject solution. The calculated disaccharide structures and the ratio thereof are shown in Table 3. In the table, data for unidentified peaks thought to include disaccharide derivatives and the like having the N-acetyl group were omitted, and the total amount of GlcA(2S)-GlcN(NS), IdoA(2S)-GlcN(NS), GlcA-GlcN(NS), and IdoA-GlcN(NS) was assumed to be 100%. The C5-epimerization rate (the sum of the rates of IdoA(2S)-GlcN(NS) and IdoA-GlcN(NS)) and the 2-O-sulfation rate (the sum of the rates of GlcA(2S)-GlcN(NS) and IdoA(2S)-GlcN(NS)) were confirmed to be 58% and 65%, respectively.

TABLE 3

Disaccharide composition in reaction products by coupled reaction of C5-epimerization and 2-O-sulfation

| Disaccharide derivative | Content rate (%) |
|---|---|
| GlcA(2S)-GlcN(NS) | 12 |
| IdoA(2S)-GlcN(NS) | 53 |
| GlcA-GlcN(NS) | 30 |
| IdoA-GlcN(NS) | 5 |

Example 6: 6—O-sulfation 30 mL of the enzymatic reaction solution, that is, the reaction solution after the coupled reaction of C5-epimerization and 2-O-sulfation, obtained in Example 5 was centrifuged (7000 G, 30 minutes), and the supernatant was filtrated through a 0.45 μm filter. The filtrated solution (27.3 g) was applied onto 15 g of a weak anion exchange resin (DIAION WA-30 manufactured by Mitsubishi Chemical, preliminarily adjusted to pH 5.5 with 25.6 mM $NaH_2PO_4$) packed in a column (model number XK26) manufactured by Pharmacia to adsorb polysaccharide components onto the resin, and 480 mL of a washing solution (0.5 M NaCl+25.6 mM $NaH_2PO_4$ (pH 5.5)) was passed through the column (flow rate: 6.4 mL/min). Subsequently, 230 mL of an eluent (2 M NaCl+25.6 mM $NaH_2PO_4$ (pH 5.5)) was passed through the column (flow rate: 6.4 mL/min) to obtain the eluent containing the polysaccharide components. The obtained eluent was charged to Amicon-3K (manufactured by Merck Millipore), which was then centrifuged (4000 G). 100 mL of water was further added to the resulting concentrated solution, which was then centrifuged again. This washing manipulation was repeated three times to obtain 11 g of a washed concentrated solution.

<Ion Exchange>

11 g of the washed concentrated solution was passed through 3 mL of strong cation exchange resin (DIAION UBK550 manufactured by Mitsubishi Chemical, preliminarily exchanged to H type with 1 M hydrochloric acid) (pH 2.25), and subsequently neutralized (pH 8.36) by adding 1.8 mL of mixed solution of 2.36 mg of tributylamine/10 μL with ethanol. The obtained neutralized solution was lyophilized.

<6-O-sulfation Reaction>

Under argon gas flow, 1.92 mL of DMF and 76.4 mg (0.48 mmol) of a trioxide sulfur pyridine complex were added to a total amount of the lyophilized one, and the mixture was stirred at −10° C. for 48 hours. After the reaction, 2.8 mL of an aqueous solution of 5 M Na acetate and 31 mL of water was added and stirred at room temperature for 1 hour to stop the reaction. The reaction stopped solution was filtrated through a 0.2 μm filter, and its filtrate was charged to Amicon-3K (manufactured by Merck Millipore), which was then centrifuged (4000 G). Furthermore, 20 mL of water was added to the resulting concentrated solution, which was then centrifuged again. This manipulation was repeated twice to obtain 3.92 g of a washed concentrated solution. The obtained washed concentrated solution was sampled and subjected to the disaccharide analysis by nitrous acid decomposition according to the same procedure as in Example 5. As a result, it was confirmed that a reaction product (polysaccharide) in an amount of 76.5 mg in terms of disaccharide unit amount was contained in 3.92 g of the washed concentrated solution.

Example 7: 3—O-Sulfation Reaction in GlcN Residues (1) Preparation of Strain Expressing 3-O-sulfation Enzyme (3-OST)

The amino acid sequence of 3-OST-1 native to mouse (NCBI-Protein ID: NP_034604: SEQ ID NO:29) was obtained from the KEGG (Kyoto Encyclopedia of Genes and Genomes) database. A DNA fragment that can include the nucleotide sequence encoding the catalytic site of 3-OST-1 (Gly48 to His311) and that has been optimized based on codon usage in *Escherichia coli* (SEQ ID NO:30) was synthesized with reference to the previous report (Edavettal S. C. et al., J. Biol. Chem. 2004; 279 (24) 25789-97). The resulting DNA fragment was inserted into the EcoRI-SalI site of pETDuet-1 vector (Novagen) to construct the 3-OST-1 expression plasmid pETDuet-3-OST-1. According to this plasmid, 3-OST-1 with His-tag added to the N terminal side is expressed, and thus, it becomes possible to purify 3-OST-1 using this His-tag. This expression plasmid was introduced into *Escherichia coli* BL21 (DE3) strain according to the same technique as in Example 5 (1) to obtain the 3-OST-1 expressing strain pETDuet-3-OST-1/BL21 (DE3) strain.

(2) Expression and Purification of 3-OST-1

The *Escherichia coli* pETDuet-3-OST-1/BL21 (DE3) strain was inoculated into LB agar medium (1.0% (w/v) peptone, 0.5% (w/v) yeast extract, 1.0% (w/v) NaCl, 1.5% (w/v) agar) containing 100 μg/mL of ampicillin, and cultured statically at 37° C. overnight. Subsequently, 20 μL of microbial cells grown on the agar medium were suspended in 1 mL of the LB medium, and 50 μL thereof was added to 50 mL of Overnight Express TB medium (Merck, containing 100 μg/mL of ampicillin) in a Sakaguchi flask. The microbial cells in 16 Sakaguchi flasks were cultured with shaking at 120 reciprocations/min at 22° C. for 24 to 26 hours, and then collected by centrifugation (4° C., 8,000 rpm, 5 minutes). The microbial cells obtained as a pellet were suspended in 160 mL of an equilibration buffer (50 mM sodium phosphate, 300 mM NaCl, pH 7.0), and centrifuged (4° C., 8,000 rpm, 5 minutes) again to wash the microbial cells. After repeating this washing manipulation twice, the microbial cells obtained as a pellet were resuspended in 160 mL of the equilibration buffer, which was then subjected to disruption with sonication (190 W, 20 minutes) with ice cooling. The disrupted cell solution was centrifuged (4° C., 8,000 rpm, 10 minutes), and the resulting supernatant was used as a cell free extract solution.

The resulting cell free extract solution was applied to a column composed of three 5 mL HisTALON Superflow Cartridge linked columns (manufactured by Clontech) preliminarily equilibrated with the equilibration buffer to adsorb 3-OST-1. The column was washed with washing buffer (50 mM sodium phosphate, 300 mM NaCl, 10 mM imidazole, pH 7.0), and then 3-OST-1 was eluted with elution buffer (50 mM sodium phosphate, 300 mM NaCl, 150 mM imidazole, pH 7.0) to obtain active fractions of 3-OST-1. The buffer in the obtained active fraction was exchanged with a buffer (50 mM sodium phosphate, 300 mM NaCl, pH 7.0) using a PD-10 column (manufactured by GE Healthcare) according to the protocol. The enzyme solution after the buffer exchange was used as purified 3-OST-1 in the subsequent experiments.

(3) Enzymatic Reaction (3-O-sulfation Reaction in GlcN Residues)

The mixed solution in an amount of 326.5 mL containing the total amount of the reaction product obtained in Example 6, 50 mM HEPES (pH 7.5) and 221 μM PAPS was prepared. The 56 mL of purified 3-OST-1 was added at a final concentration of 234 mg/L to this mixed solution preliminarily warmed to 37° C. in a water bath to prepare a reaction solution in a total amount of 382.5 mL, and the reaction was initiated. The reaction was carried forward with gently stirring, and after 24 hours have passed, the enzyme was inactivated by heating at 90° C. for 20 minutes.

(4) Quantification of 3-O-sulfation Rate in GlcN Residues

The disaccharide composition analysis of the reaction product was performed by nitrous acid decomposition according to the same procedure as in Example 5. Calculated disaccharide structures and its rate are shown in Table 4.

TABLE 4

Disaccharide composition of reaction products before and after 3-O-sulfation reaction in GlcN residues

| Disaccharide derivative | Before 3-OST reaction (%) | After 3-OST reaction (%) |
|---|---|---|
| GlcA-GlcN(NS3S6S) | 0 | 13.6 |
| GlcA(2S)-GlcN(NS6S) | 10.8 | 7.6 |
| IdoA(2S)-GlcN(NS6S) | 30.0 | 27.3 |
| GlcA-GlcN(NS6S) | 25.8 | 19.2 |
| IdoA(2S)-GlcN(NS) | 24.2 | 23.3 |
| Total of unidentified peaks | 8.9 | 9.0 |

Example 8: Purification of Reaction Product 371 g of the enzymatic reaction solution, that is, the reaction solution after 3-O-sulfation reaction in GlcN residues, obtained in Example 7 was centrifuged (8000 G, 30 minutes), and its supernatant was filtrated through a 0.45 μm filter. This filtrate was charged to Amicon-3K (manufactured by Merck Millipore), which was then centrifuged (4000 G). 200 mL of water was further added to a resulting concentrated solution, which was then centrifuged again. This washing manipulation was repeated three times to obtain 11.6 g of a washed concentrated solution. This washed concentrated solution was applied onto 7.5 g of a weak anion exchange resin (DIAION WA-30 manufactured by Mitsubishi Chemical, preliminarily adjusted to pH 5.5 with 25.6 mM $NaH_2PO_4$) packed in a column (model number XK16) manufactured by Pharmacia to adsorb polysaccharide components onto the resin, and 500 mL of a washing solution (0.5 M NaCl+25.6 mM $NaH_2PO_4$ (pH 5.5)) was passed through the column (flow rate: 3.0 mL/min). Subsequently, 500 mL of an eluent (2 M NaCl+25.6 mM $NaH_2PO_4$ (pH 5.5) was passed through the column (flow rate: 3.0 mL/min) to obtain the eluent containing the polysaccharide components. 171 g of the obtained eluent was charged to Amicon-50K (manufactured by Merck Millipore), which was then centrifuged (4000 G). A resulting permeated solution was further charged to Amicon-3K (manufactured by Merck Millipore), which was then centrifuged (4000 G). 100 mL of water was further added to a resulting concentrated solution, which was then centrifuged again. This washing manipulation was repeated three times to obtain 8.58 g of a washed concentrated solution. The obtained washed concentrated solution was lyophilized to obtain 41 mg of purified polysaccharide.

Example 9: Quality Analysis of Purified Polysaccharide

The measurements shown in Table 5 are for the purified polysaccharide obtained in Example 8. Measurement methods are described herein. Results are shown in Table 5.

TABLE 5

Quality of purified polysaccharide

| Item | Unit | Measured value |
|---|---|---|
| Anti-Factor Xa | IU/mg | 211 |
| Anti-Factor IIa | IU/mg | 168 |
| LPS | EU/mg | 0.1 |

TABLE 5-continued

| Quality of purified polysaccharide | | |
|---|---|---|
| Item | Unit | Measured value |
| Protein (in terms of BSA) | μg/mg | 9 |
| GlcA-GlcN(NS3S6S) | % | 13 |
| Mw | | 34000 |
| Mn | | 23000 |

Example 10: Preparation of Sulfated Polysaccharide Having a Different Structure

Many types of sulfated polysaccharides that are different in parameters such as epimerization rate, 2-O-sulfation rate, and 3-O-sulfation rate in GlcN residues were prepared and were evaluated for anticoagulant activity.

(1) Coupled Reaction of C5-Epimerization and 2-O-Sulfation

A total of 100 mL of a reaction solution having the same reaction solution composition as in Example 5(3) was prepared, and allowed to react at 37° C. for 0 hour, 4 hours and 8 hours. A composition of disaccharides contained in the reaction product was analyzed by nitrous acid decomposition according to the same procedure as in Example 5. Calculated disaccharide structures and their rate are shown in Table 6. In the table, data for unidentified peaks thought to include disaccharide derivatives and the like having the N-acetyl group were omitted, and a total amount of GlcA(2S)-GlcN(NS), IdoA(2S)-GlcN(NS), GlcA-GlcN(NS), and IdoA-GlcN(NS) was assumed to be 100%.

TABLE 6

1) Disaccharide composition in reaction product by coupled reaction of C5-epimerization and 2-O-sulfation.

| | Content rate (%) | | |
|---|---|---|---|
| Disaccharide derivative | 0 hour | 4 hours | 8 hours |
| GlcA(2S)-GlcN(NS) | 0 | 3 | 6 |
| IdoA(2S)-GlcN(NS) | 0 | 15 | 31 |
| GlcA-GlcN(NS) | 100 | 66 | 52 |
| IdoA-GlcN(NS) | 0 | 17 | 12 |

(2) 6-O-Sulfation Reaction

Each 100 mL of the obtained enzymatic reaction solution, that is, the reaction solution after the coupled reaction of C5-epimerization and 2-O-sulfation, was purified and 6-O-sulfated according to the same procedures as in Example 6 to obtain a washed concentrated solution. The resulting washed concentrated solution was sampled and the disaccharide composition in the sample was analyzed by nitrous acid decomposition according to the same procedure as in Example 5. As a result, each sample was confirmed to contain a reaction product (polysaccharide) in an amount of about 80 μg in terms of amount of the disaccharide unit in the washed concentrated solution.

(3) 3-O-Sulfation Reaction in GlcN Residues

For the obtained reaction product of the 6-O-sulfation reaction, a reaction solution in a total amount of 300 μL was prepared in the same reaction solution composition as in Example 7, and allowed to react at 37° C. for 24 hours. The disaccharide composition of the reaction product was analyzed by nitrous acid decomposition according to the same procedure as in Example 5. Calculated disaccharide structures and the rate thereof are shown in Table 7. In the table, for the samples for 4 hours and 8 hours, data for unidentified peaks were omitted, and a total amount of the disaccharide units shown in the table was assumed to be 100%.

TABLE 7

Disaccharide composition of reaction products by 3-O-sufation reaction in GlcN residues

| | Content (%) | | |
|---|---|---|---|
| Disaccharide derivative | 0 hour | 4 hours | 8 hours |
| GlcA-GlcN(NS3S6S) | 28.6 | 33 | 23 |
| GlcA(2S)-GlcN(NS6S) | 0 | 8 | 14 |
| IdoA(2S)-GlcN(NS6S) | 0 | 6 | 7 |
| GlcA-GlcN(NS6S) | 57 | 33 | 24 |
| IdoA(2S)-GlcN(NS) | 0 | 5 | 6 |
| IdoA(2S)-GlcN(NS) | 0 | 7 | 24 |
| GlcA-GlcN(NS) | 0 | 8 | 2 |
| Total of unidentified peaks | 14.4 | — | — |

In the table, the time represents a coupled reaction time of the C5-epimerization and the 2-O-sulfation.

(4) Anticoagulant Activity of Purified Polysaccharide

The reaction products from the 3-O-sulfation reaction in GlcN residues were purified according to the same procedure as in Example 8 and were measured for anticoagulant activity. The results are shown in Table 8.

TABLE 8

| Quality of purified polysaccharides | | |
|---|---|---|
| | Anti-Factor Xa (IU/mg) | Anti-Factor IIa (IU/mg) |
| 0 hour | 135 | 150 |
| 4 hours | 261 | 148 |
| 8 hours | 244 | 145 |

In the table, the time represents a coupled reaction time of C5-epimerization and 2-O-sulfation.

<Measurement Methods>

Respective items in Examples 9 and 10 were measured according to the procedures shown below.

<Anti-Factor Xa>

Kit used: Test Team Heparin S (manufactured by Shimizu Medical)

Low molecular weight heparin standard preparation: Japanese Pharmacopoeia standard preparation (manufactured by Pharmaceutical and Medical Device Regulatory Science Society of Japan, Anti-factor Xa: 1750 IU)

Instruments used:

Mixer and incubator: Thermomixer compact (manufactured by Eppendorf)

UV absorption spectrometer: PD-3035 (manufactured by APEL)

UV cell: acrylic square cell (light path length: 10 mm)

Preparation of Reagents

Substrate solution: One vial of a substrate agent was dissolved in 20 mL of MilliQ water.

Anti-thrombin III solution: One vial of an anti-thrombin III agent was dissolved in 10 mL of MilliQ water.

Factor Xa solution: One vial of a factor Xa agent was dissolved in 10 mL of MilliQ water.

Buffer: A provided vial was directly used.

Normal plasma: One vial of a normal plasma product was dissolved in 0.1 mL of MilliQ water.

Reaction stopping solution: MilliQ water was added to 20 mL of glacial acetic acid (special grade) to make a total volume of 40 mL.

Heparin Standard Solution:

Primary diluted heparin solution (35 IU/mL): Heparin 1750 IU was dissolved in 50 mL of MilliQ water.

Secondary diluted heparin solution (0.175 IU/mL): To 100 μL of the primary diluted heparin solution, 900 μL of the buffer was precisely added and mixed. 950 μL of the buffer was precisely added to and mixed with 50 μL of this mixture.

Heparin standard solution: The secondary diluted heparin solution was diluted and mixed as shown in Table 9.

TABLE 9

| Dilution series | | | | | |
|---|---|---|---|---|---|
| ST* No | Heparin concentration (IU/mL) | Buffer (μL) | Anti-thrombin III solution (μL) | Normal plasma (μL) | Secondary diluted heparin solution (μL) |
| 1 | 0.00875 | 375 | 50 | 50 | 25 |
| 2 | 0.0175 | 350 | 50 | 50 | 50 |
| 3 | 0.035 | 300 | 50 | 50 | 100 |
| 4 | 0.0525 | 250 | 50 | 50 | 150 |
| 5 | 0.07 | 200 | 50 | 50 | 200 |

ST*: Standard solution

Preparation of Specimens (Measurement Samples)

The purified polysaccharide was diluted with or dissolved in MilliQ water so that a substrate concentration was 2 μg/mL, to obtain a diluted solution A.

TABLE 10

| Substrate concentration (μg/mL) | Buffer (μL) | Anti-thrombin III solution (μL) | Normal plasma (μL) | Diluted solution A (μL) |
|---|---|---|---|---|
| 0.2 | 350 | 50 | 50 | 50 |

Measurement Procedure

The 200 μL of a specimen was precisely collected in a microtube for measurement and a specimen blank, respectively, and incubated and stirred at 37° C. for 4 minutes. The 100 μL of factor Xa solution was added to the microtube for measurement, mixed thoroughly, left standing for 30 seconds, and then incubated at 37° C. precisely for 30 seconds. To the microtube for measurement, 200 μL of a substrate solution preliminarily incubated at 37° C. was added, mixed thoroughly, left standing for 30 seconds, and then incubated at 37° C. precisely for 180 seconds. The 300 μL of a reaction stopping solution was added to each microtube, and immediately mixed. 800 μL of the reaction solution was dispensed to a UV cell, and absorbance at a wavelength of 405 nm was measured. Likewise, the measurement was performed for the heparin standard solutions at the dilution series, and a standard curve was calculated from the heparin standard solutions. An anti-factor Xa activity in the specimen was obtained based on the standard curve. A concentration at which the coagulation of 1 mL blood was inhibited for 1 hour was defined as 1 IU/mL.

<Anti-Factor IIa>

Reagent and Kit Used

Calcium chloride solution for measuring activated partial thromboplastin time (aPTT) (0.025 mol/L, GMY-300A) manufactured by Sysmex Activated partial thromboplastin time kit Actin FSL GAC-200A manufactured by Sysmex Normal control plasma Dade Citrol level 1, GCA-110A manufactured by Sysmex Low molecular weight heparin standard preparation: Japanese Pharmacopoeia standard preparation (manufactured by Pharmaceutical and Medical Device Regulatory Science Society of Japan, Anti-factor IIa: 670 IU)

Instrument used: Semiautomatic blood coagulation measurement apparatus (CA-104 manufactured by Sysmex)

Measurement Procedure

Into a cuvette, 10 μL of the standard solution (dilution series of low molecular weight heparin standard preparation) or a subject solution (solution of purified polysaccharide), 50 μL of actin, and 50 μL of the control plasma were added, the cuvette was immediately inserted in a detection unit, and a light shielding hatch was closed. After stirring for 3 minutes, 50 μL of a calcium chloride solution was added from an introduction unit. A coagulation time was automatically displayed. An anti-factor IIa activity in the subject solution was obtained based on the standard curve calculated from the standard solutions. A concentration at which the coagulation of 1 mL blood was inhibited for one hour was defined as 1 IU/mL.

<LPS Method>

Instrument used: Toxinometer ET-6000 (manufactured by Wako Pure Chemical)

Reagents used: Lysate reagent (limulus ES-11 Single Test Wako)

Standard LPS (JPSE10000)

LPS standard solutions (EU/mL): 0.01, 0.1, 1

Measurement Procedures

Into an ES-11 Single Test Wako, 20 μL of an LPS standard solution or a subject solution (solution of purified polysaccharide) was dispensed, which was stirred using a mixer for 5 seconds. After confirming no large air bubble in the tube, the tube was inserted into position 1 in the Toxinometer (measurement was automatically initiated). A time at which a transmittance reached 94.9% was obtained, and a concentration of LPS in the subject solution was obtained based on a standard curve calculated from the LPS standard solutions.

<Protein Analysis>

Instrument used

Plate reader (SPECTRA NAX190, manufactured by Molecular Devices)

Reagents used

NaOH/$Na_2CO_3$ solution: 2 g of NaOH and 10 g of $Na_2CO_3$ were dissolved in water to make a total volume of 500 mL.

Copper sulfate/Na tartrate solution: 2.5 g of copper sulfate pentahydrate and 5.96 g of sodium tartrate dihydrate were dissolved in water to make a total volume of 500 mL.

Copper sulfate alkaline solution: 5 mL of the NaOH/$Na_2CO_3$ solution and 1 mL of the Copper sulfate/Na tartrate solution were mixed (freshly prepared).

Folin aqueous solution: Folin reagent manufactured by Aldrich (F9252-100 mL) was diluted two times with water.

Albumin standard solution: Standard solution (2 mg/mL) manufactured by Thermo Scientific was used and diluted to 0.125, 0.25, 0.5 and 1 mg/mL.

Measurement Procedure

To a 1.5 mL microtube, 20 μL of the albumin standard solution or the subject solution (solution of purified polysaccharide) and 300 μL of the copper sulfate alkaline solution were dispensed, the mixture was stirred by a mixer, and subsequently left standing for 10 minutes. 30 μL of the Folin aqueous solution was further added, and the mixture was stirred and subsequently left standing for 30 minutes. 300 μL of a resulting color-developed solution was placed in a 96-well plate, and absorbance at 750 nm was obtained. A protein concentration in the subject solution was obtained based on the standard curve calculated from the albumin standard solutions.

<Disaccharide Analysis>

The disaccharide composition was analyzed by nitrous acid decomposition according to the same procedure as in Example 5 to calculate a content rate of GlcA-GlcN (NS3S6S).

<Measurement of Average Molecular Weight>

GPC analysis was performed using molecular weight markers of pullulan as a standard according to the same procedure as in Example 4 to calculate the average molecular weights (Mn and Mw).

Example 11: Reduction of Molecular Weight of N-sulfated Heparosan Having High Residual Rate of Acetyl Group (1) N-deacetylation of heparosan 1) To 120 mg of heparosan, 6 mL of 2 M NaOH was added, and the mixture was heated up to 48° C. and allowed to react for 4.1 hours.

2) After the reaction was stopped by adding 12 mL of 6N HCl, 45 mL of MeOH was added, the mixture was then centrifuged, and supernatant was removed. The resulting pellet was dissolved in 8 mL of 0.25 M $NaHCO_3$, and subsequently the solution was desalted and concentrated using Amicon UF membrane (3 kDa) to obtain 6 mL of N-deacetylated heparosan solution. The residual rate of acetyl groups in the obtained N-deacetylated heparosan was 27.6% (described herein).

(2) Depolymerization by Heparinase III

The 6 mL of the N-deacetylated heparosan solution having 27.6% of N-acetyl group residual rate obtained (1) above and 221 μL of 10 mIU/μL heparinase III solution were mixed with 0.6 mL of Tris buffer solution (pH 8.0) containing 1 M NaCl and 15 mM $CaCl_2$), then MilliQ water was added thereto to make a total volume of 12 mL, and the mixture was allowed to react at 37° C. for 8 hours. To the reaction solution, 86 mL of EtOH was added and mixed, the solution was centrifuged, and supernatant was removed to obtain depolymerized N-deacetylated heparosan.

(3) N-sulfation of Depolymerized N-deacetylated Heparosan

1) The total amount of the depolymerized N-deacetylated heparosan obtained (2) above was dissolved in 6 mL of MilliQ water, 6 mL of an aqueous solution of 20 mg/mL of $NaHCO_3$/20 mg/mL of trimethylamine. $SO_3$ was added thereto, and the mixture was allowed to react at 55° C. overnight.

2) The 86 mL of EtOH was added thereto and mixed, the mixture was centrifuged, and supernatant was removed to obtain N-sulfated depolymerized heparosan.

3) The average molecular weights of the obtained N-sulfated depolymerized heparosan were calculated according to the same techniques as in Example 4.

Example 12: Control of Molecular Weight of Depolymerized N-sulfated Heparosan Depending on N-acetyl Group Residual Rate (1) N-deacetylation of Heparosan Heparosan was subjected to N-deacetylation reaction in the same manner as in Example 11, and N-deacetylated heparosan having 2.6% to 29.6% of residual rate of N-acetyl groups was obtained by controlling the reaction time.

(2) Depolymerization by Heparinase III

The N-deacetylated heparosan obtained in (1) above was allowed to react with heparinase III under the same conditions as in Example 11 to obtain depolymerized N-deacetylated heparosan.

(3) N-sulfation of Depolymerized N-deacetylated Heparosan

The depolymerized N-deacetylated heparosan obtained in (2) above was subjected to N-sulfation reaction under the same conditions as in Example 11 to obtain N-sulfated depolymerized heparosan.

(4) Summary of Average Molecular Weights

The average molecular weights of the obtained N-sulfated depolymerized heparosan were calculated according to the same technique as in Example 4. The resulting yields and average molecular weights (in terms of pullulan) are shown in Table 11.

From the results in Table 11, it was shown that the molecular weight could be controlled to be reduced by increasing the residual rate of N-acetyl groups.

TABLE 11

| | N—Ac % | Mn (in terms of pullulan) | Mw (in terms of pullulan) |
|---|---|---|---|
| No. A | 27.6% | 9000 | 15000 |
| No. B | 17.6% | 15000 | 27000 |
| No. C | 2.6% | 54000 | 87000 |
| No. D (No treatment for depolymerization) | 29.6% | 138000 | 175000 |

Example 13: Preparation of Depolymerized N-sulfated Heparosan for Examining Difference of Activity Due to Difference of Molecular Weight Since a residual amount of the N-acetyl groups affects the activity of heparan sulfate, for the purpose of examining the effect of the difference of the molecular weight on the activity, samples of depolymerized N-sulfated heparosan having the same residual amount of the N-acetyl groups and different molecular weights were prepared. The molecular weight was controlled by the reaction time for the depolymerization reaction.

(1) N-Deacetylation of Heparosan

Heparosan was subjected to N-deacetylation reaction in the same manner as in Example 11 to obtain N-deacetylated heparosan having 29.4% of N-acetyl group residual amount.

(2) Depolymerization by Heparinase III Reaction

The depolymerization of the N-deacetylated heparosan obtained in (1) above was performed by reacting with heparinase III under the same conditions as in Example 11. The molecular weight was controlled by changing the additive amount of oxygen and the reaction time to obtain four kinds of depolymerized N-deacetylated heparosan.

(3) N-sulfation of Depolymerized N-deacetylated Heparosan

The four kinds of depolymerized N-deacetylated heparosan obtained in (2) above were subjected to the N-sulfation reaction under the same conditions as in Example 11 to obtain N-sulfated depolymerized heparosan.

(4) The yields and the molecular weight distribution of the obtained N-sulfated depolymerized heparosan were calculated according to the same techniques as in Example 4.

TABLE 12

| | Amount of added heparinase III | Depolymerization time | Mn (in terms of pullulan) | Mw (in terms of pullulan) |
|---|---|---|---|---|
| No. 1 | 0.79 | 6.0 hours | 12000 | 17000 |
| No. 2 | 0.79 | 2.7 hours | 18000 | 27000 |
| No. 3 | — | — | 119000 | 158000 |

Example 14: Preparation of Sulfated Polysaccharides Having Different Molecular Weights (1) (1) Expression and Purification of C5-Epimerase As C5-epimerase, the fusion protein (MBP*-C5-epimerase (G101)) of the catalytic site of C5-epimerase native to human (Gly101 to Asn617) and the maltose binding protein having substituted three amino acids at the C-terminus (MBP*, previous report (Rob J. Center, et. al., "Crystallization of a trimeric human T cell leukemia virus type 1 gp21 ectodomain fragment as a chimera with maltose-binding protein." Protein Science, 7, 1612-1619 (1998))) was utilized.

Details for construction of the expression plasmid are shown below. First, a DNA fragment of the C-terminal region of MBP* was obtained by PCR with pMAL-c2x (SEQ ID NO:20, New England BioLabs) as a template DNA using oligonucleotides of SEQ ID NOS:31 and 32 as primers. In the above PCR reaction, a recognition site for restriction enzyme BglII was added to 5' terminus, and recognition sites for restriction enzymes HindIII, BamHI, SacI, XhoI and NotI were added to 3' terminus. pMAL-c2x plasmid DNA and the DNA fragment of the C-terminal region of MBP* were cleaved with BglII and HindIII, and ligated to obtain pMAL-MBP* plasmid. The nucleotide sequence of the pMAL-MBP* plasmid is shown in SEQ ID NO:33.

A DNA fragment of C5-epimerase (G101) was obtained by PCR with the pMAL-c2x-MBP-C5epi plasmid prepared in Example 5 as a template DNA using oligonucleotides of SEQ ID NOS:34 and 35 as primers. In this PCR, a recognition site for restriction enzyme NotI was added to the 5' terminus and a recognition site for restriction enzyme XhoI was added to the 3' terminus. The pMAL-c2x-MBP-C5epi plasmid DNA and the DNA fragment of C5-epimerase (G101) were cleaved with NotI and XhoI and ligated to obtain pMAL-MBP*-C5epi (G101) plasmid. The nucleotide sequence of the insertion fragment (nucleotide sequence encoding the catalytic site (Gly101 to Asn617) of C5-epimerase) and the amino acid sequence encoded thereby are shown in SEQ ID NOS:36 and 37, respectively. The expression plasmid pMAL-MBP*-C5epi (G101) and the chaperonin expression plasmid pGro7 (TaKaRa) were introduced into *Escherichia coli* Origami B (DE3) strain (Novagen) in the same method as in Example 5 to obtain an Origami B (DE3)/pMAL-MBP*-C5epi (G101)/pGro7 strain. A microbial cell extract solution was prepared using this strain according to the same method as in Example 5.

(2) Expression and Purification of 2-O-sulfation Enzyme (2-OST)

As 2-O-sulfation enzyme (2-OST), a fusion protein of the catalytic site (Asp68 to Asn356) of the mutant of 2-OST native to Chinese hamster with substitution of tyrosine residue at position 94 with isoleucine and MBP* (MBP*-2-OST (D68)) was utilized.

Details for construction of the expression plasmid are shown below. A DNA fragment of 2-OST (D68) was obtained by PCR with the pMAL-c2x-MBP-20ST plasmid made in Example 5 as a template DNA using oligonucleotides of SEQ ID NOS:38 and 39 as primers. In this PCR, recognition sites for restriction enzymes NotI and XhoI were added to the 5' terminus and the 3' terminus, respectively. The pMAL-c2x-MBP-20ST plasmid DNA and the DNA fragment of 2-OST (D68) were cleaved with NotI and XhoI and ligated to obtain pMAL-MBP*-2OST (D68) plasmid. The nucleotide sequence of the insertion fragment (nucleotide sequence encoding the catalytic site (Asp68 to Asn356) of 2-OST) and the amino acid sequence encoded thereby are shown in SEQ ID NOS:40 and 41, respectively. The MBP*-2-OST (D68) expression plasmid pMAL-MBP*-2OST (D68) and the chaperonin expression plasmid pGro7 (TaKaRa) were introduced into *Escherichia coli* Origami B (DE3) strain (Novagen) according to the same method as in Example 5 to obtain Origami B (DE3)/pMAL-MBP*-2OST (D68)/pGro7 strain. A purified 2-OST protein was prepared using this strain in the same method as in Example 5.

(3) Coupled Reaction of C5-Epimerization and 2-O-sulfation

To 68.9 mL of a mixed reaction solution containing 14 mg of the N-sulfated heparosan No. 1, No. 2, or No. 3 prepared in Example 13, 50 mM IVIES (pH 7.0), 100 mM NaCl, and 0.5 mM PAPS, 0.7 mL of an extract solution from microbial cells expressing C5-epimerase at a final concentration of 0.09 mg/mL and 0.4 mL of the purified 2-OST protein at a final concentration of 0.07 mg/mL were added to prepare a reaction solution in a total volume of 70 mL, which was then allowed to react at 37° C. for 10 hours.

The composition of the disaccharides contained in the reaction product was analyzed by nitrous acid decomposition according to the same procedure as in Example 5. The calculated disaccharide structures and the amounts thereof are shown in Table 13. In the table, data for unidentified peaks thought to can include disaccharide derivatives and the like having the N-acetyl group were omitted, and a total amount of GlcA(2S)-GlcN(NS), IdoA(2S)-GlcN(NS), GlcA-GlcN(NS), and IdoA-GlcN(NS) was assumed to be 100%.

TABLE 13

Content rate (%) of disaccharide composition in reaction product by coupled reaction of C5-epimerization and 2-O-sulfation

| | Reaction product | | |
|---|---|---|---|
| | No. 4 | No. 5 | No. 6 |
| | Substrate used | | |
| | No. 1 | No. 2 | No. 3 |
| Disaccharide derivative | Content amount (%) | | |
| GlcA(2S)-Glc(NS) | 6 | 8 | 1 |
| IdoA(2S)-Glc(NS) | 14 | 18 | 21 |
| GlcA-Glc(NS) | 70 | 67 | 67 |
| IdoA-Glc(NS) | 10 | 7 | 11 |

(4) C5-Epimerization Reaction

To 5.4 mL of the mixed reaction solution containing 14 mg of the N-sulfated heparosan No. 1, No. 2 or No. 3 prepared in Example 13, 50 mM MES (pH 7.0), and 100 mM NaCl, 0.6 mL of an extract solution from microbial cells expressing C5-epimerase at a final concentration of 1.0 mg/mL was added to prepare a reaction solution in a total volume of 5 mL, which was then allowed to react at 37° C.

for 24 hours. The same C5-epimerase as used in Example 14(1) was used. The composition of the disaccharides contained in a reaction product was analyzed by nitrous acid decomposition according to the same procedures as in Example 5. Calculated disaccharide structures and its rate are shown in Table 14.

TABLE 14

Content rate (%) of disaccharide composition in reaction product by C5-epimerization reaction

| | Reaction product | | |
|---|---|---|---|
| | No. 7 | No. 8 | No. 9 |
| | Substrate used | | |
| Disaccharide derivative | No. 1 | No. 2 | No. 3 |
| Disaccharide derivative | Content rate (%) | | |
| GlcA-Glc(NS) | 67 | 68 | 69 |
| IdoA-Glc(NS) | 33 | 32 | 31 |

(5) 6-O-Sulfation Reaction

The obtained enzyme reaction solutions No. 4 to No. 9, that is, the reaction solutions after the coupled reaction of the C5-epimerization and the 2-O-sulfation, or the reaction solutions after the C5-epimerization reaction alone, were purified and 6-O-sulfated according to the same procedures as in Example 6 to obtain washed concentrated solutions.

(6) 3-O-sulfation Reaction

A reaction solution having the same reaction solution composition as in Example 7 and a total amount of 300 μL including 80 μg of the reaction product obtained from the 6-O-sulfation reaction was prepared, and allowed to react at 37° C. for 24 hours. The composition of disaccharides in the reaction product was analyzed by nitrous acid decomposition according to the same procedure as in Example 5. The calculated disaccharide structures and the rate thereof are shown in Table 15. Data for unidentified peaks were omitted, and a total amount of the disaccharide units shown in the table was assumed to be 100%.

TABLE 15

Disaccharides composition in reaction products by 3-O-sulfation reaction

| Disaccharide | Content rate (%) | | | | | |
|---|---|---|---|---|---|---|
| derivative | No. 4 | No. 5 | No. 6 | No. 7 | No. 8 | No. 9 |
| GlcA-GlcN(NS3S6S) | 30.4 | 37.0 | 20.9 | 45.5 | 40.5 | 22.3 |
| GlcA(2S)-GlcN(NS6S) | 7.5 | 4.7 | 0 | 8.1 | 7.9 | 3.8 |
| IdoA(2S)-GlcN(NS6S) | 9.3 | 7.5 | 6.9 | 0 | 0 | 0 |
| GlcA-GlcN(NS6S) | 26.2 | 24.5 | 20.7 | 25.5 | 27.8 | 16.9 |
| IdoA(2S)-GlcN(NS) | 9.7 | 5.4 | 24.6 | 0 | 0 | 0 |
| IdoA-GlcN(NS6S) | 0 | 0 | 0 | 6.7 | 7.7 | 23 |
| GlcA-GlcN(NS) | 4.8 | 4.5 | 9.8 | 4.0 | 3.6 | 24.7 |
| Sum of unidentified peaks | 12.1 | 16.4 | 17.1 | 10.2 | 12.5 | 9.3 |

(7) Anticoagulant Activity of Purified Polysaccharides

The reaction products of the 3-O-sulfation reaction was purified according to the same procedure as in Example 8, and their anticoagulant activity was measured. Results are shown in Table 16.

TABLE 16

Quality of purified polysaccharides

| | Anti-Factor Xa (IU/mg) | Anti-Factor IIa (IU/mg) | Mn (in terms of pullulan) | Mw (in terms of pullulan) |
|---|---|---|---|---|
| No. 4 | 220 | 181 | 18000 | 22000 |
| No. 5 | 275 | 227 | 25000 | 31000 |
| No. 6 | 232 | 212 | 111000 | 145000 |
| No. 7 | 262 | 149 | 24000 | 29000 |
| No. 8 | 288 | 257 | 32000 | 40000 |
| No. 9 | 234 | 266 | 116000 | 145000 |

EXPLANATION OF SEQUENCE LISTING

SEQ ID NO:1 Nucleotide sequence of kfiABCD operon from *Escherichia coli* K5 strain SEQ ID NO:2 Amino acid sequence of KfiA protein from *Escherichia coli* K5 strain SEQ ID NO:3 Amino acid sequence of KfiB protein from *Escherichia coli* K5 strain SEQ ID NO:4 Amino acid sequence of KfiC protein from *Escherichia coli* K5 strain SEQ ID NO:5 Amino acid sequence of KfiD protein from *Escherichia coli* K5 strain SEQ ID NOS:6 and 7 Primers SEQ ID NO:8 Nucleotide sequence of PaeI-SalI fragment including wild type nlpD promoter (Pnlp0)

SEQ ID NOS:9 and 10 Primers

SEQ ID NO:11 Nucleotide sequence of rrnB terminator

SEQ ID NOS:12 to 15 Primers

SEQ ID NO:16 Nucleotide sequence of hepC gene from *Flavobacterium heparinum* ATCC 13125

SEQ ID NO:17 Amino acid sequence of HepC protein from *Flavobacterium heparinum* ATCC 13125

SEQ ID NOS:18 and 19 Primers

SEQ ID NO:20 pMAL-c2x

SEQ ID NOS:21 and 22 Primers

SEQ ID NO:23 Nucleotide sequence of C5-epomerase inserted fragment (nucleotide sequence encoding catalytic site of C5-epimerase native to human)

SEQ ID NO:24 Amino acid sequence of catalytic site of C5-epimerase native to human SEQ ID NOS:25 and 26 Primers SEQ ID NO:27 Nucleotide sequence of 2-OST inserted fragment (nucleotide sequence encoding catalytic site of 2-OST mutant native to Chinese hamster)

SEQ ID NO:28 Amino acid sequence of catalytic site of 2-OST mutant native to Chinese hamster SEQ ID NO:29 Amino acid sequence of 3-OST-1 native to mouse SEQ ID NO:30 Nucleotide sequence optimized for codon usage in *Escherichia coli* and encoding catalytic site (Gly48 to His311) of 3-OST-1 native to mouse SEQ ID NOS:31 and 32 Primers SEQ ID NO:33 pMAL-MBP*

SEQ ID NOS:34 and 35 Primers

SEQ ID NO:36 Nucleotide sequence of C5-epomerase (G101) inserted fragment (nucleotide sequence encoding catalytic site (Gly101 to Asn617) of C5-epimerase native to human)

SEQ ID NO:37 Amino acid sequence of catalytic site (Gly101 to Asn617) of C5-epimerase native to human SEQ ID NOS:38 and 39 Primers SEQ ID NO:40 Nucleotide sequence of 2-OST (D68) inserted fragment (nucleotide sequence encoding catalytic site (Asp68 to Asn356) of 2-OST mutant native to Chinese hamster)

SEQ ID NO:41 Amino acid sequence of catalytic site (Asp68 to Asn356) of 2-OST mutant native to Chinese hamster

The invention claimed is:

1. A polysaccharide having an anticoagulant activity, said polysaccharide comprising a repetitive disaccharide unit having the following general formula (I):

(I)

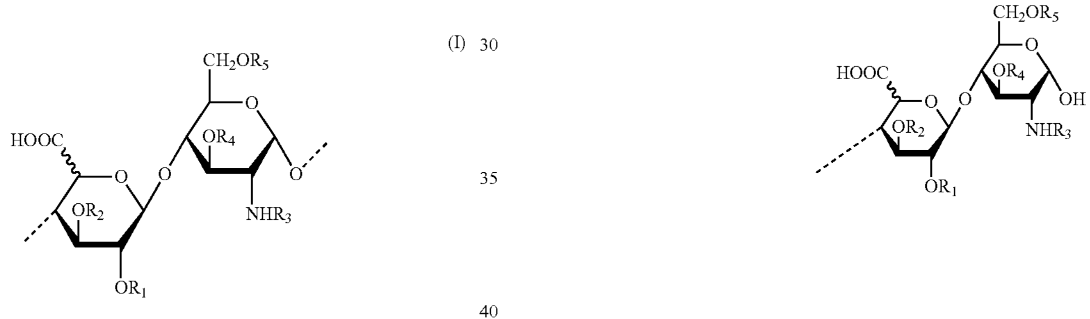

wherein, $R_1$, $R_2$, $R_4$, and $R_5$ each independently represent a hydrogen or a sulfate group;

$R_3$ represents a hydrogen, a sulfate group, or an acetyl group;

at least a portion of the $R_3$ is the sulfate group;

the rate of the sulfate group as $R_4$ is 13% or more; and the rate of the sulfate group as $R_5$ is 50% or more;

wherein 50% or more of the total number of sugar chains present in said polysaccharide have the following general formula (II):

(II)

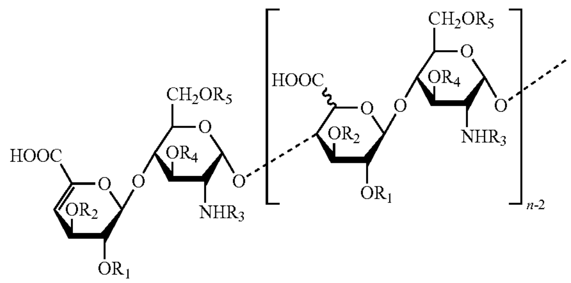

-continued wherein, $R_1$ to $R_5$ are the same as $R_1$ to $R_5$ in said general formula (I); and n is 3 to 30 as an average value; and wherein the number average molecular weight measured by gel permeation chromatography using pullulan as a standard is 12000 to 40000;

wherein the ratio of anti-factor Xa activity to anti-factor IIa activity is 1.5 or more.

2. The polysaccharide according to claim 1, wherein the content rate of said disaccharide unit is 90% or more.

3. The polysaccharide according to claim 1, wherein 50% or more of the total number of sugar chains present in said polysaccharide have the following general formula (II):

(II)

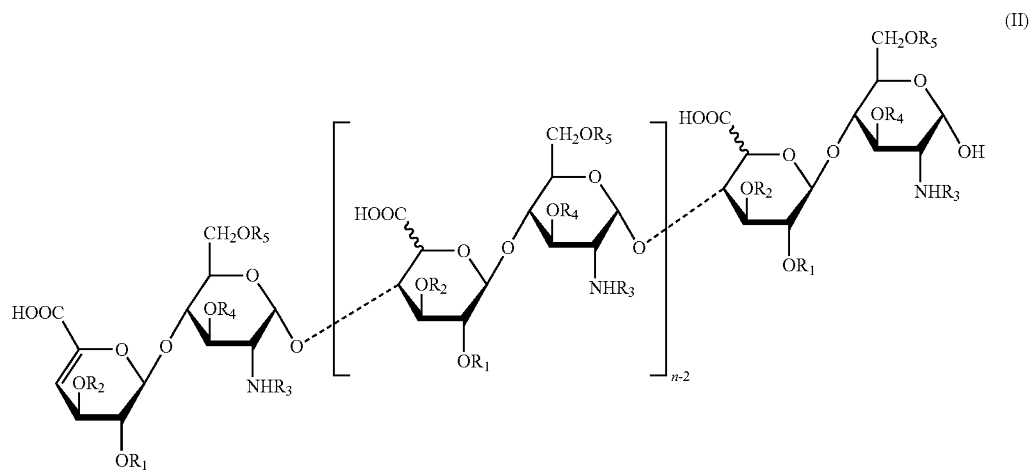

wherein, $R_1$ to $R_5$ are the same as $R_1$ to $R_5$ in said general formula (I); and n is 3 to 15 as the average value.

4. The polysaccharide according to claim 1, wherein the average number of linked sugar residues is 6 to 60.

5. The polysaccharide according to claim 1, wherein the average number of linked sugar residues is 6 to 30.

6. The polysaccharide according to claim 1, wherein the weight average molecular weight measured by gel permeation chromatography using pullulan as a standard is 10000 to 100000.

7. The polysaccharide according to claim 1, wherein the weight average molecular weight measured by gel permeation chromatography using pullulan as a standard is 15000 to 50000.

8. The polysaccharide according to claim 1, wherein the rate of iduronic acid residues as hexuronic acid residues in said disaccharide unit is 0% to 70%.

9. The polysaccharide according to claim 1, wherein the rate of a sulfate group as $R_1$ is 0% to 80%.

10. The polysaccharide according to claim 1, wherein the rate of a sulfate group as $R_1$ in iduronic acid residues is 0% to 100%.

11. The polysaccharide according to claim 1, wherein the rate of a sulfate group as $R_1$ in glucuronic acid residues is 0% to 50%.

12. The polysaccharide according to claim 1, wherein the rate of a sulfate group as $R_2$ is less than 1%.

13. The polysaccharide according to claim 1, wherein the rate of a sulfate group as $R_3$ is 70% to 100%.

14. The polysaccharide according to claim 1, wherein the rate of a acetyl group as $R_3$ is 0 to 33%.

15. The polysaccharide according to claim 1, wherein the rate of a sulfate group as $R_4$ is 45% or less.

16. The polysaccharide according to claim 1, wherein the rate of a sulfate group as $R_5$ is 70% to 100%.

17. The polysaccharide according to claim 1, comprising a disaccharide unit selected from the group consisting of GlcA-G1cN(NS3S6S), GlcA(2S)-G1cN(NS6S), IdoA(2S)-GlcN(NS6S), GlcA-G1cN(NS6S), IdoA(2S)-G1cN(NS), IdoA(2S)-G1cN(NS3S), IdoA-GlcN(NS6S), GlcA-G1cN (NS), and combinations thereof at a total content rate of 50% or more.

18. The polysaccharide according to claim 1, wherein the ratio (Mw/Mn) of a weight average molecular weight (Mw) to a number average molecular weight (Mn) measured by gel permeation chromatography using pullulan as a standard is 1.5 or less.

19. The polysaccharide according to claim 1, which is a free form, or a pharmacologically acceptable salt, or a mixture thereof.

20. The polysaccharide according to claim 19, wherein said salt is selected from the group consisting of an ammonium salt, a sodium salt, a lithium salt, and a calcium salt.

21. A pharmaceutical composition comprising the polysaccharide according to claim 1.

22. A method of preventing, ameliorating, and/or treating a symptom attributed to blood coagulation comprising administering the composition according to claim 21 to a subject in need thereof.

23. The method according to claim 22, wherein said symptom is selected from the group consisting of disseminated intravascular coagulation syndrome, thrombotic embolism, blood coagulation in artificial dialysis, and blood coagulation in extracorporeal circulation.

* * * * *